US011786160B2

(12) United States Patent
Hatakeyama et al.

(10) Patent No.: US 11,786,160 B2
(45) Date of Patent: Oct. 17, 2023

(54) BIO-ELECTRODE COMPOSITION, BIO-ELECTRODE, AND METHOD FOR MANUFACTURING BIO-ELECTRODE

(71) Applicant: SHIN-ETSU CHEMICAL CO., LTD., Tokyo (JP)

(72) Inventors: Jun Hatakeyama, Joetsu (JP); Osamu Watanabe, Joetsu (JP); Motoaki Iwabuchi, Joetsu (JP); Shiori Nonaka, Joetsu (JP); Koji Hasegawa, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 1285 days.

(21) Appl. No.: 16/272,321

(22) Filed: Feb. 11, 2019

(65) Prior Publication Data
US 2019/0254548 A1 Aug. 22, 2019

(30) Foreign Application Priority Data

Feb. 22, 2018 (JP) ................. 2018-030014

(51) Int. Cl.
A61B 5/25 (2021.01)
C08L 33/14 (2006.01)
C08L 41/00 (2006.01)
A61B 5/00 (2006.01)
C08K 3/04 (2006.01)
C08K 3/08 (2006.01)
A61B 5/0245 (2006.01)

(52) U.S. Cl.
CPC .............. A61B 5/25 (2021.01); A61B 5/6802 (2013.01); C08L 33/14 (2013.01); C08L 41/00 (2013.01); A61B 5/0245 (2013.01); A61B 2562/0215 (2017.08); C08K 3/041 (2017.05); C08K 3/08 (2013.01); C08K 2003/085 (2013.01); C08K 2003/0806 (2013.01); C08K 2003/0831 (2013.01); C08K 2003/0862 (2013.01); C08K 2201/001 (2013.01); C08L 2203/02 (2013.01)

(58) Field of Classification Search
CPC .... C08L 41/00; C08L 33/00; C08L 33/02–26; C08F 14/18; C08F 14/185; C08F 22/00; C08F 22/02; C08F 22/10–28; C08F 22/36; C08F 22/385; C08F 22/40; A61B 5/25
See application file for complete search history.

(56) References Cited

U.S. PATENT DOCUMENTS

| | | | |
|---|---|---|---|
| 2002/0177039 A1 | 11/2002 | Lu et al. | |
| 2013/0189220 A1 | 7/2013 | Komoriya et al. | |
| 2015/0025293 A1* | 1/2015 | Feiring ................. | B01D 71/82 585/818 |
| 2016/0155530 A1 | 6/2016 | Someya et al. | |
| 2017/0130071 A1* | 5/2017 | Hatakeyama ......... | C08F 220/24 |
| 2017/0323698 A1 | 11/2017 | Hatakeyama et al. | |

FOREIGN PATENT DOCUMENTS

| | | |
|---|---|---|
| CN | 1680306 A | 10/2005 |
| JP | H05-095924 A | 4/1993 |
| JP | 2003-225217 A | 8/2003 |
| JP | 2004-033468 A | 2/2004 |
| JP | 2004-527902 A | 9/2004 |
| JP | 2012-092088 A | 5/2012 |
| JP | 2015-019806 A | 2/2015 |
| JP | 2015-100673 A | 6/2015 |
| TW | 201734149 A | 10/2017 |
| TW | 201804954 A | 2/2018 |
| WO | 2013/039151 A1 | 3/2013 |

OTHER PUBLICATIONS

Sep. 20, 2019 Office Action and Search Report issued in Taiwanese Patent Application No. 108105538.

* cited by examiner

Primary Examiner — Ana L. Woodward
(74) Attorney, Agent, or Firm — Oliff PLC

(57) ABSTRACT

The present invention provides a bio-electrode composition comprising a polymer compound having a repeating unit A that contains silver salt of fluorosulfonic acid, silver salt of fluorosulfonimide, or silver salt of fluorosulfonamide. This can form a living body contact layer for a bio-electrode with excellent electric conductivity, biocompatibility and light weight, which can be manufactured at low cost and does not cause large lowering of the electric conductivity even when it is wetted with water or dried. The present invention also provides a bio-electrode in which the living body contact layer is formed from the bio-electrode composition and a method for manufacturing the bio-electrode.

15 Claims, 2 Drawing Sheets ate, it has
been difficult to achieve both the electric conductivity and
the biocompatibility.

BIO-ELECTRODE COMPOSITION, BIO-ELECTRODE, AND METHOD FOR MANUFACTURING BIO-ELECTRODE

TECHNICAL FIELD

The present invention relates to a bio-electrode, which is in contact with living skin and can detect physical conditions such as a heart rate on the basis of electric signals from the skin, and a method for manufacturing the same, as well as a bio-electrode composition that is suitably used for a bio-electrode.

BACKGROUND ART

In recent years, wearable devices have been developed progressively with the spread of Internet of Things (IoT). Representative examples thereof include a watch and glasses that can be connected with internet. Wearable devices that can always monitor physical conditions are also necessary in a medical field and a sports field, and are expected to be a growth field in the future.

In the medical field, wearable devices have been investigated to monitor organic conditions by sensing a weak current such as an electrocardiogram measurement, which detects heart beats by electric signals. The electrocardiogram is measured by fitting a body with electrodes on which electro-conductive paste is applied, and this measurement is performed only once in a short period of time. On the other hand, the aim of development of the foregoing medical wearable device is to develop devices that monitor health conditions continuously for several weeks. Accordingly, bio-electrodes used for a medical wearable device have to keep the electric conductivity unchanged and not to cause skin allergies even when being used for a long time. In addition to these, it is desirable that the bio-electrode is light in weight and can be manufactured at low cost.

Medical wearable devices include a type in which the device is attached to a body and a type in which the device is incorporated into clothes. As the type in which the device is attached to a body, it has been proposed a bio-electrode using water soluble gel containing water and electrolyte, which are materials of the foregoing electro-conductive paste (Patent Document 1). The water soluble gel contains sodium, potassium, or calcium as the electrolyte in a water soluble polymer for retaining water, and converts changes of ion concentration from skin into electricity. On the other hand, as the type in which the device is incorporated into clothes, it has been proposed a means to use cloth in which an electro-conductive polymer such as poly-3,4-ethylenedioxythiophene-polystyrenesulfonate (PEDOT-PSS) or silver paste is incorporated into the fibers for electrodes (Patent Document 2).

When using the foregoing water soluble gel containing water and electrolyte, however, the electric conductivity is lost as the water is lost due to drying. On the other hand, some people can cause skin allergies by the use of metal with high ionization tendency such as copper. The use of an electro-conductive polymer such as PEDOT-PSS also has a risk of skin allergies due to the strong acidity of the electro-conductive polymer.

As the electrode material, it has been investigated to use metal nanowire, carbon black, carbon nanotube and so on since they have excellent electric conductivity (Patent Documents 3, 4, and 5). The metal nanowire can conduct electricity in a small loading amount since the wires are brought into contact with each other in high probability. The metal nanowire, however, can cause skin allergies since they are thin material with sharp tips. The carbon nanotube also has stimuli to a living body by the same reason. The carbon black has some irritativeness to skin, although the toxicity is lower than the carbon nanotube. As described above, the biocompatibility is sometimes worsened due to the shape and irritativeness of a material, even though the material itself does not cause an allergic reaction. Accordingly, it has been difficult to achieve both the electric conductivity and the biocompatibility.

Metal films are assumed to function as an excellent bio-electrode due to their very high electric conductivity, but such assumption is not always correct. It is a sodium, potassium, or calcium ion that is emitted from skin caused by heartbeat, not a weak current signal. This makes it necessary to convert the change of ion concentration to current. Noble metals, however, are difficult to ionize and are inefficient in converting ions from skin to current. Accordingly, bio-electrodes with noble metal have high impedance and higher resistance in a current flow with skin.

On the other hand, batteries with added ionic liquids have been investigated (Patent Document 6). Ionic liquids are characteristic in higher thermal and chemical stability as well as excellent electric conductivity, and application thereof has been spreading in battery uses. Such an ionic liquid with smaller molecular weight as shown in Patent Document 6, however, dissolves in water and is extracted with perspiration from skin in the use of bio-electrode containing the ionic liquid, thereby permeating skin to cause rough dry skin, not only lowering the electric conductivity.

When the bio-electrode is away from a body, it becomes impossible to obtain information from the body. Just the change of contact area fluctuates the quantity of electricity to be conducted, thereby fluctuating the baseline of an electrocardiogram (electric signals). Accordingly, the bio-electrode have to be in contact with skin continually without changing the contact area in order to obtain stable electric signals from a body. For that purpose, the bio-electrode preferably has tackiness. It also needs elasticity and flexibility to cope with expansion and contraction as well as change of bending of skin.

PRIOR ART DOCUMENTS

Patent Documents

Patent Document 1: International Patent Laid-Open Publication No. WO 2013/039151
Patent Document 2: Japanese Unexamined Patent Application Publication (Kokai) No. 2015-100673
Patent Document 3: Japanese Unexamined Patent Application Publication (Kokai) No. H5-095924
Patent Document 4: Japanese Unexamined Patent Application Publication (Kokai) No. 2003-225217
Patent Document 5: Japanese Unexamined Patent Application Publication (Kokai) No. 2015-019806
Patent Document 6: Japanese Unexamined Patent Application Publication (Kohyo) No. 2004-527902

SUMMARY OF INVENTION

Technical Problem

The present invention has been accomplished to solve the foregoing problems, and an object thereof is to provide a bio-electrode composition that can form a living body contact layer for a bio-electrode with excellent electric conductivity and biocompatibility as well as light weight which can be manufactured at low cost and does not cause large lowering of the electric conductivity even when it is wetted with water or dried; a bio-electrode in which the living body contact layer is formed from the bio-electrode composition; and a method for manufacturing the bio-electrode.

Solution to Problem

To solve the problems, the present invention provides a bio-electrode composition comprising a polymer compound having a repeating unit A that contains silver salt of fluorosulfonic acid, silver salt of fluorosulfonimide, or silver salt of fluorosulfonamide.

The Inventive bio-electrode composition can form a living body contact layer for a bio-electrode with excellent electric conductivity and biocompatibility as well as light weight, which can be manufactured at low cost and does not cause large lowering of the electric conductivity even when it is wetted with water or dried.

It is preferable that the repeating unit A have a structure shown by the following general formula (1)-1, (1)-2, (1)-3, or (1)-4 as the silver salt of fluorosulfonic acid, the silver salt of fluorosulfonimide, or the silver salt of fluorosulfonamide,

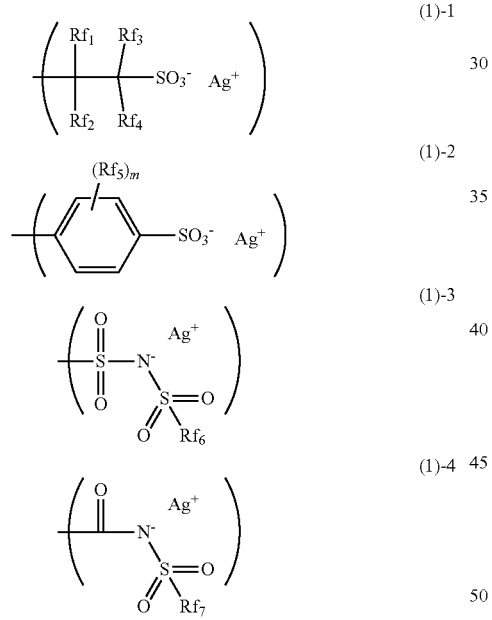

wherein $Rf_1$ and $Rf_2$ each represent a hydrogen atom, a fluorine atom, a trifluoromethyl group, or an oxygen atom, provided that when $Rf_1$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that one or more fluorine atoms are contained in $Rf_1$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; and "m" is an integer of 1 to 4.

It is preferable that the repeating unit A be one or more repeating units selected from repeating units A1 to A7 shown by the following general formulae (2),

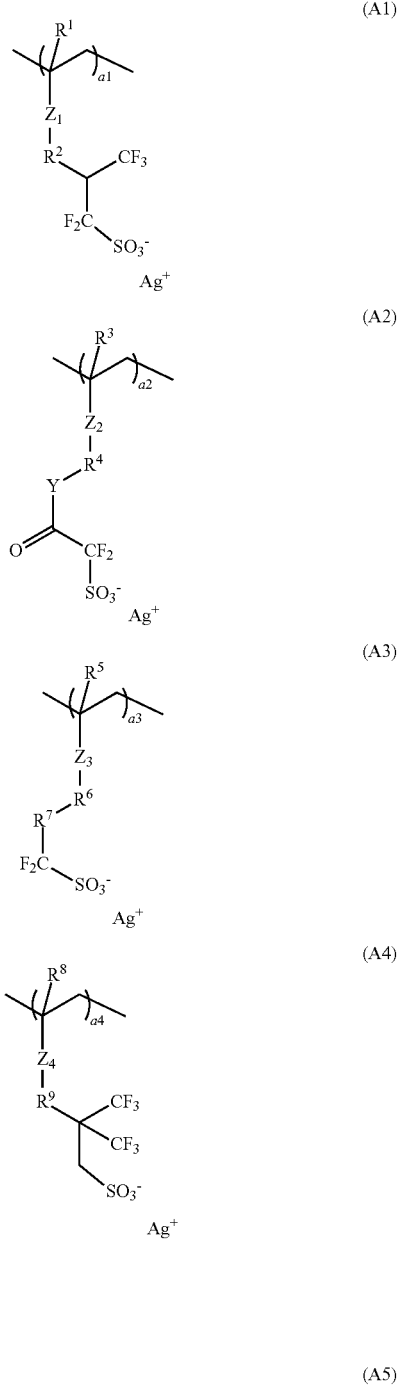

(A6)

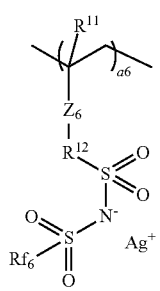

(A7)

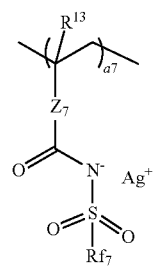

(3)

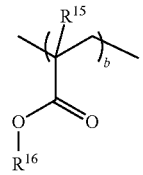

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 12 carbon atoms optionally having either or both of an ether group and an ester group; $R^7$ represents a linear or branched alkylene group having 1 to 4 carbon atoms, and one or two of the hydrogen atoms in $R^7$ are optionally substituted with a fluorine atom; $Z_1$, $Z_2$, $Z_3$, $Z_4$, and $Z_6$ each independently represent any of a single bond, a phenylene group, a naphthylene group, an ether group, an ester group, or an amide group; $Z_5$ represents any of a single bond, an ether group, or an ester group; $Z_7$ represents a single bond, an arylene group having 6 to 12 carbon atoms, or —C(=O)—O—$Z^8$—; and $Z^8$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $Z^8$; Y represents an oxygen atom or an —$NR^{14}$— group; $R^{14}$ represents a hydrogen atom, or a linear or branched alkyl group having 1 to 4 carbon atoms, optionally bonded to $R^4$ to form a ring; a1, a2, a3, a4, a5, a6, and a7 satisfy 0≤a1≤1.0, 0≤a2≤1.0, 0≤a3≤1.0, 0≤a4≤1.0, 0≤a5≤1.0, 0≤a6≤1.0, 0≤a7≤1.0, and 0≤a1+a2+a3+a4+a5a6+a7≤1.0; and $Rf_5$, $Rf_6$, and $Rf_7$ each represent a fluorine atom, or a linear or branched alkyl group having 1 to 4 carbon atoms, provided that one or more fluorine atoms are contained; and "m" is an integer of 1 to 4.

Having a repeating unit like this, the inventive bio-electrode composition can form a living body contact layer for a bio-electrode with particularly excellent electric conductivity and biocompatibility as well as light weight, which can be manufactured at low cost and does not cause large lowering of the electric conductivity even when it is wetted with water or dried.

It is preferable that the polymer compound be a copolymer that also has a repeating unit B having (meth)acrylate shown by the following general formula (3), wherein $R^{15}$ represents a hydrogen atom or a methyl group; $R^{16}$ represents a linear, branched, or cyclic alkyl group having 1 to 30 carbon atoms, a linear, branched, or cyclic alkenyl group having 2 to 30 carbon atoms, or a linear, branched, or cyclic alkynyl group having 2 to 30 carbon atoms; and "b" satisfies 0≤b<1.0.

Having the repeating unit B like this, the bio-electrode composition enhances the tackiness.

It is preferable that the polymer compound be a copolymer that also has at least one of a repeating unit C having a fluorine atom or a silicon atom and a repeating unit D having one or more groups selected from the group consisting of a hydroxy group, a carboxy group, an oxirane group, and an oxetane group.

Having the repeating unit C and/or like these, the bio-electrode composition is particularly excellent in water repellency and crosslinkability.

It is preferable that the bio-electrode composition further comprise a carbon material; an ITO particle; powder of a metal selected from silver, gold, platinum, copper, and nickel; or a particle coated with a metal selected from silver, gold, platinum, copper, and nickel.

Such a bio-electrode composition can form a living body contact layer that has more favorable electric conductivity.

It is preferable that the carbon material be either or both of carbon black and carbon nanotube.

Such a carbon material can be particularly preferably used in the inventive bio-electrode composition.

The present invention also provides a bio-electrode comprising an electro-conductive base material and a living body contact layer formed on the electro-conductive base material;

wherein the living body contact layer is a cured material of the foregoing bio-electrode composition.

The inventive bio-electrode has excellent electric conductivity and biocompatibility as well as light weight, which can be manufactured at low cost and does not cause large lowering of the electric conductivity even when it is wetted with water or dried.

It is preferable that the electro-conductive base material comprises one or more species selected from gold, silver, silver chloride, platinum, aluminum, magnesium, tin, tungsten, iron, copper, nickel, stainless, chromium, titanium, and carbon.

Such an electro-conductive base material can be particularly preferably used in the inventive bio-electrode.

The present invention also provides a method for manufacturing a bio-electrode having an electro-conductive base material and a living body contact layer formed on the electro-conductive base material, comprising:

applying the foregoing bio-electrode composition onto the electro-conductive base material; and curing the bio-electrode composition; thereby forming the living body contact layer.

The inventive production method for manufacturing a bio-electrode makes it possible to manufacture a bio-electrode easily and at low cost, which is excellent in electric conductivity and biocompatibility as well as light weight without causing large lowering of the electric conductivity even when it is wetted with water or dried.

It is preferable that the electro-conductive base material comprise one or more species selected from gold, silver, silver chloride, platinum, aluminum, magnesium, tin, tungsten, iron, copper, nickel, stainless, chromium, titanium, and carbon.

Such an electro-conductive base material can be particularly preferably used in the inventive method for manufacturing a bio-electrode.

Advantageous Effects of Invention

As described above, the inventive bio-electrode composition can form a living body contact layer that can efficiently conduct electric signals from skin to a device (i.e., having excellent electric conductivity), is free from the risk of causing allergies even when it is worn on skin for a long time (i.e., having excellent biocompatibility), is light in weight, can be manufactured at low cost, and does not cause lowering of the electric conductivity even when it is wetted with water or dried. The electric conductivity can be further improved by adding carbon material, metal coated particles, or ITO particles. In combination with a polymer compound having tackiness and elasticity, it is also possible to manufacture a bio-electrode that has particularly high tackiness and elasticity. Accordingly, the bio-electrode, the living body contact layer of which is formed by using the inventive bio-electrode composition described above, is particularly suitable as a bio-electrode used for a medical wearable device. Moreover, the inventive method for manufacturing a bio-electrode can manufacture such a bio-electrode easily at low cost.

DESCRIPTION OF EMBODIMENTS

Figure 1:
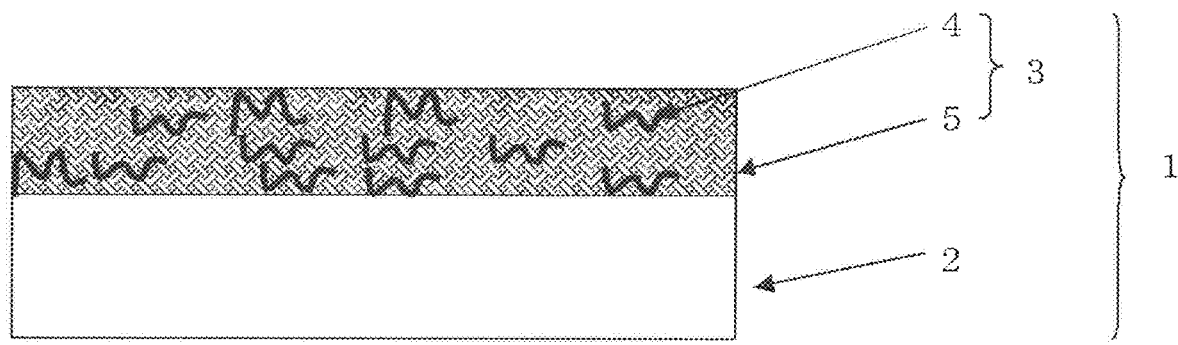
FIG. 1 is a schematic sectional view showing an example of the inventive bio-electrode.

As described above, it has been desired to develop a bio-electrode composition that can form a living body contact layer for a bio-electrode with excellent electric conductivity and biocompatibility as well as light weight, which can be manufactured at low cost and does not cause large lowering of the electric conductivity even when it is wetted with water or dried; a bio-electrode in which the living body contact layer is formed from the bio-electrode composition; and a method for manufacturing the same.

As an ionic liquid to be blended to a bio-electrode composition for forming a living body contact layer for a bio-electrode, alkali metal salt such as sodium salt and potassium salt as well as ammonium salt of fluorosulfonic acid or bisfluorosulfonylmidic acid have been generally known. These salts are generally liable to hydrate, thereby being extracted with perspiration or by washing from a bio-electrode in which the living body contact layer is formed from a bio-electrode composition using these salts, making the bio-electrode lower the electric conductivity. Additionally, in contact with skin, an ionic liquid with lower molecular weight involves higher risk of permeating the skin to cause allergies.

On the other hand, a polymeric type ionic compound does not penetrate skin, thereby decreasing the risk of causing skin allergies. As a polymer type fluorosulfonic acid, a copolymer of tetrafluoroethylene and perfluoro-[2-(fluorosulfonylethoxy)propyl vinyl ether] (registered trade mark; Nafion) have been known. This copolymer is highly proton transportable and has been investigated for fuel cells. However, Nafion is highly acidic and highly irritate to skin even in a state of the neutralized sodium salt, potassium salt, or ammonium salt thereof. Nafion lacks a tack function and is problematic to be applied for a bio-electrode in this point of view.

It has also been proposed an antifungal composition using a polymer copolymerized with methide acid (Japanese Unexamined Patent Application Publication No. 2012-92088). The methide acid is, however, highly acidic as Nafion such that a fungus or a bacterium is extinct, and is problematic to be applied for a bio-electrode. On the other hand, bio-electrodes using sodium salts of polymethacrylic acid and so on show lower electric conductivity. In order to obtain high ion conductivity, a neutral salt of a highly acidic acid is necessary. Accordingly, it is necessary to develop a material that is satisfactory in both acidity and biocompatibility.

The present inventors have diligently investigated to solve the foregoing subject and have conceived that the bio-electrode using a polymer of silver salt of partially fluorinated sulfonic acid, fluorosulfonimidio acid, or fluorosulfonamic acid is scarcely soluble to water, thereby being free from the risk of extraction with perspiration that causes lowering of the electric conductivity and rough dry skin. The present inventors practically synthesized a monomer of silver salt of fluorosulfonic acid, fluorosulfonimidic acid, or fluorosulfonamic acid having a polymerizable double bond, and have revealed that the bio-electrode using a polymer obtained by polymerizing the monomer can combine electric conductivity and biocompatibility without changing the electric conductivity even when it is wetted or dried. The present inventors have also found that it is possible to obtain a bio-electrode that can be in contact with skin continually to obtain stable electric signals for a long time by using a polymer copolymerized with a monomer to give a repeating unit to add tackiness in addition to the monomers described above; thereby completing the present invention.

That is, the present invention is a bio-electrode composition comprising a polymer compound having a repeating unit A that contains silver salt of fluorosulfonic acid, silver salt of fluorosulfonimide, or silver salt of fluorosulfonamide.

Hereinafter, the present invention will be specifically described, but the present invention is not limited thereto.
<Bio-Electrode Composition>

The inventive bio-electrode composition contains a polymer compound having an ionic repeating unit A as a polymeric type ionic material having a tack function. Hereinafter, each component will be described further specifically.
[Polymer Compound]

The polymer compound in the inventive bio-electrode composition is a polymeric type salt to be blended as an electric conductive material, and has a repeating unit A that contains silver salt of fluorosulfonic acid, silver salt of fluorosulfonimide, or silver salt of fluorosulfonamide. Incidentally, the repeating unit A may include two or more kinds of silver salt.

The ionic repeating unit A preferably has a structure shown by the following general formula (1)-1, (1)-2, (1)-3, or (1)-4

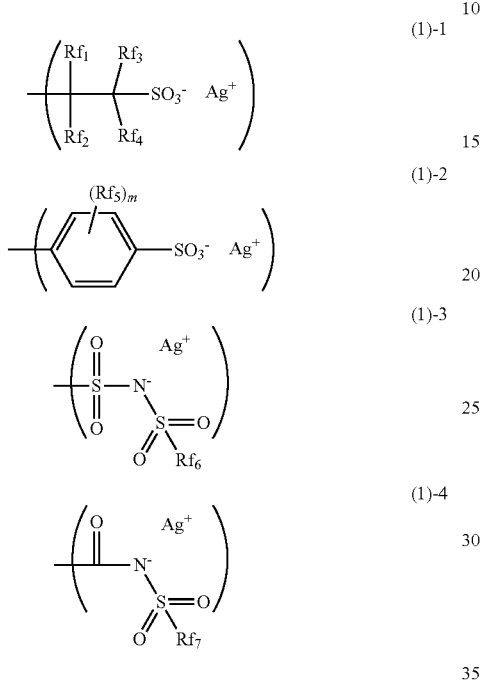

wherein $Rf_1$ and $Rf_2$ each represent a hydrogen atom, a fluorine atom, a trifluoromethyl group, or an oxygen atom, provided that when $Rf_1$ represents an oxygen atom, $Rf_2$ also represents the oxygen atom to form a carbonyl group together with a carbon atom bonded therewith; $Rf_3$ and $Rf_4$ each represent a hydrogen atom, a fluorine atom, or a trifluoromethyl group, provided that one or more fluorine atoms are contained in $Rf_1$ to $Rf_4$; $Rf_5$, $Rf_6$, and $Rf_7$ each represent a fluorine atom, or a linear or branched alkyl group having 1 to 4 carbon atoms, provided that one or more fluorine atoms are contained; and "m" is an integer of 1 to 4.

This repeating unit A is more preferably one or more repeating units selected from repeating units A1 to A7 shown by the following general formula (2), (2)

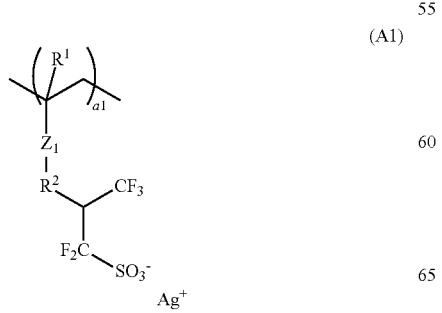
(A1)

-continued

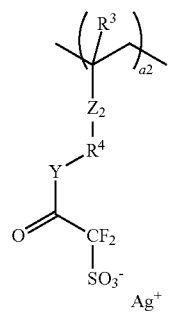
(A2)

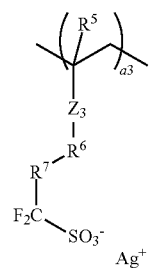
(A3)

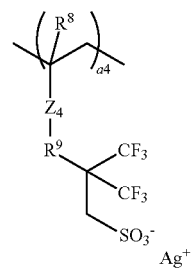
(A4)

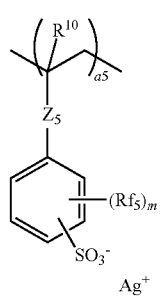
(A5)

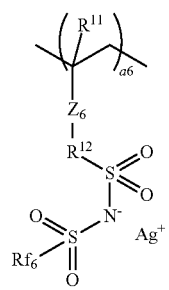
(A6)

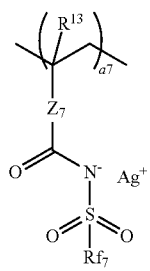
(A7)

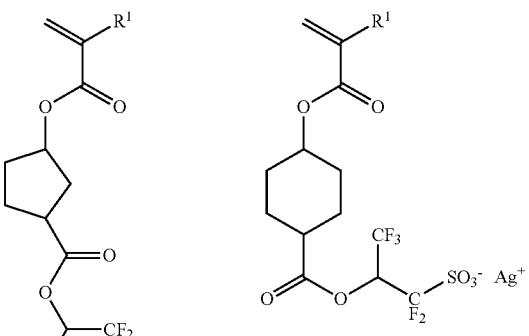

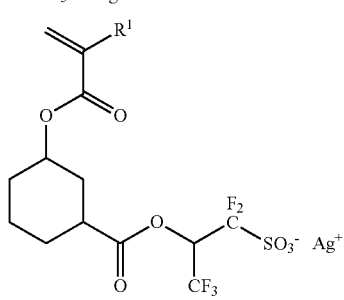

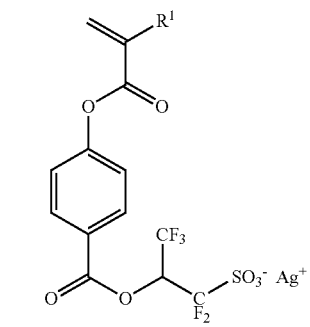

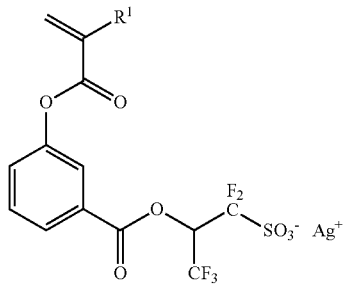

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 12 carbon atoms optionally having either or both of an ether group and an ester group; $R^7$ represents a linear or branched alkylene group having 1 to 4 carbon atoms, and one or two of the hydrogen atoms in $R^7$ are optionally replaced with a fluorine atom; $Z_1$, $Z_2$, $Z_3$, $Z_4$, and $Z_6$ each independently represent any of a single bond, a phenylene group, a naphthylene group, an ether group, an ester group, or an amide group; $Z_5$ represents any of a single bond, an ether group, or an ester group; $Z_7$ represents a single bond, an arylene group having 6 to 12 carbon atoms, or $-C(=O)-O-Z^8-$; and $Z^8$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $Z^8$; Y represents an oxygen atom or an $-NR^{14}-$ group; $R^{14}$ represents a hydrogen atom, or a linear or branched alkyl group having 1 to 4 carbon atoms, optionally bonded to $R^4$ to form a ring; a1, a2, a3, a4, a5, a6, and a7 satisfy $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, and $0 < a1+a2+a3+a4+a5+a6+a7 \leq 1.0$; and $Rf_5$, $Rf_6$, and $Rf_7$ each represent a fluorine atom, or a linear or branched alkyl group having 1 to 4 carbon atoms, provided that one or more fluorine atoms are contained; and "m" is an integer of 1 to 4.

Illustrative examples of the fluorosulfonate monomer (monomer of salt of fluorosulfonic acid) to give any of the repeating units A1 to A5 among the repeating units A1 to A7 shown by the general formula (2) include the following.

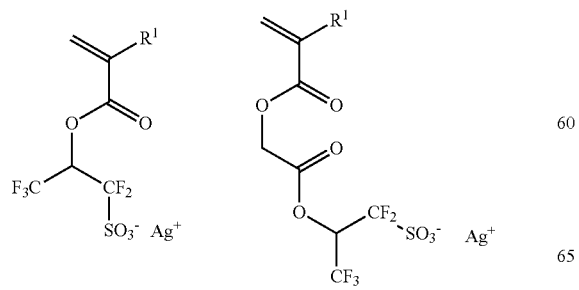

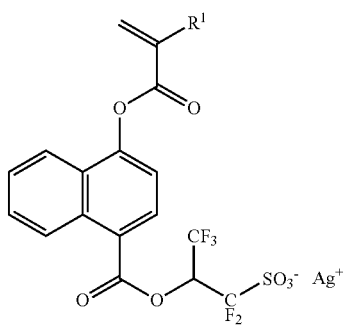

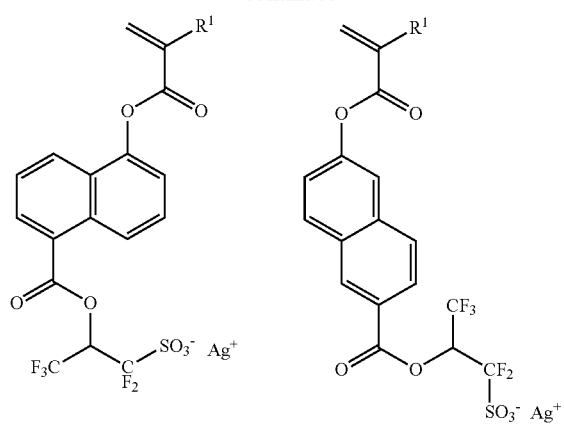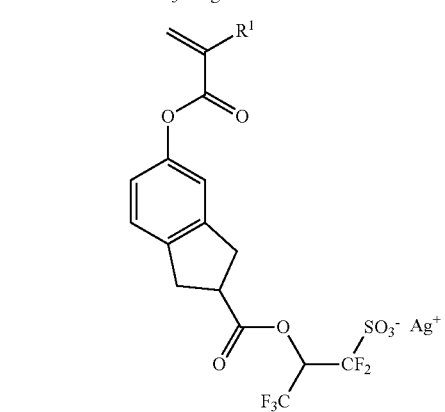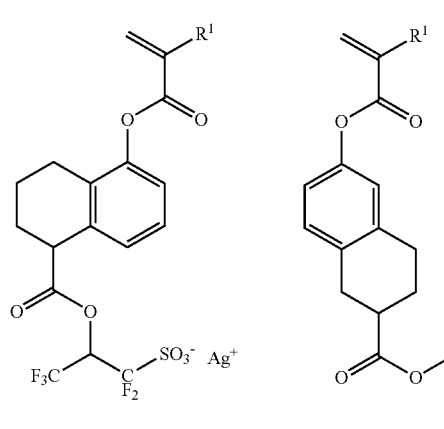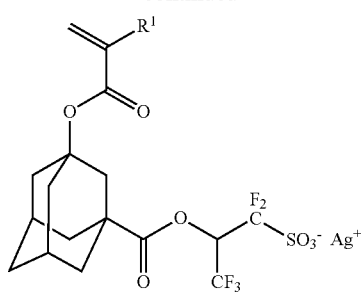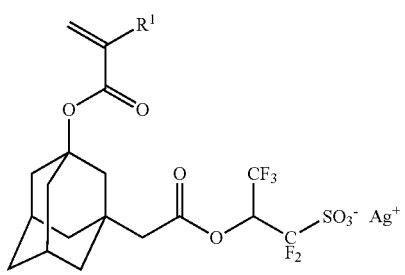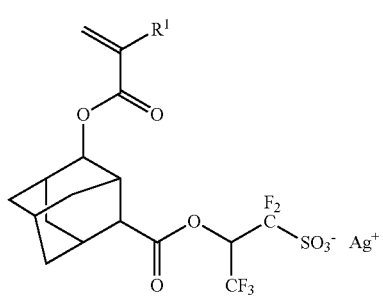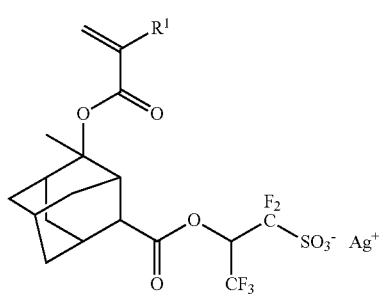

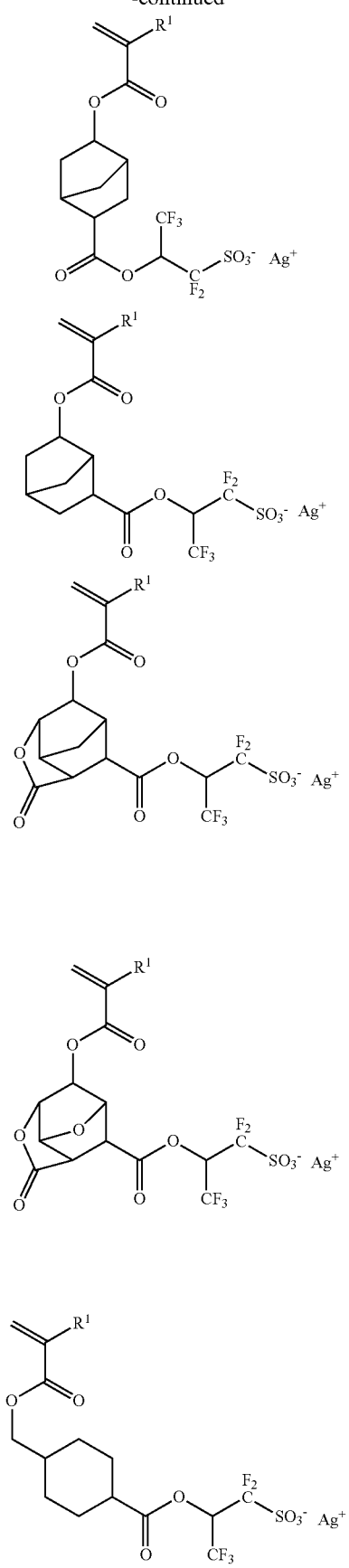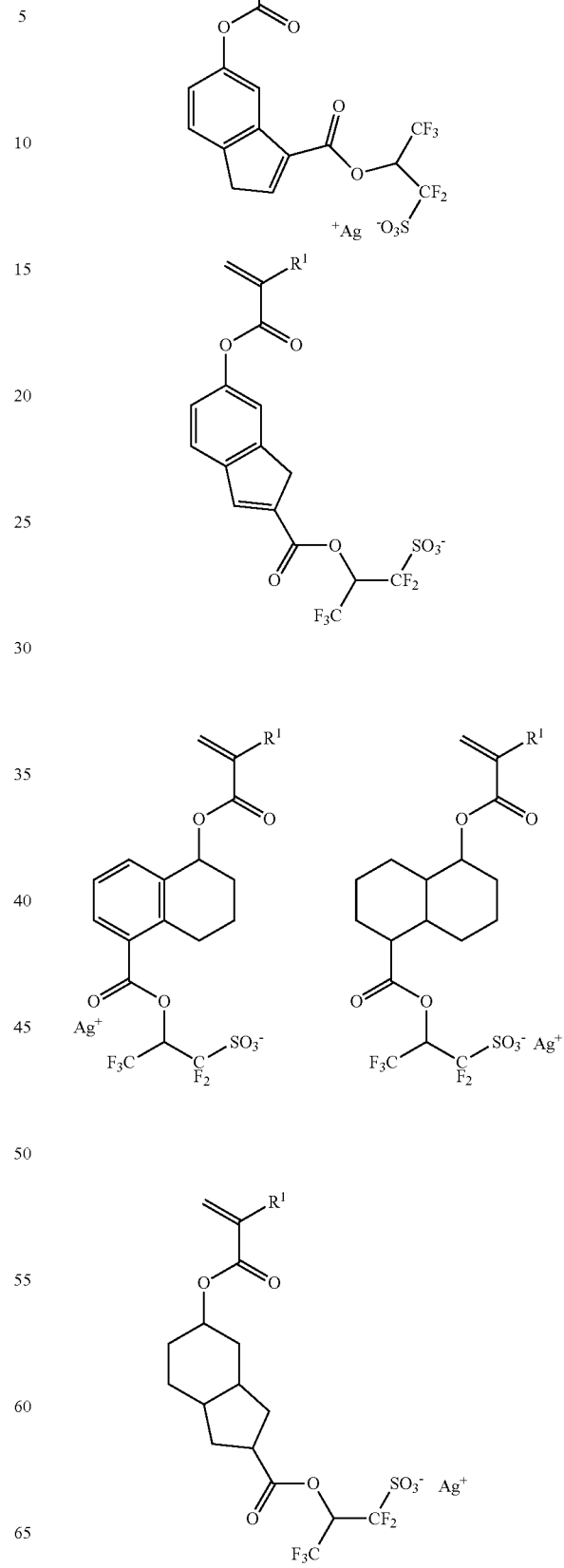

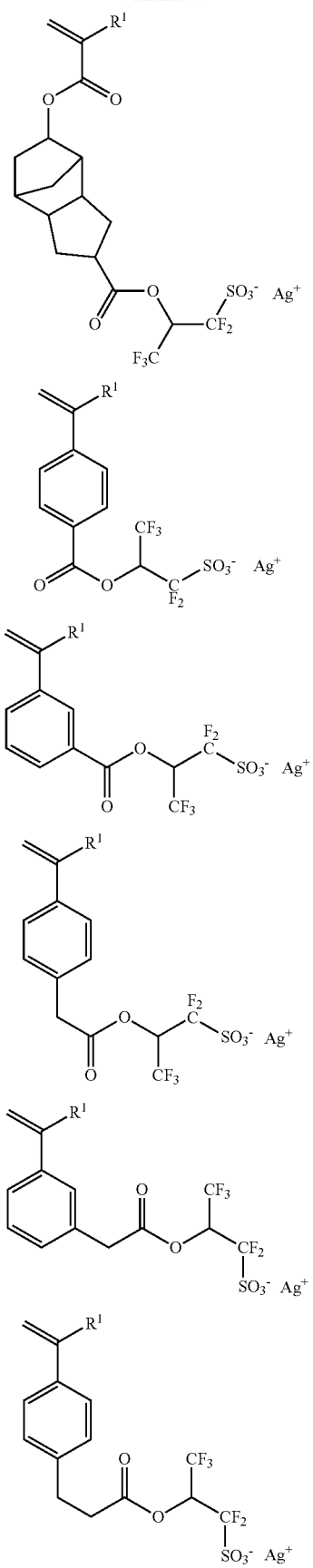
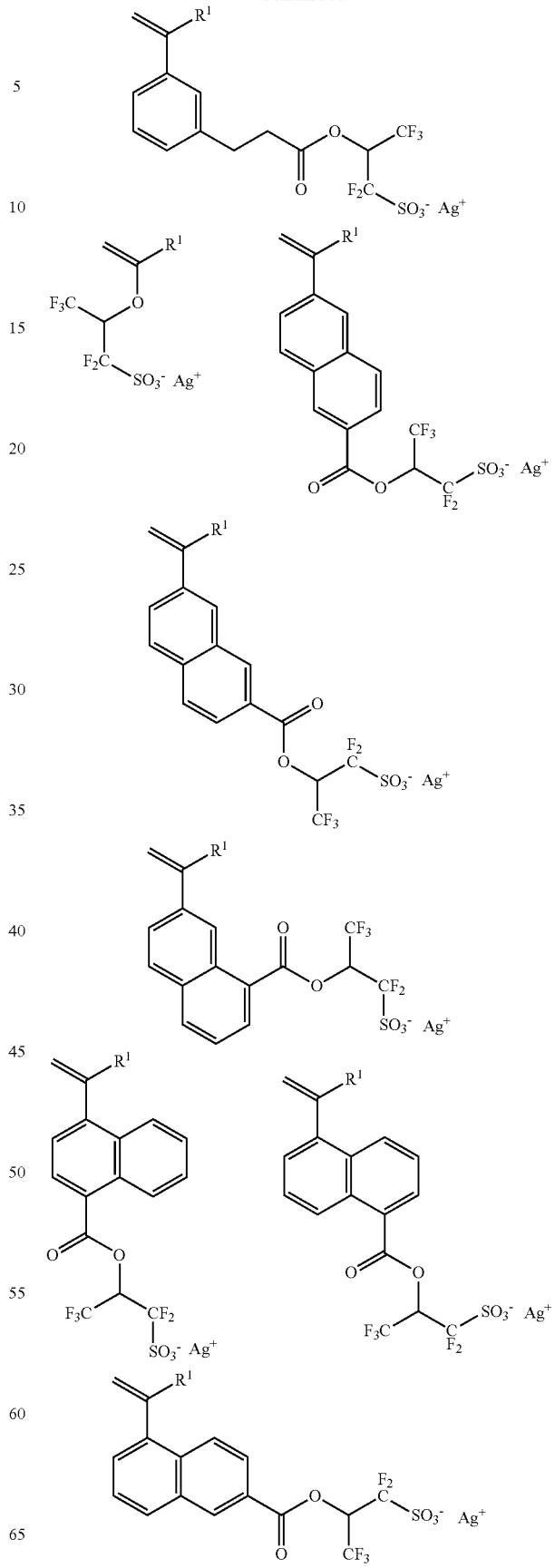

-continued
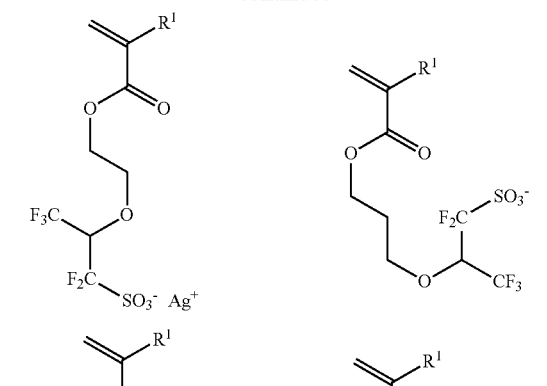
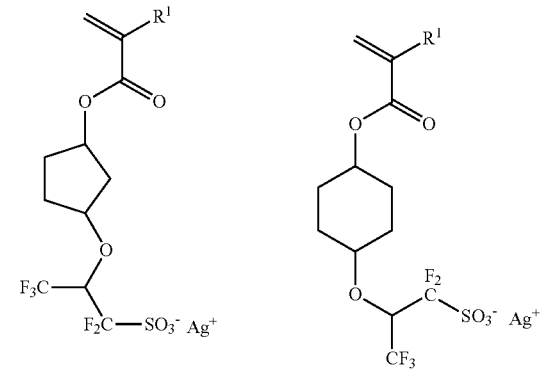
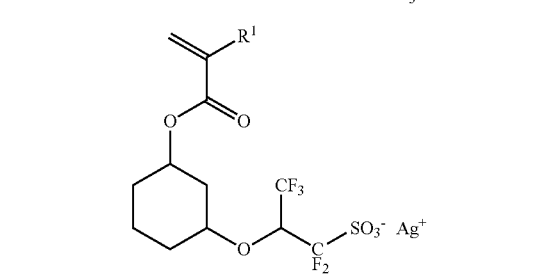
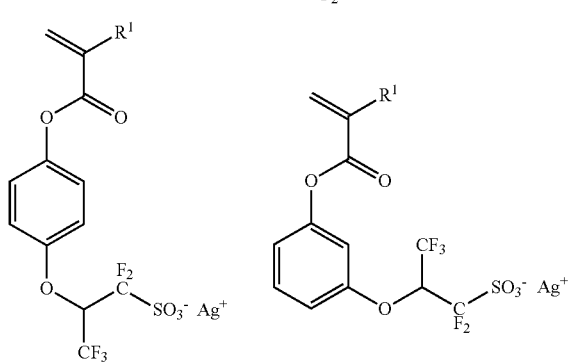
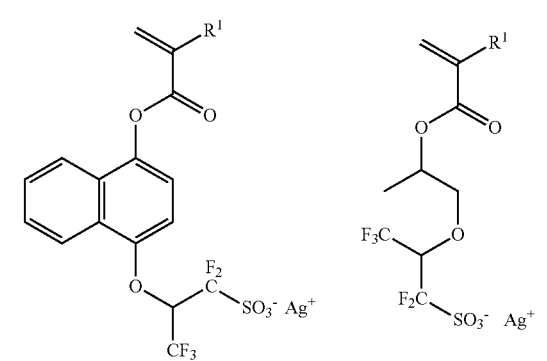
-continued
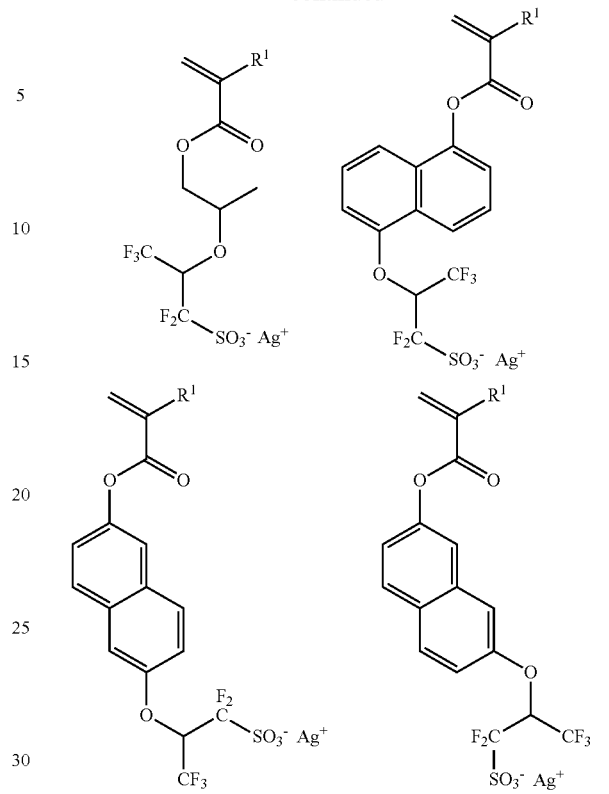
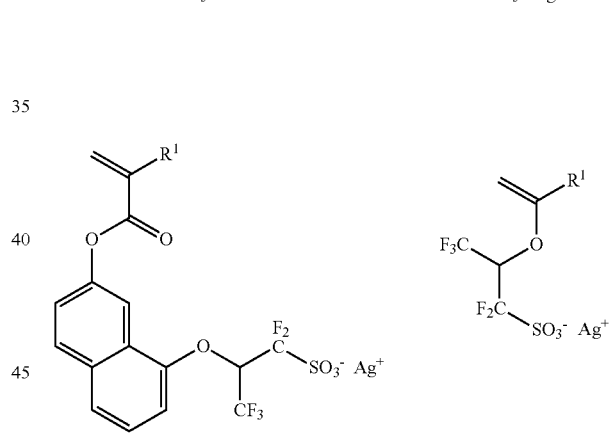
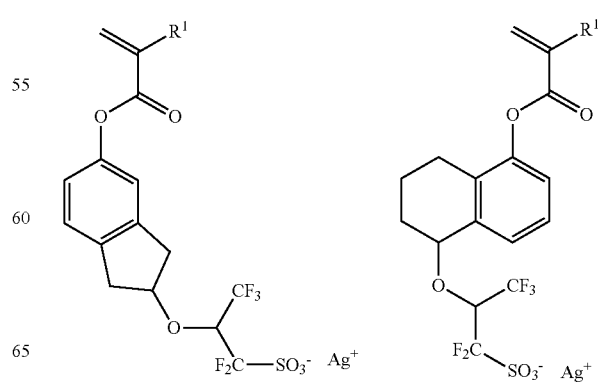

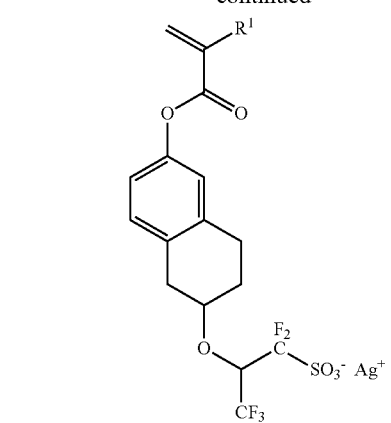
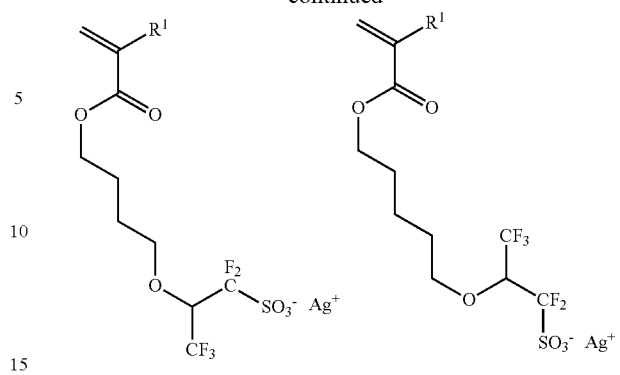
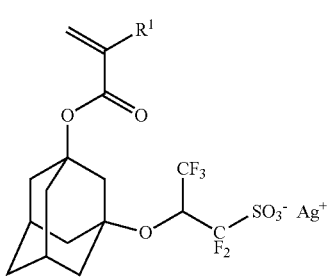
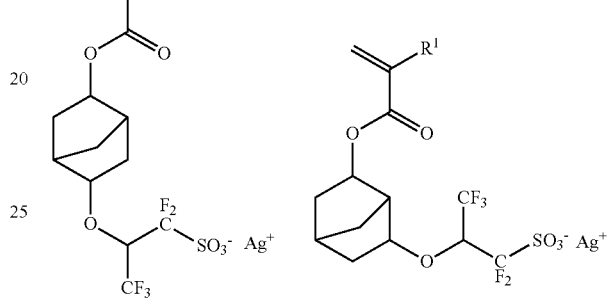
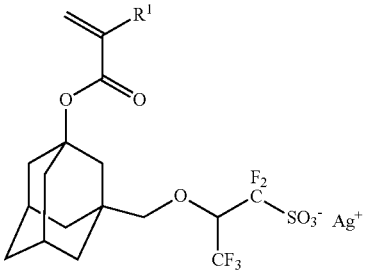
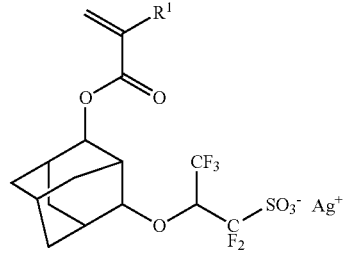
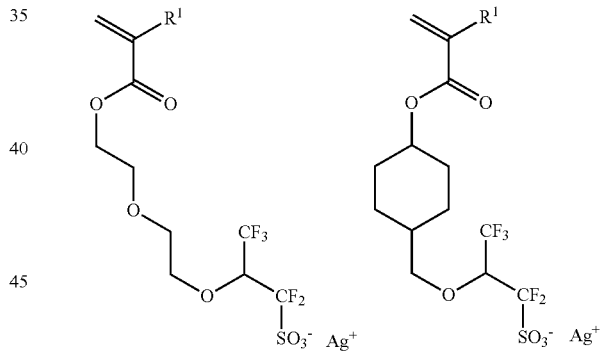
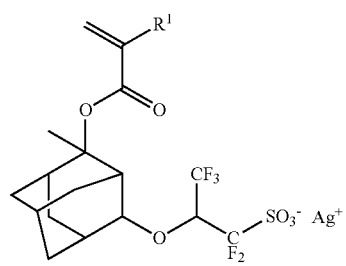
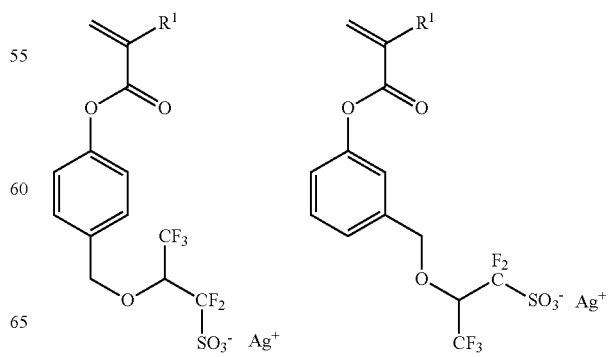

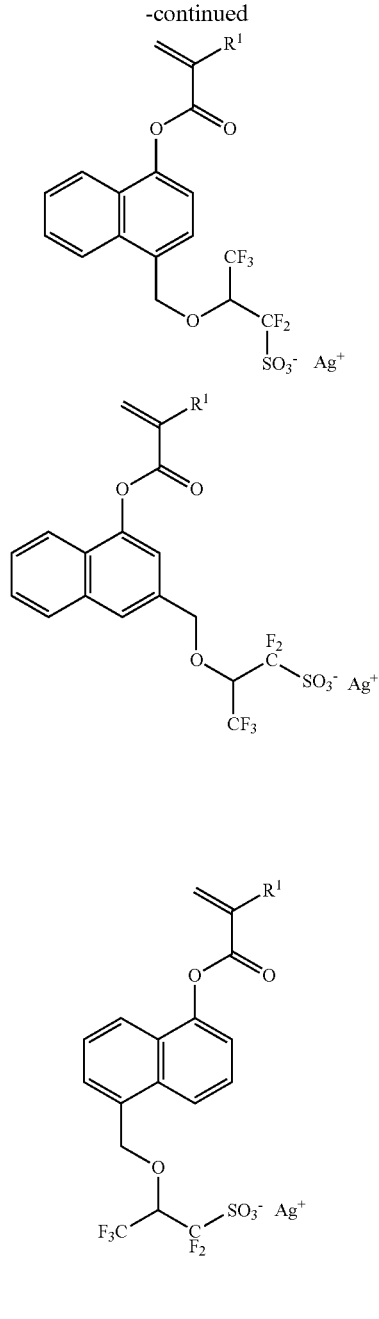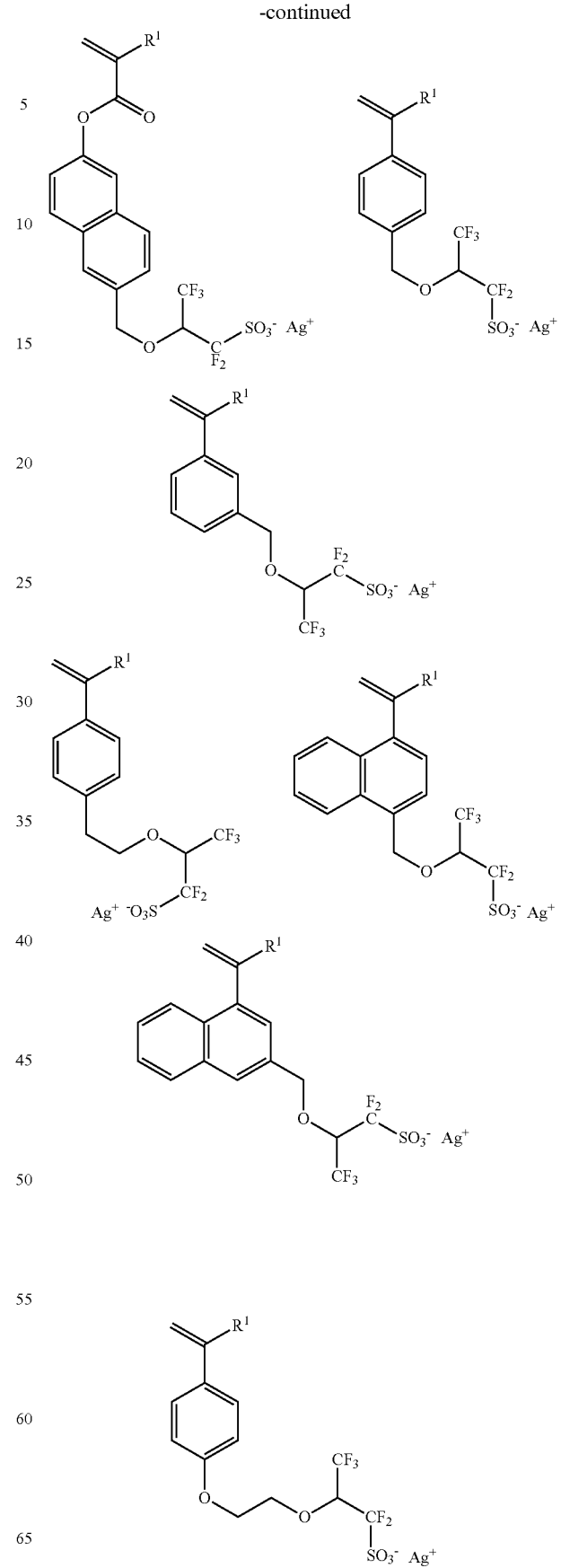

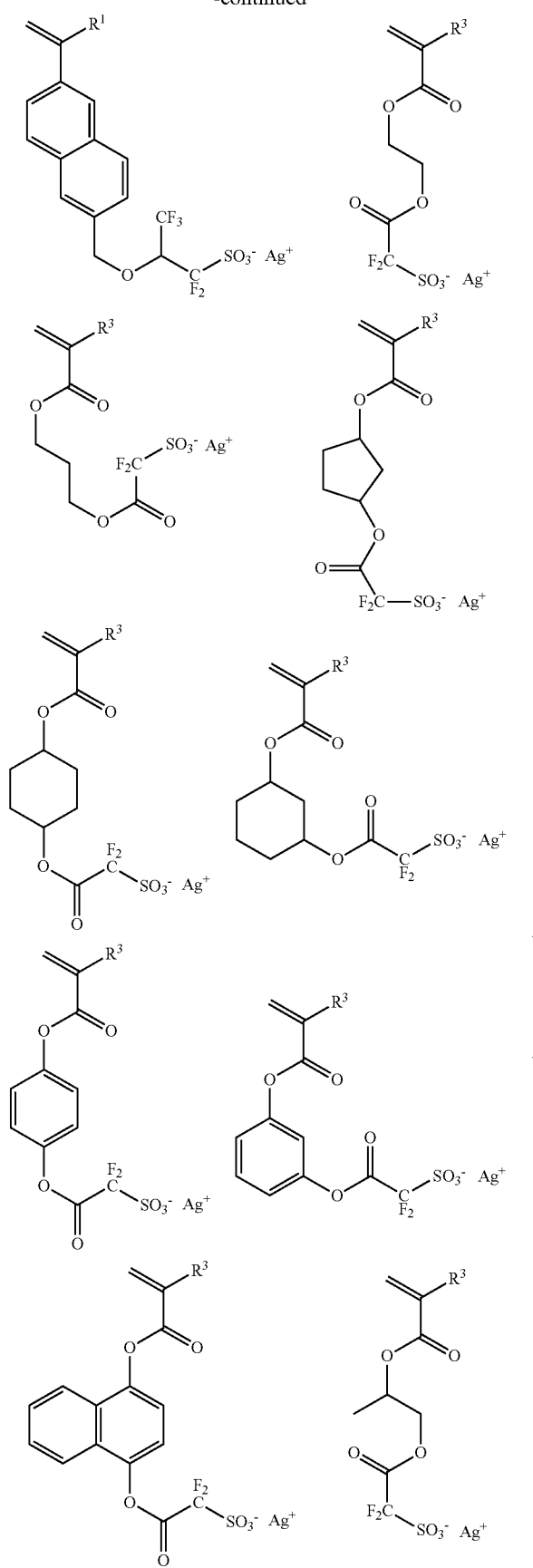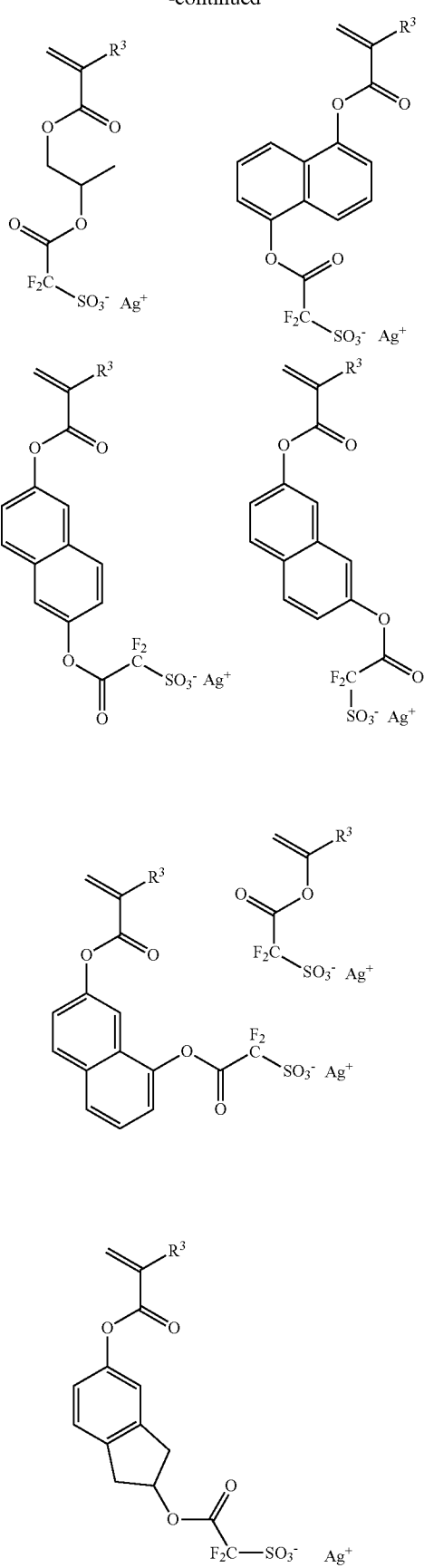

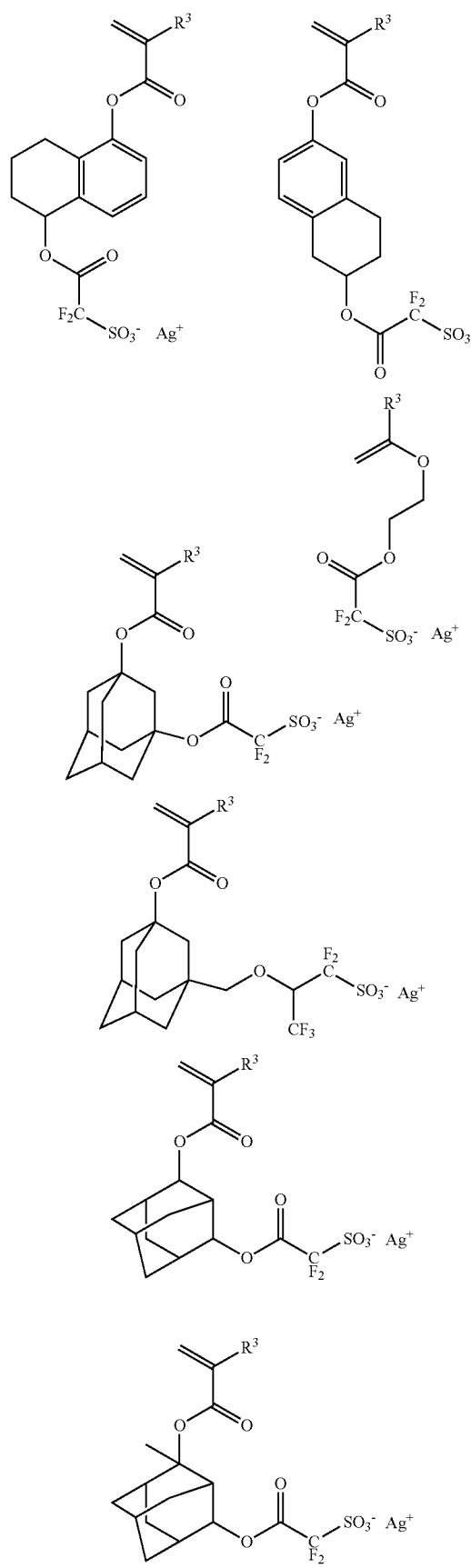
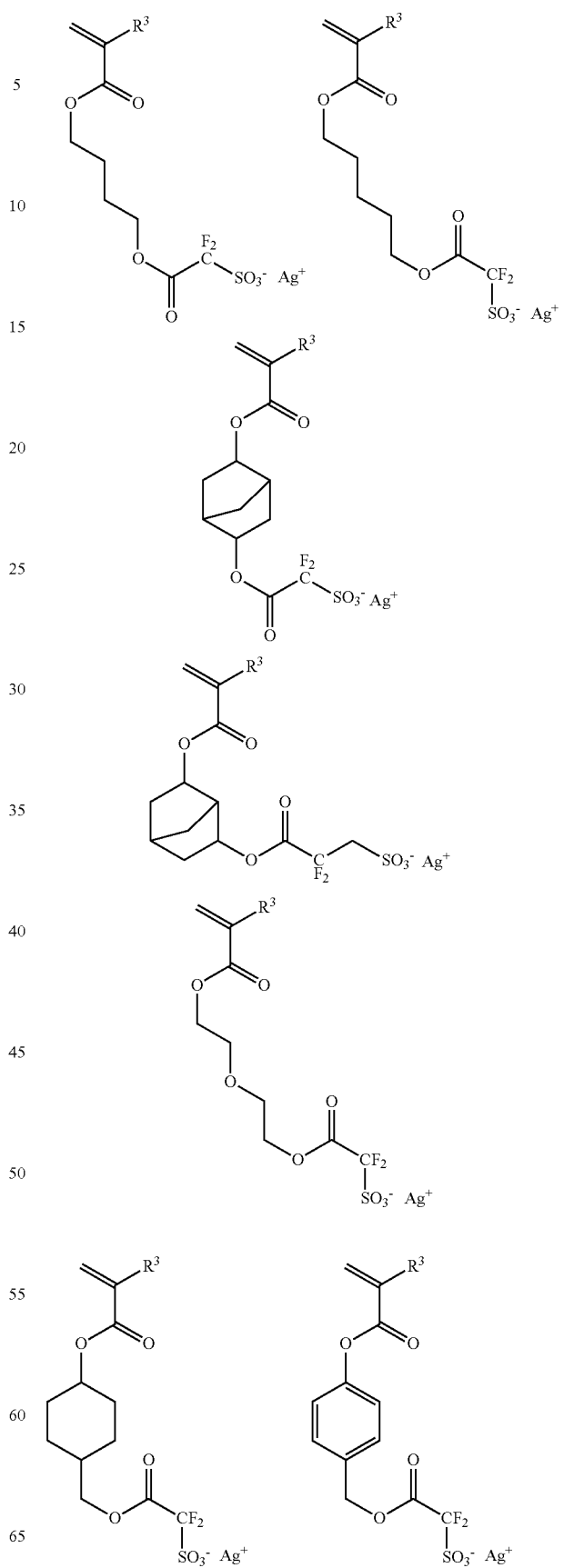

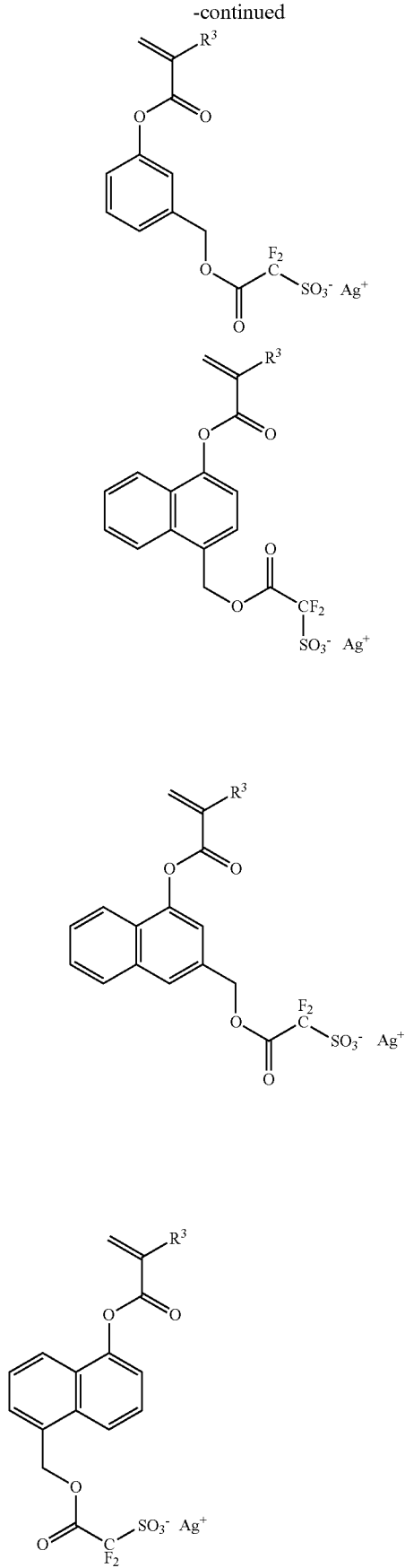

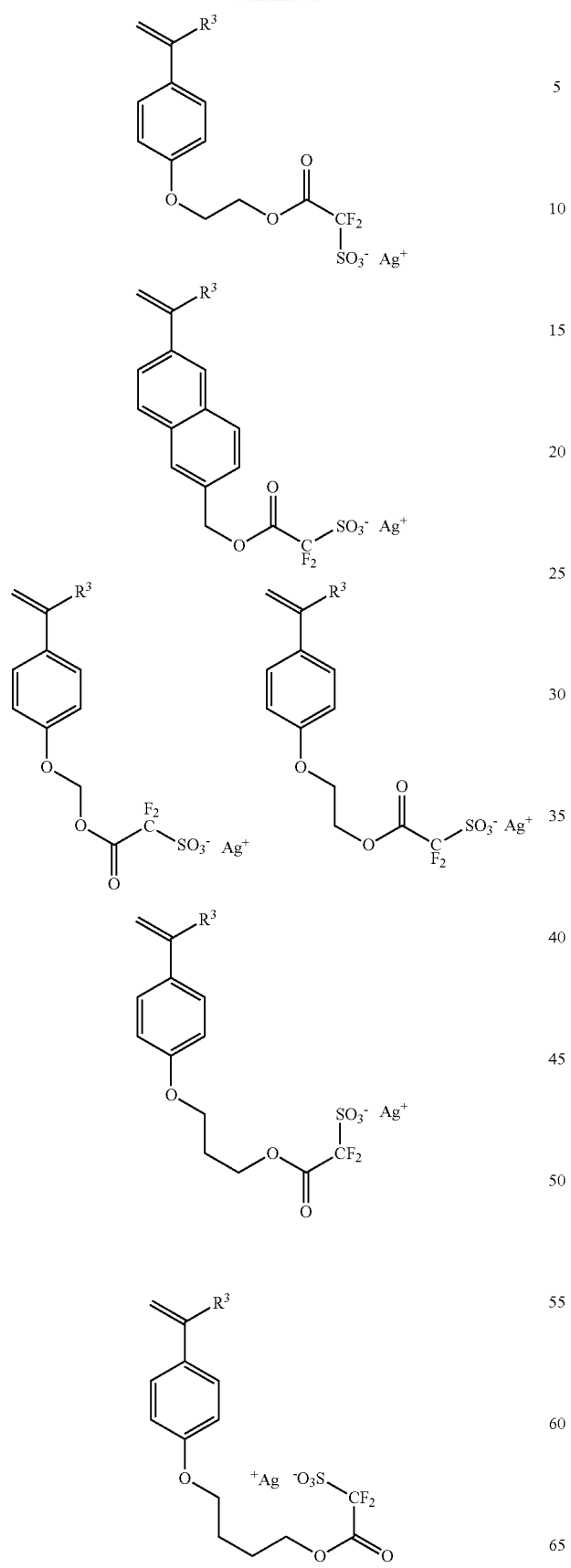

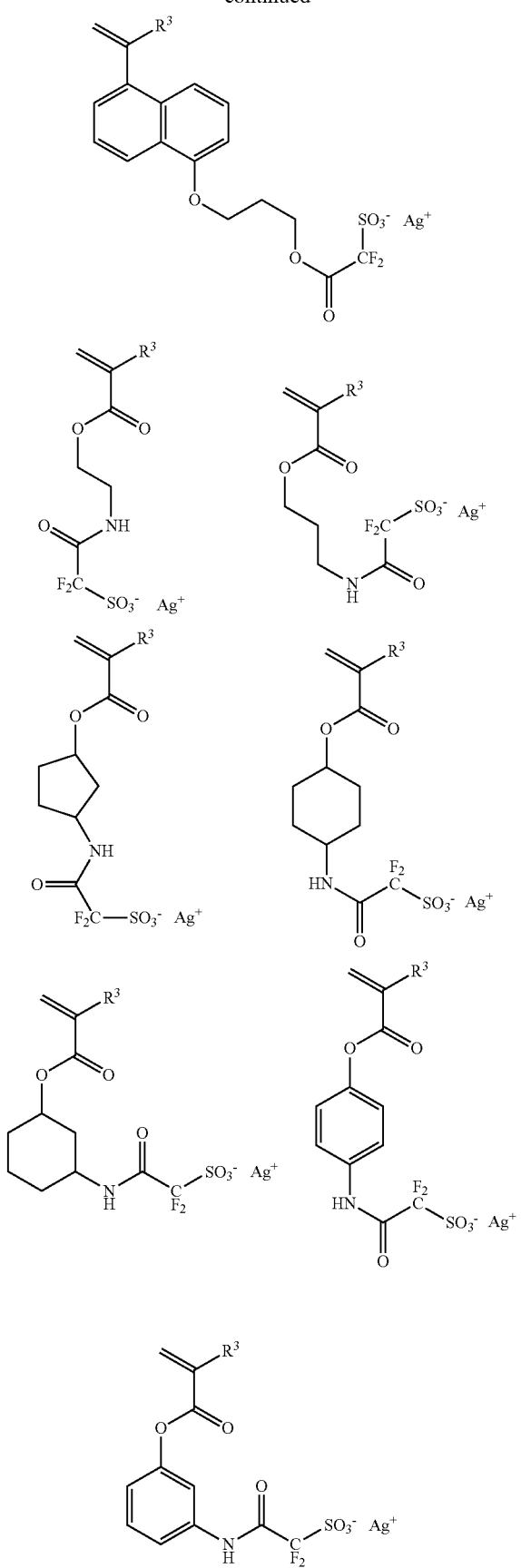
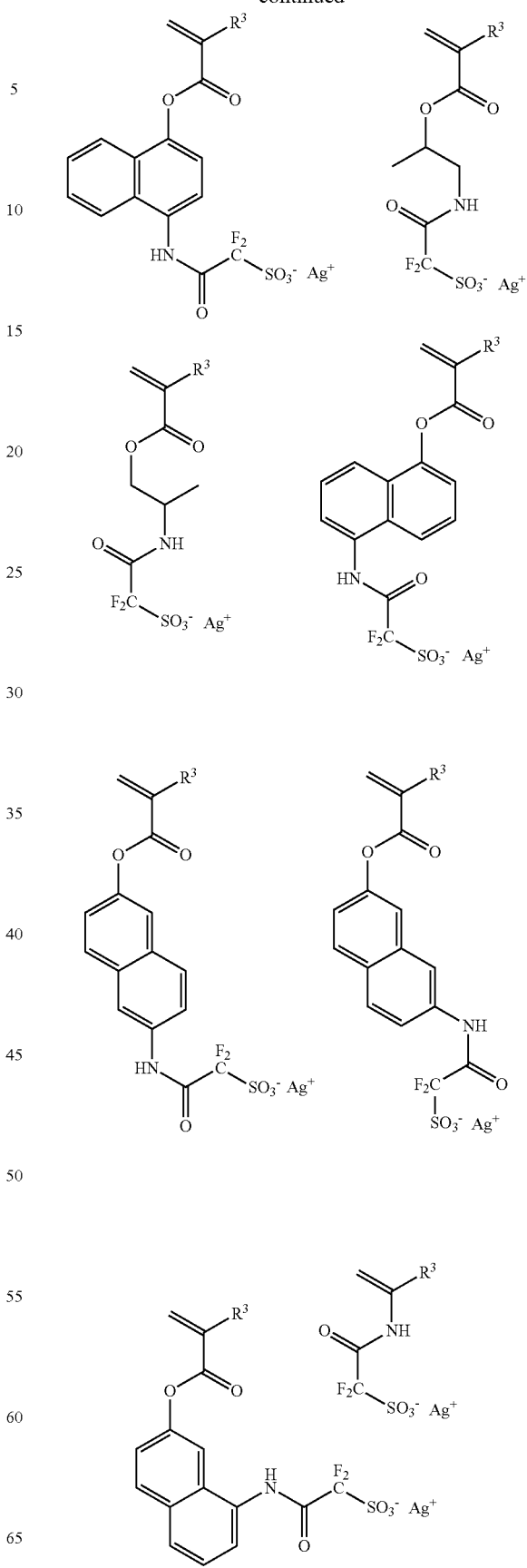

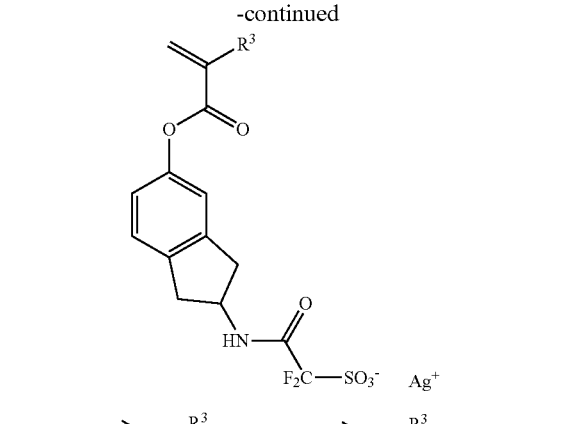
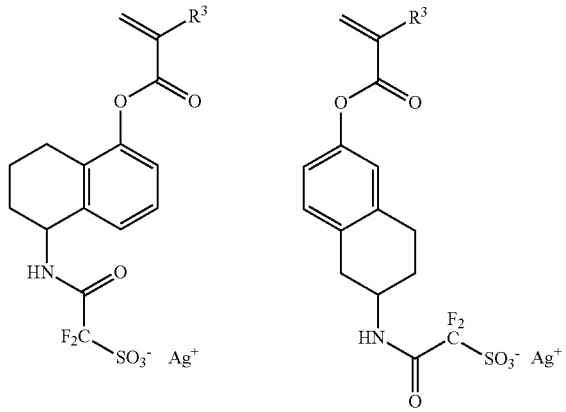
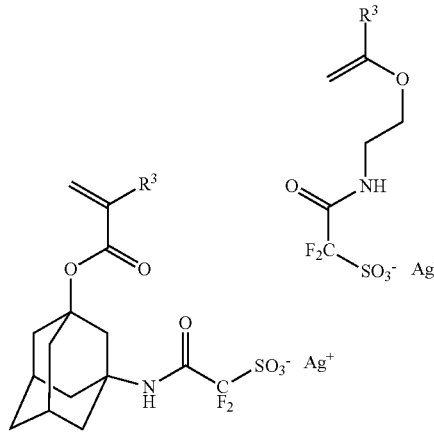
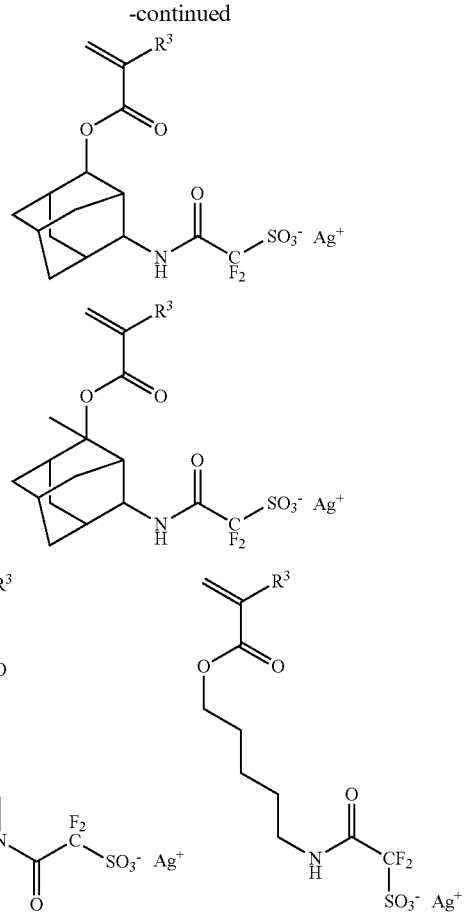
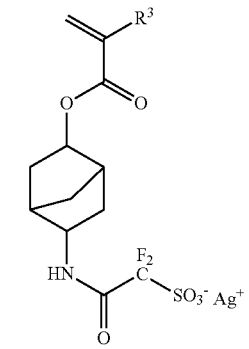
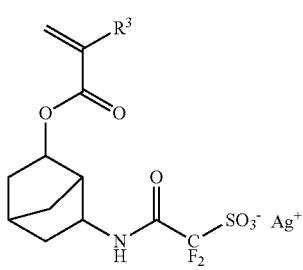

37
-continued
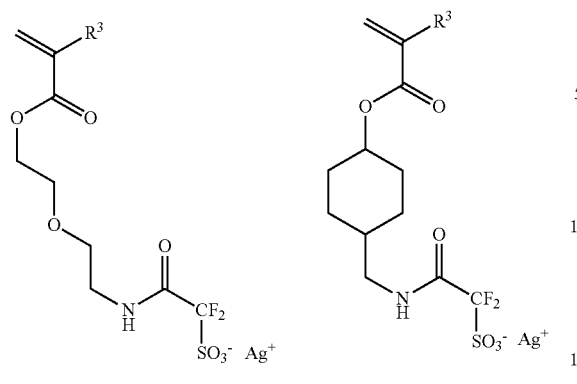
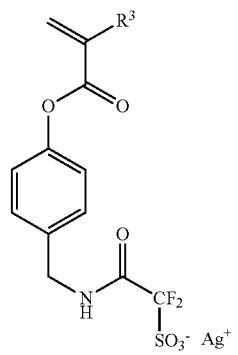
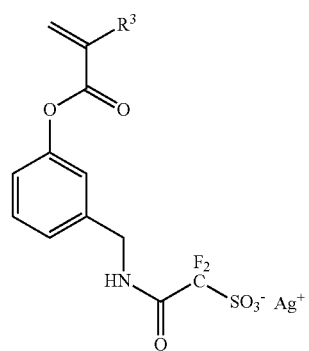
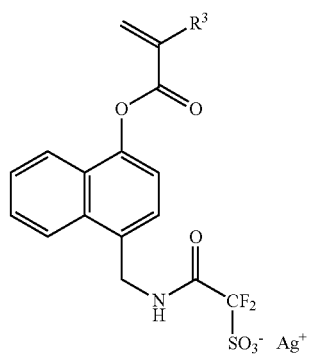
38
-continued
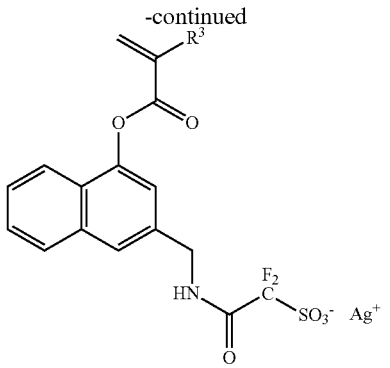
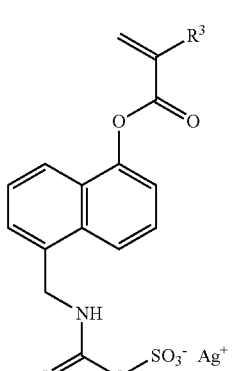
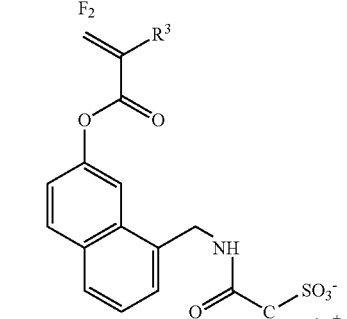
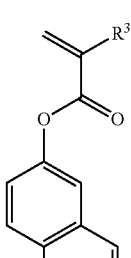
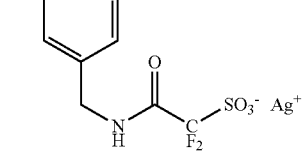
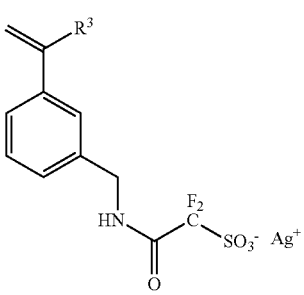

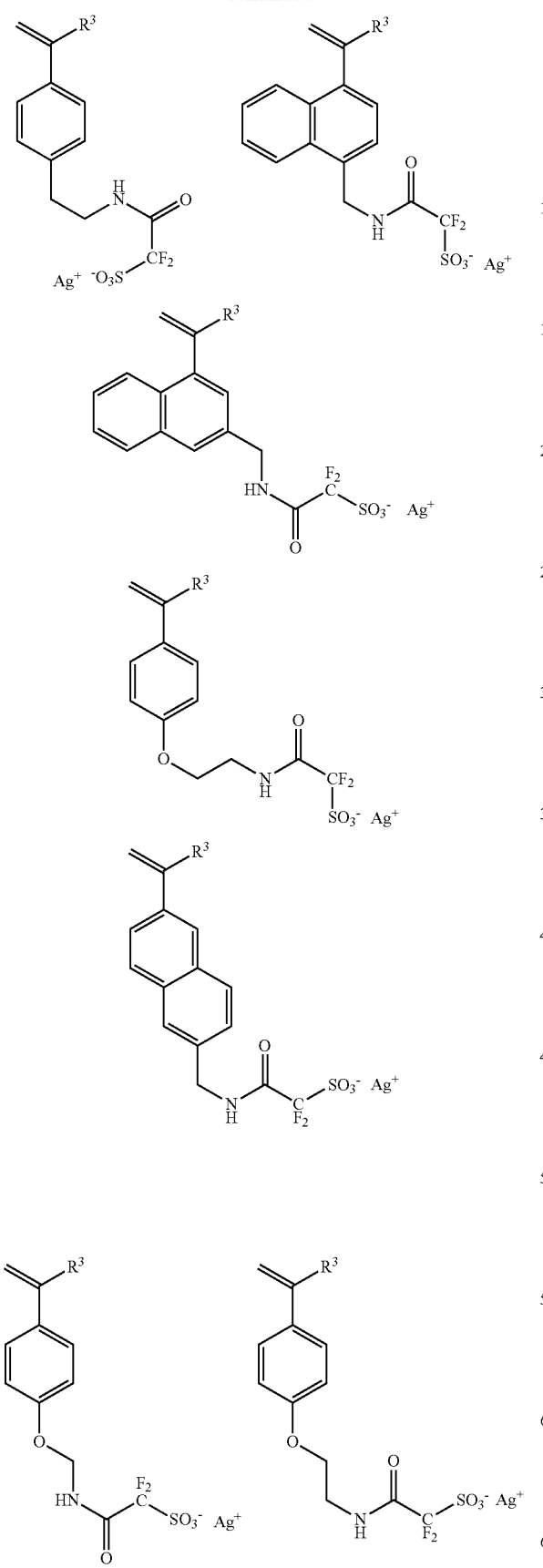
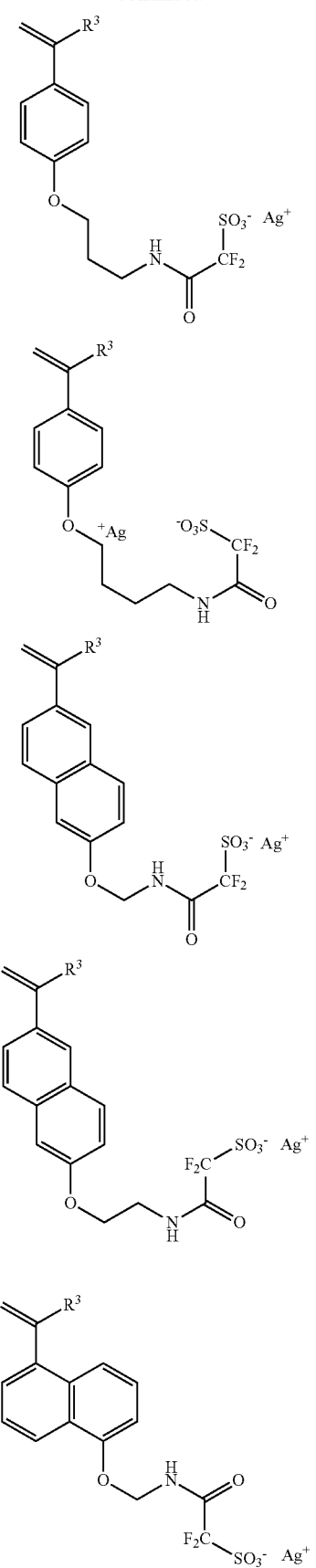

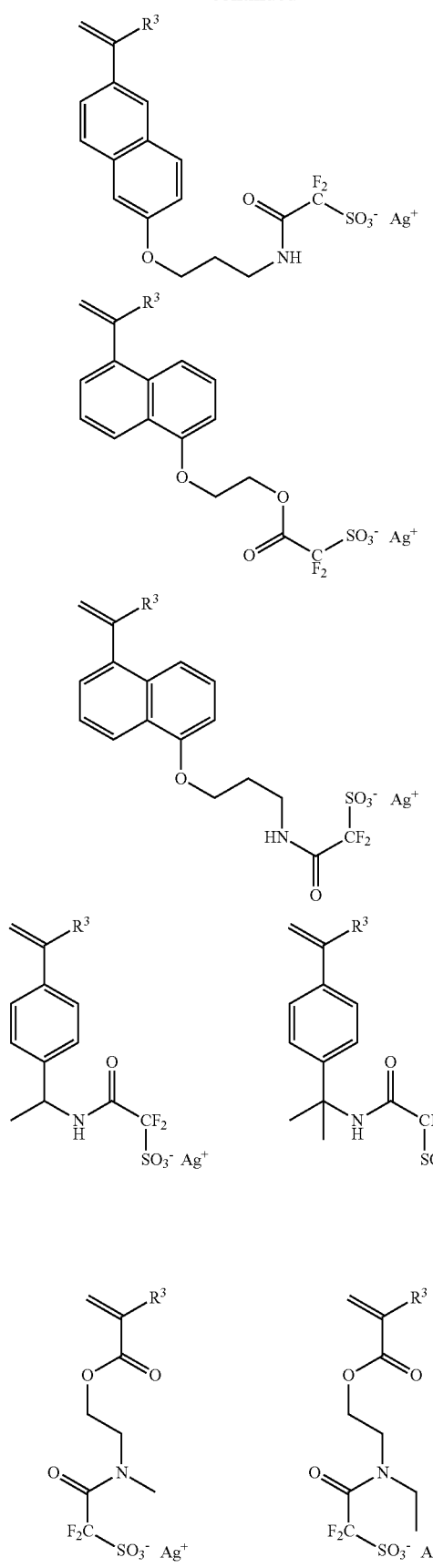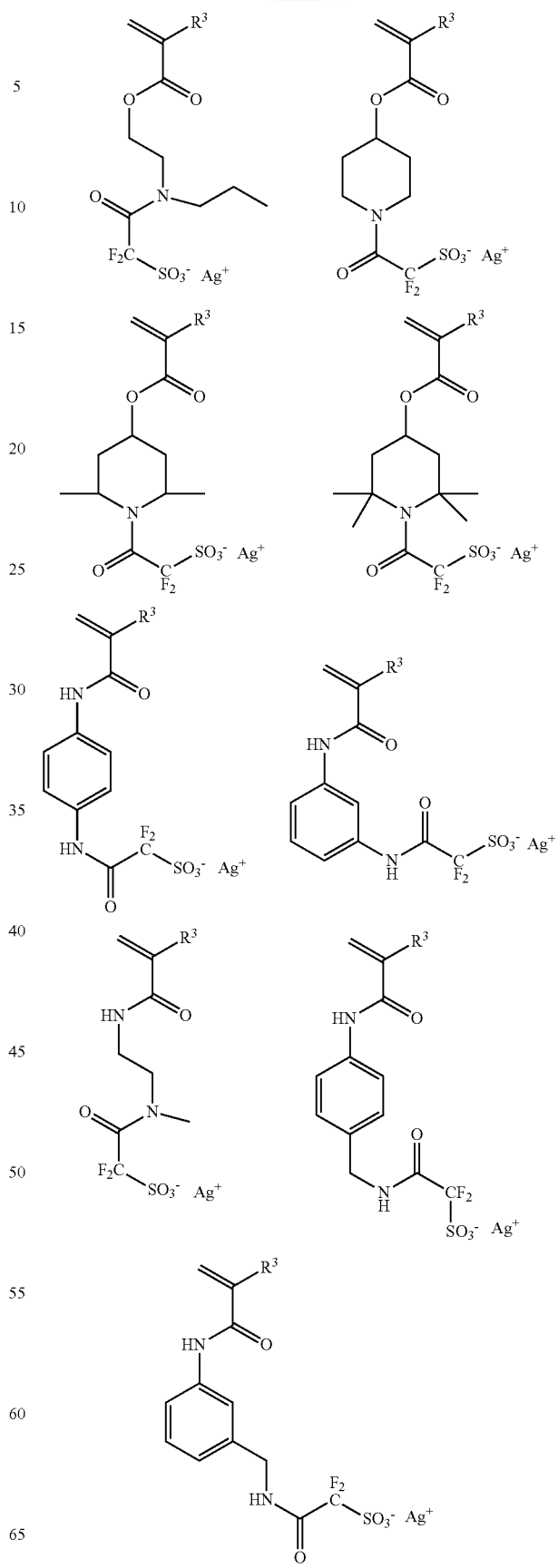

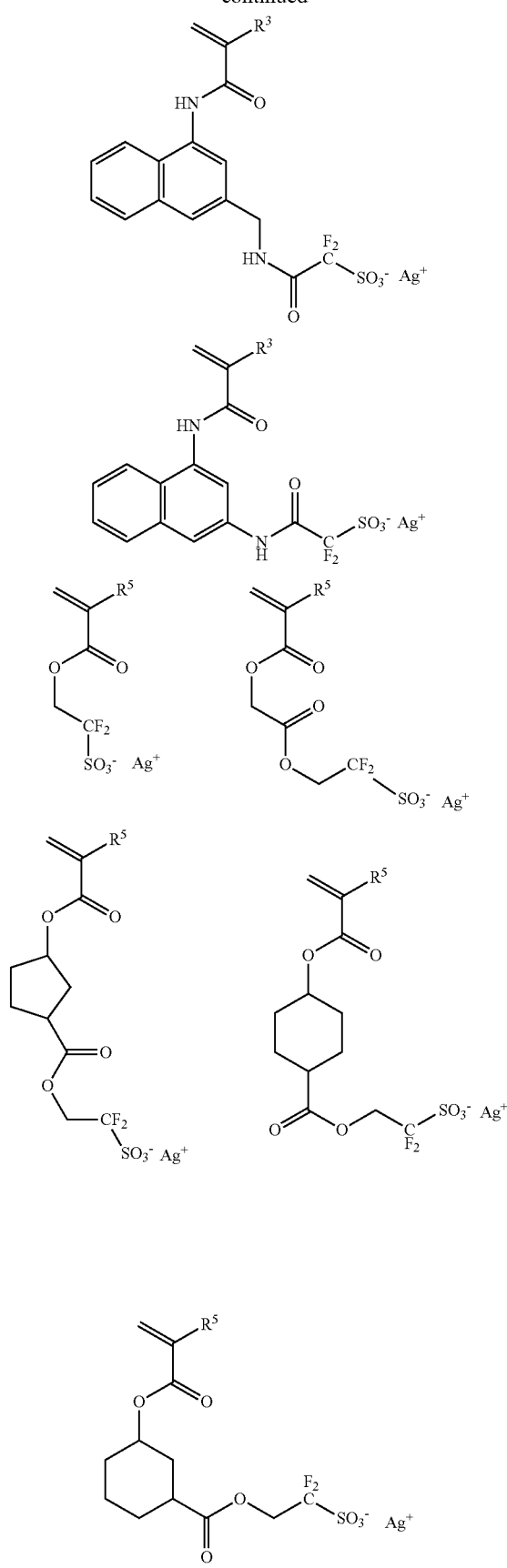

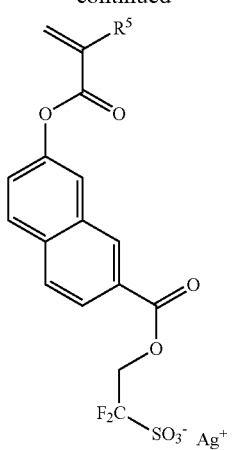
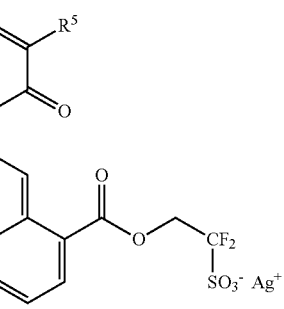
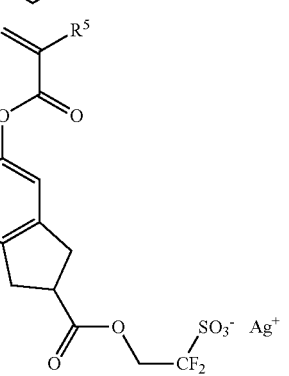
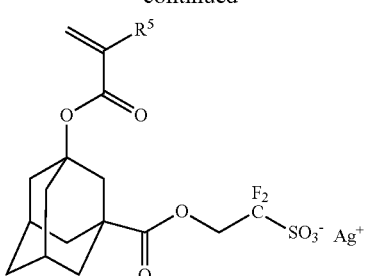
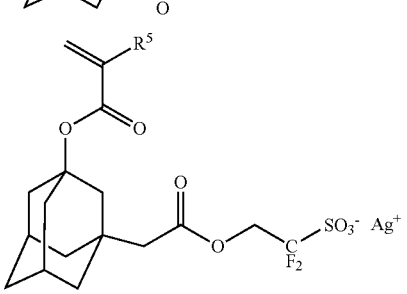
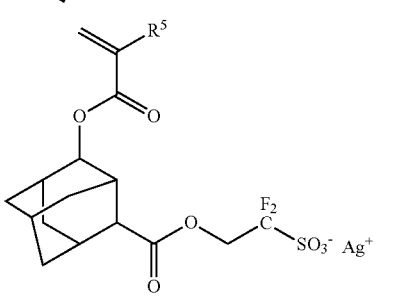
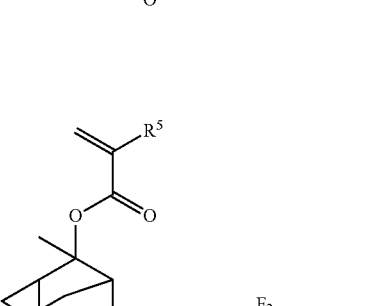
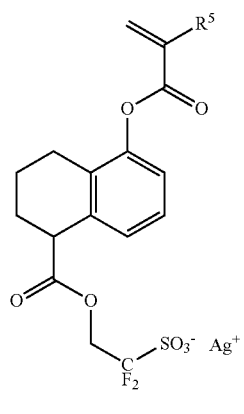
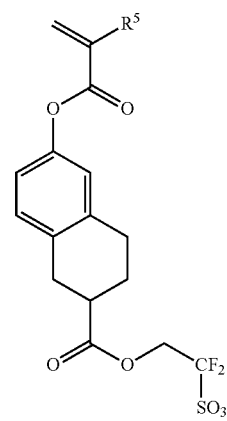
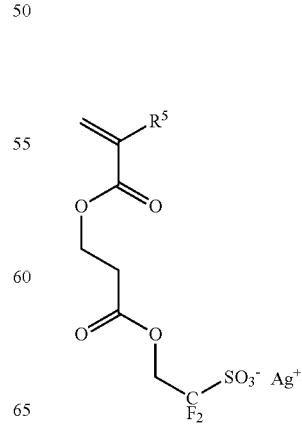
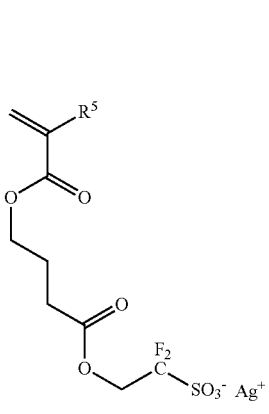

-continued
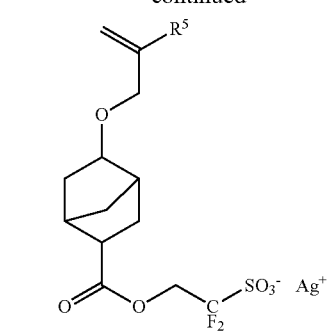
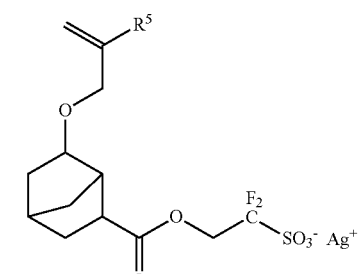
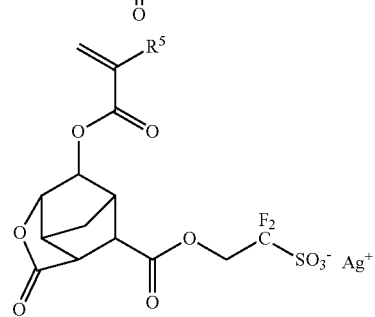
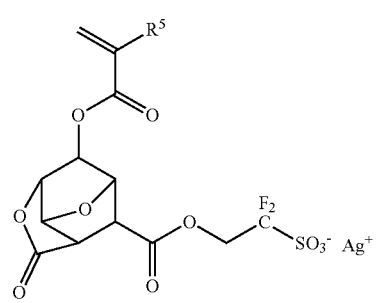
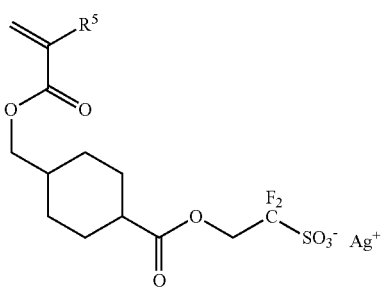
-continued
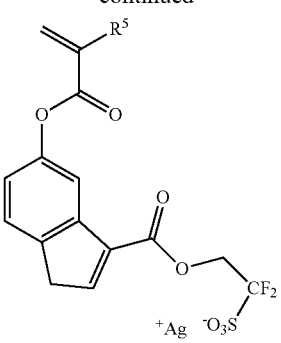
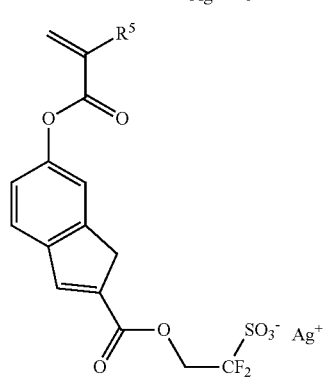
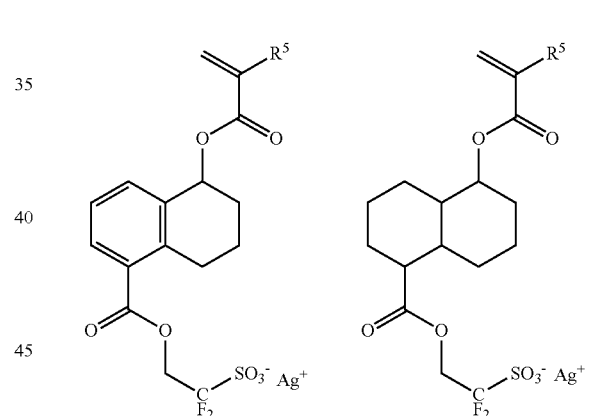
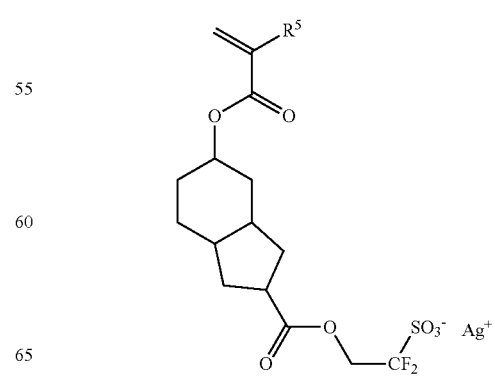

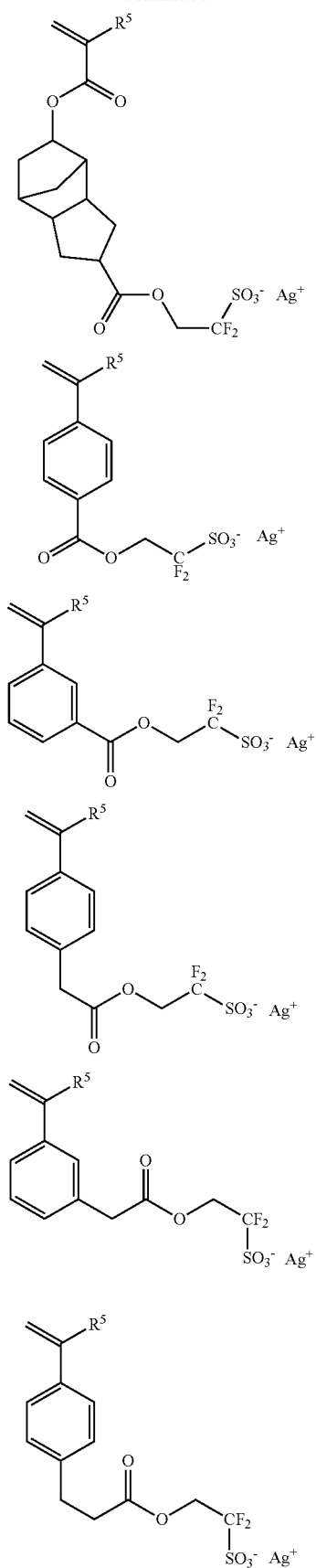
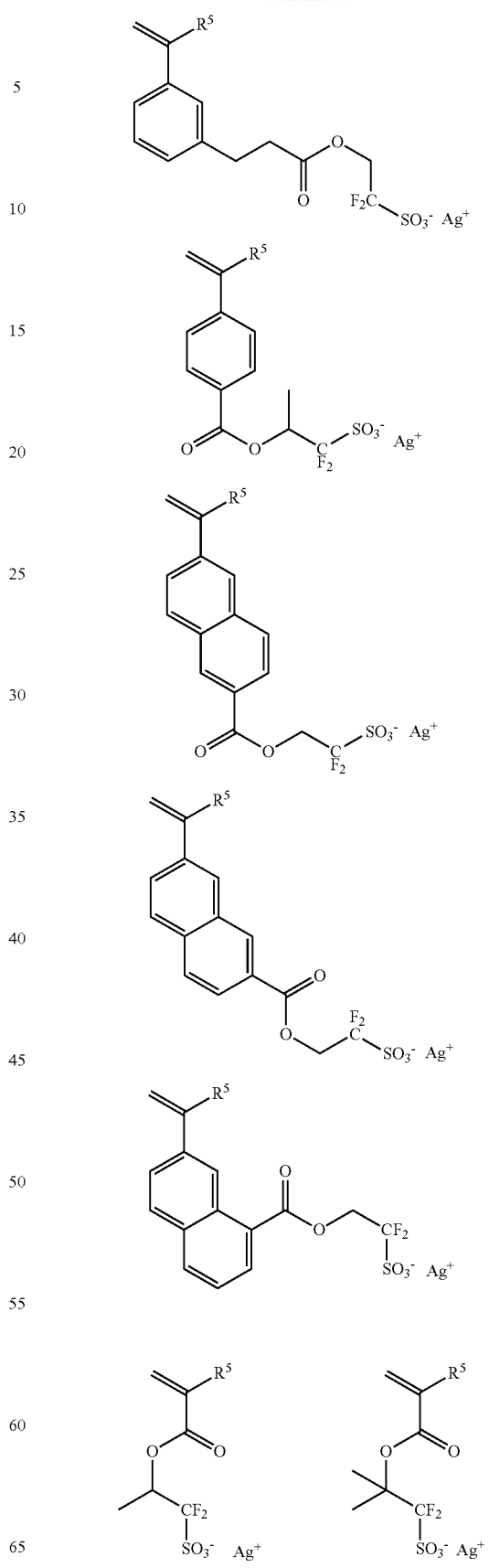

-continued
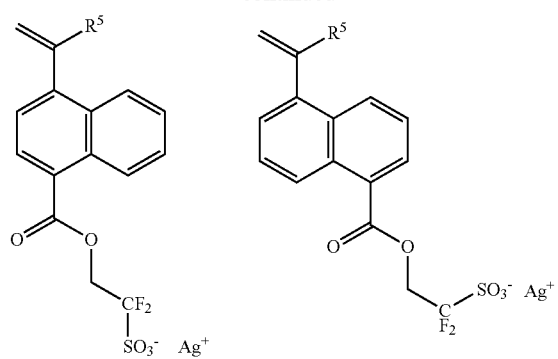
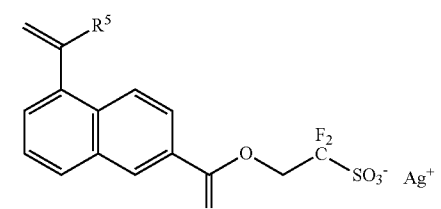
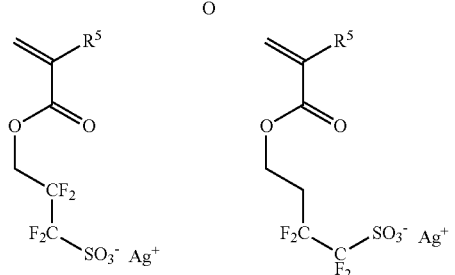
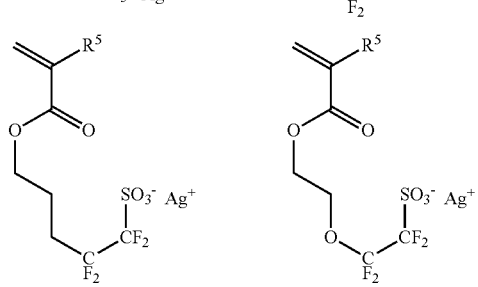
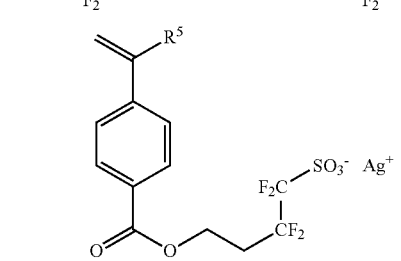
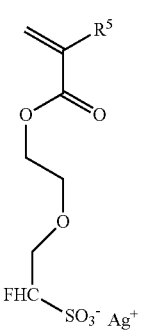
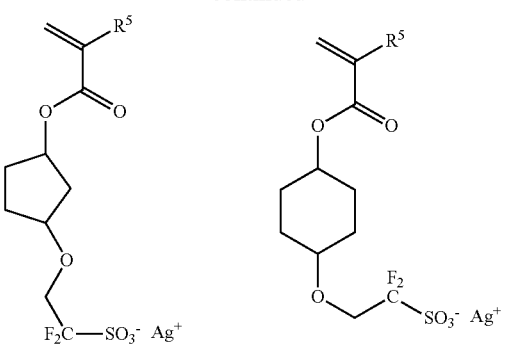
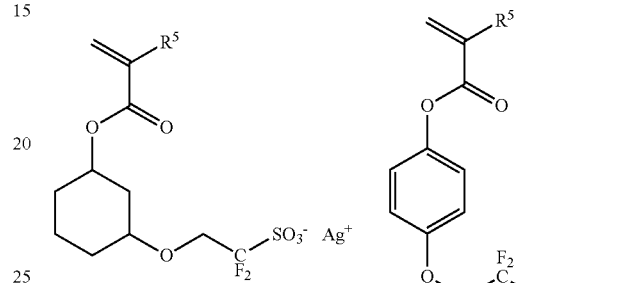
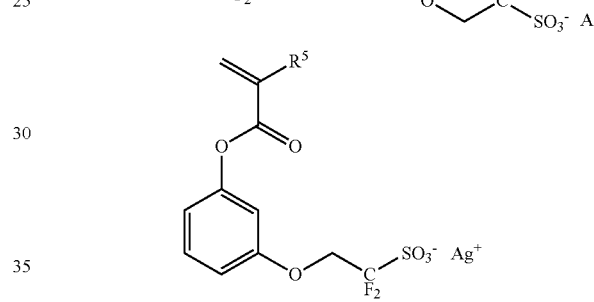
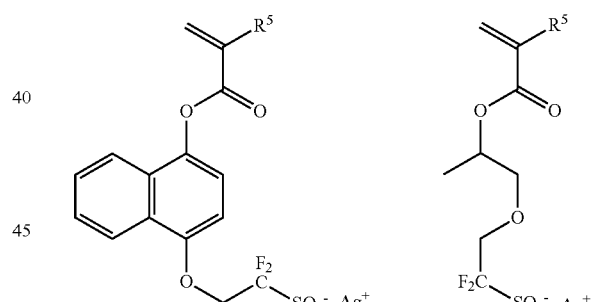
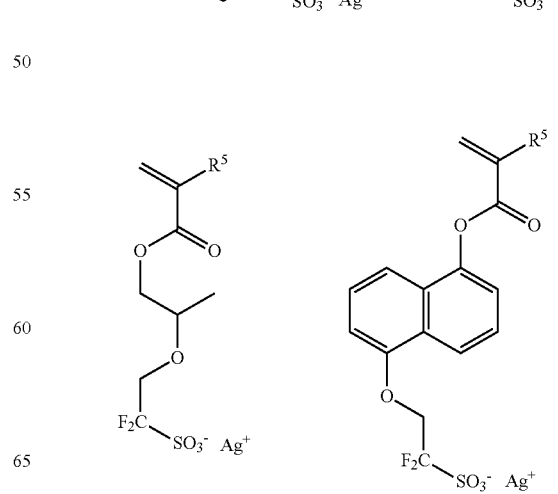

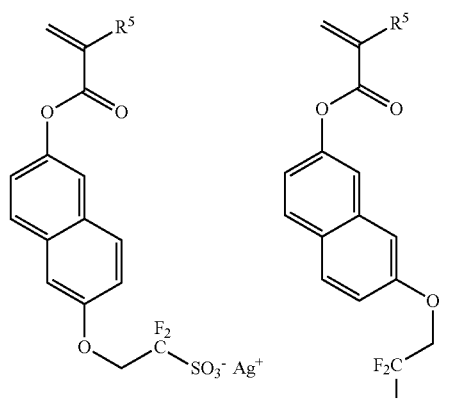
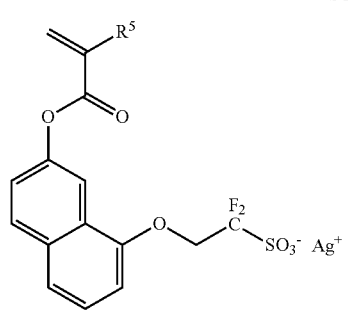
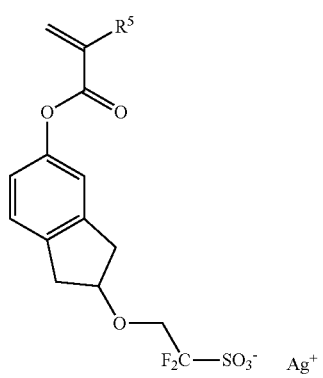
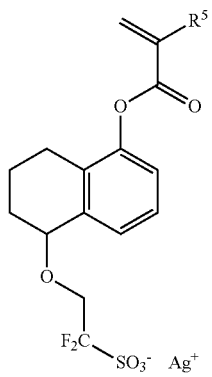
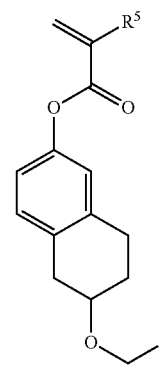
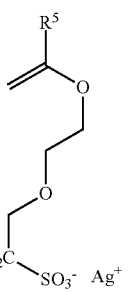
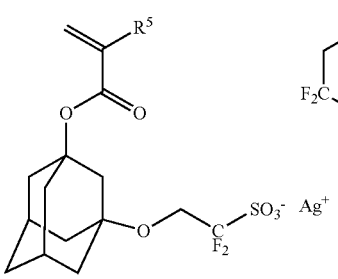
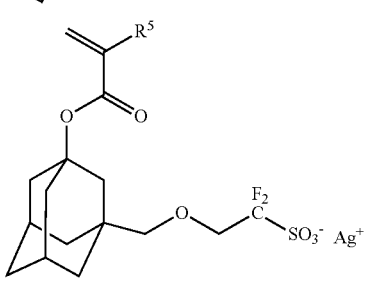
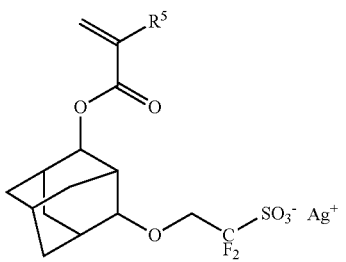
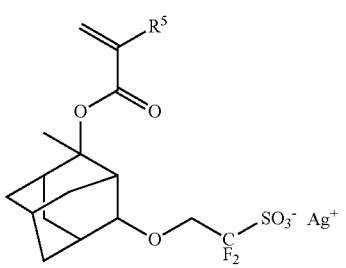
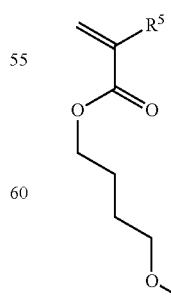
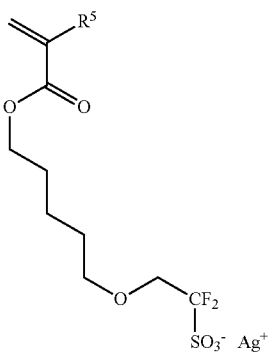

-continued
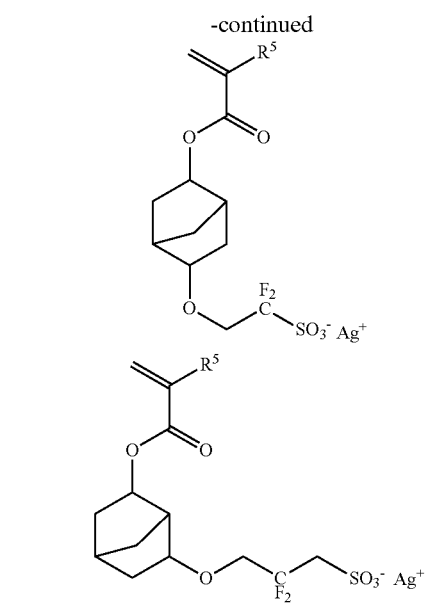
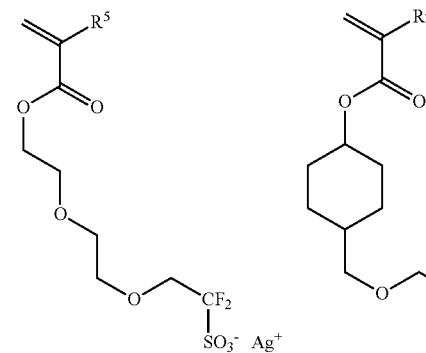
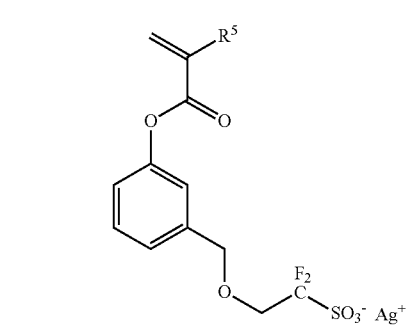
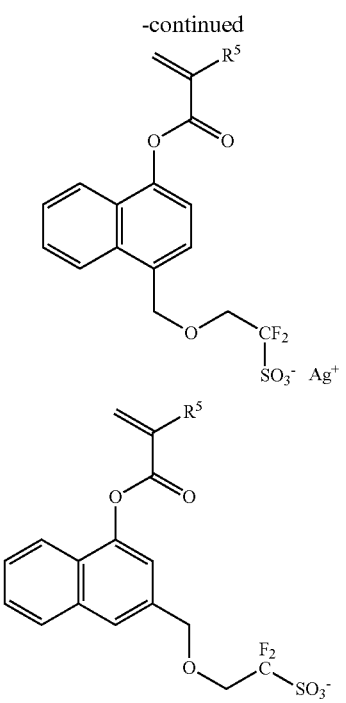
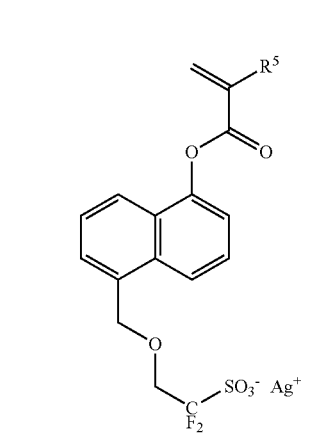
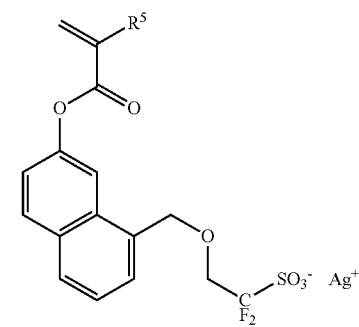

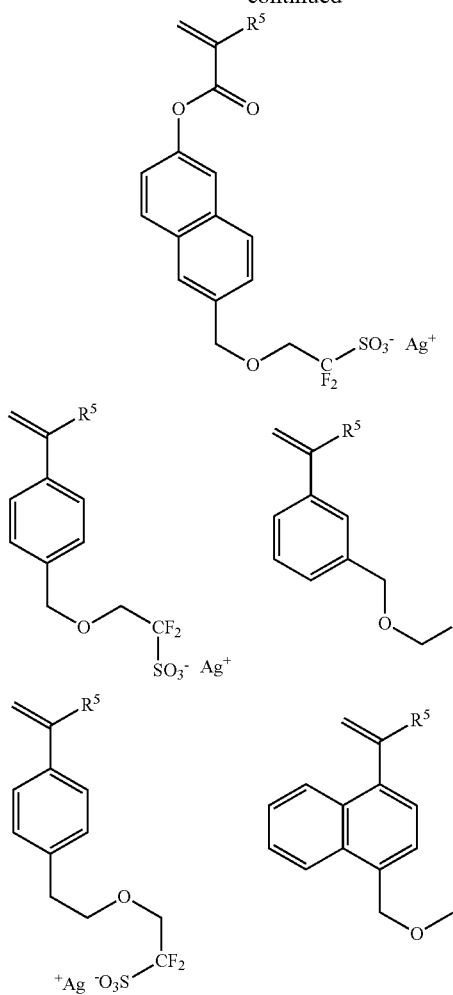
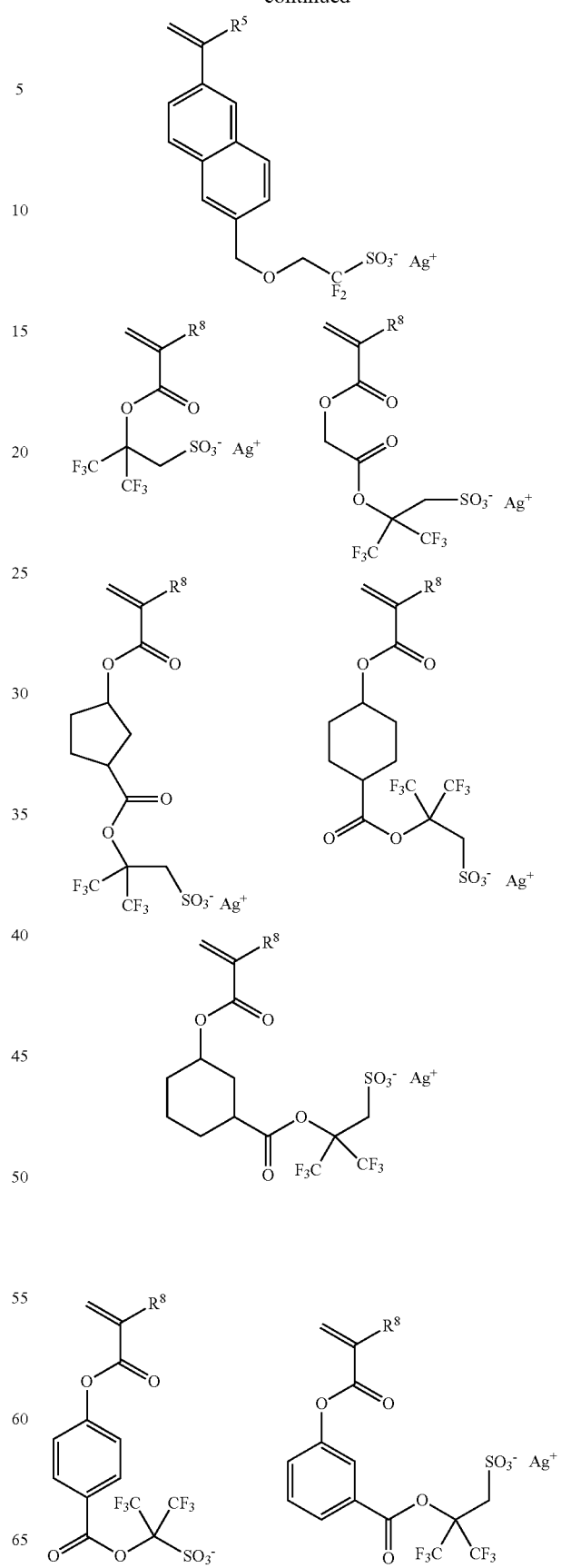

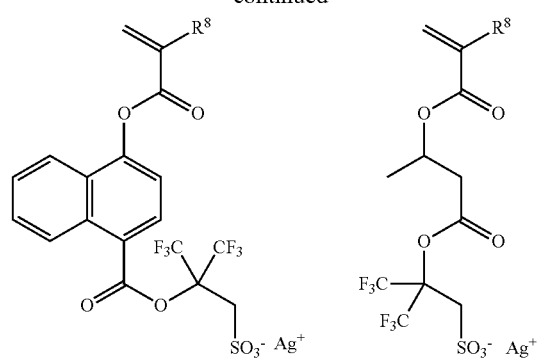
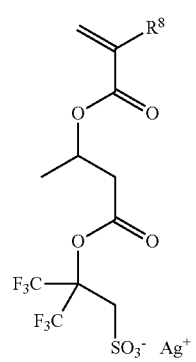
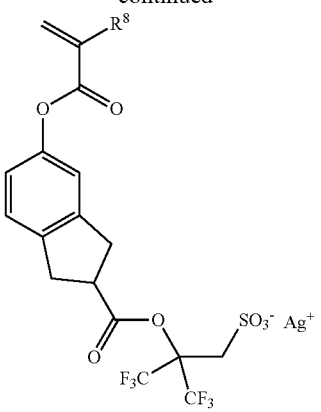
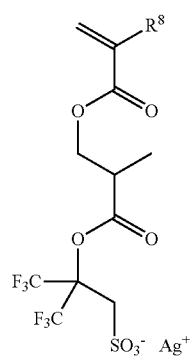
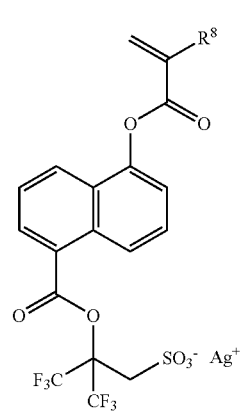
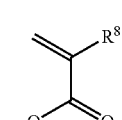
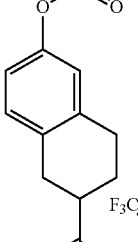
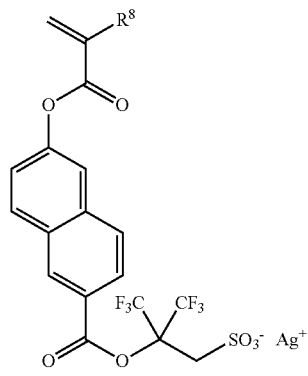
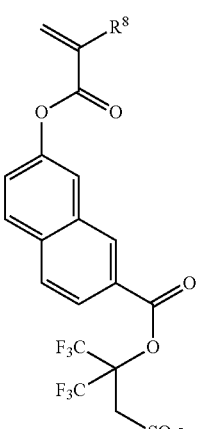
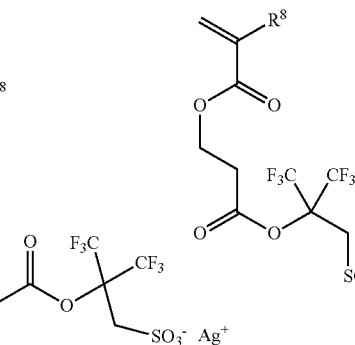
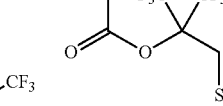
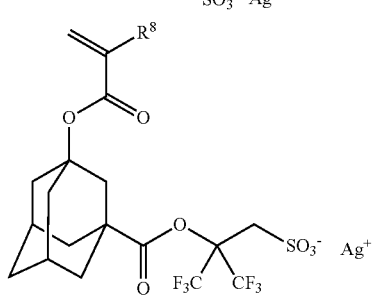
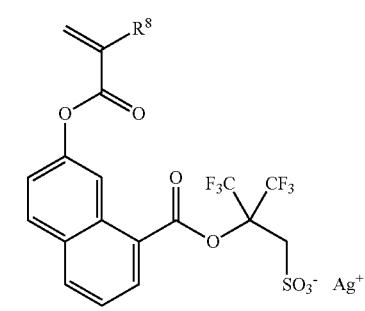
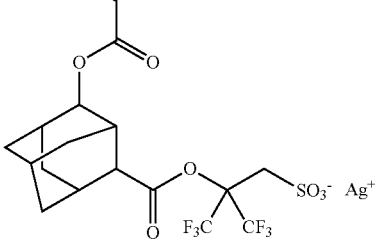
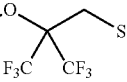
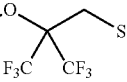

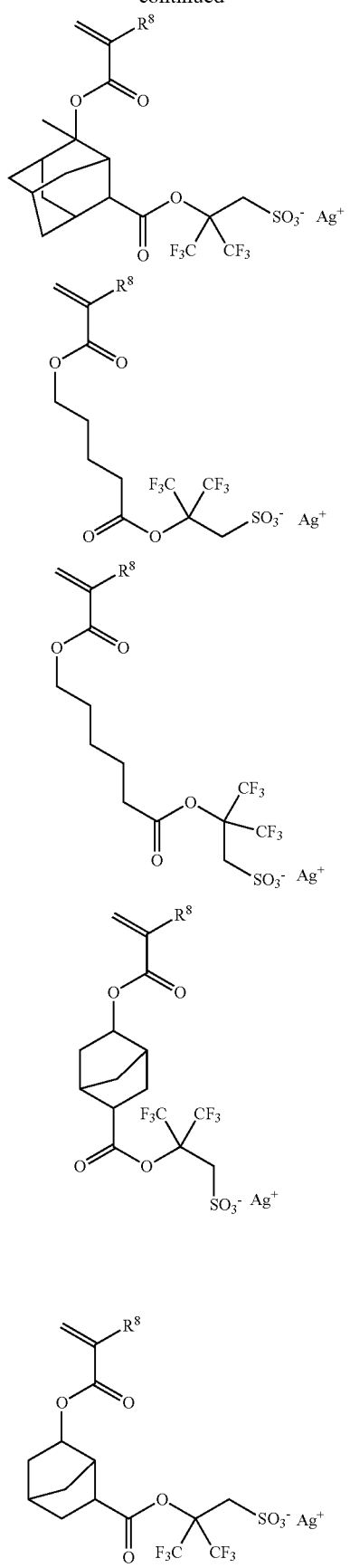

-continued
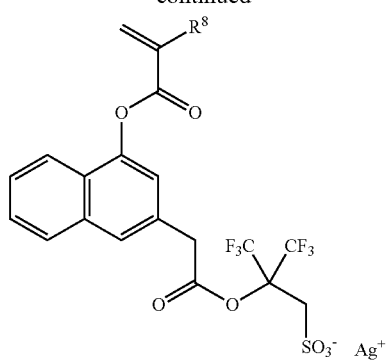
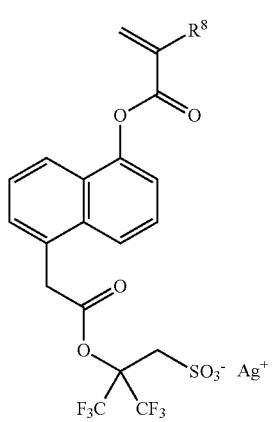
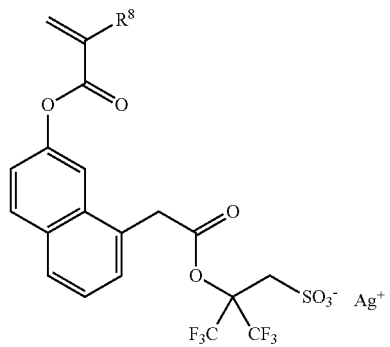
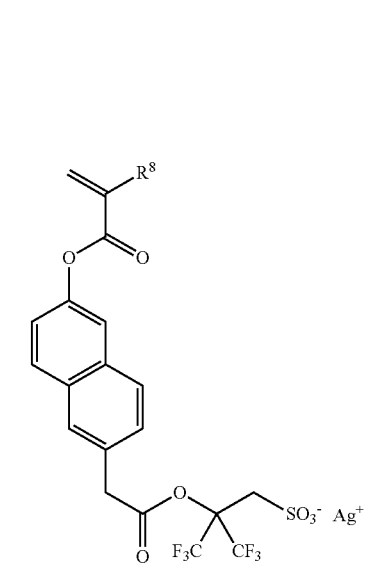
-continued
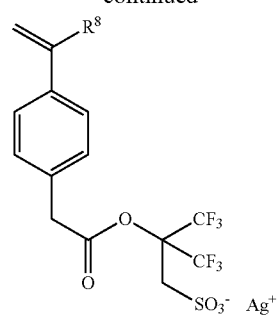
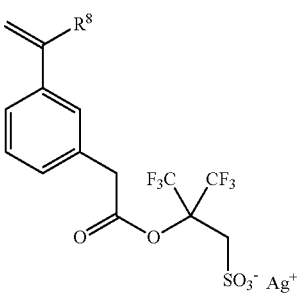
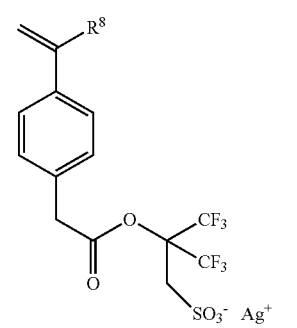
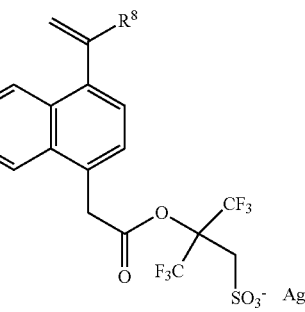
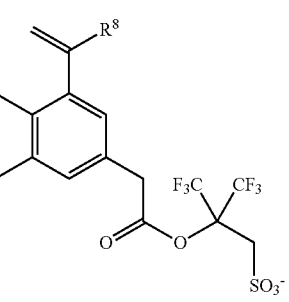

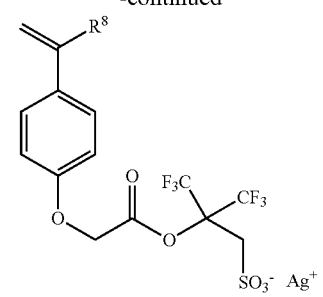
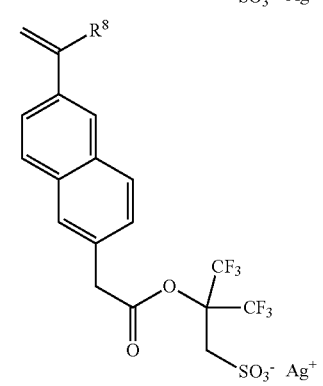
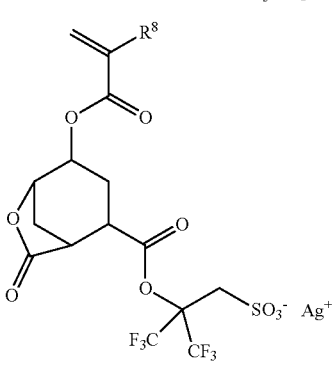
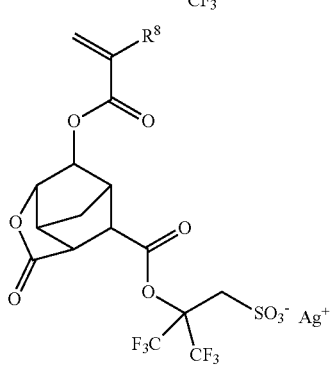
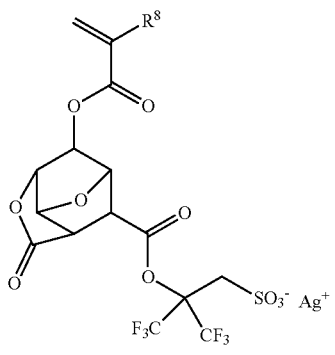
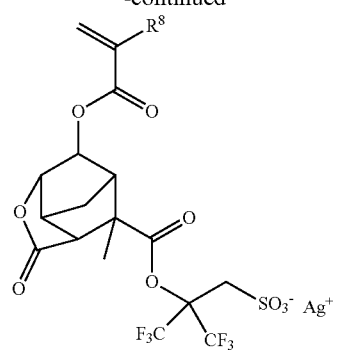
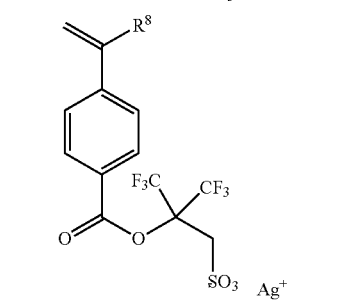
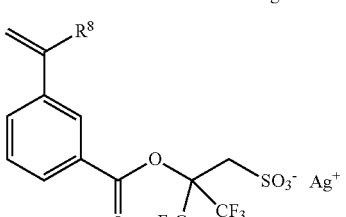
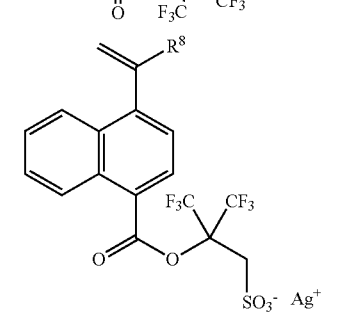
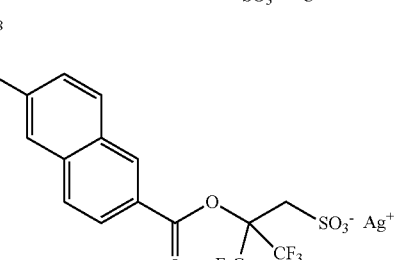
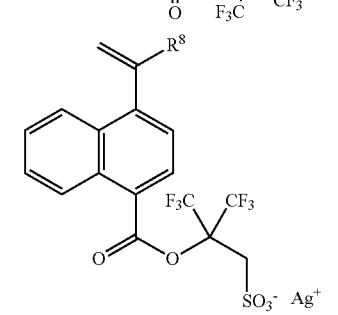

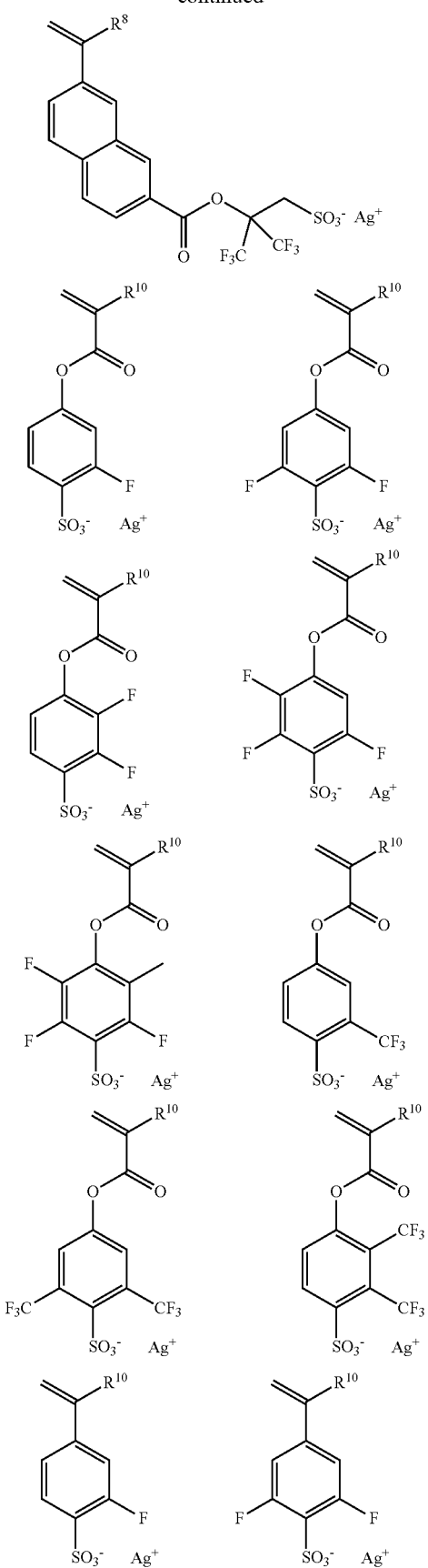
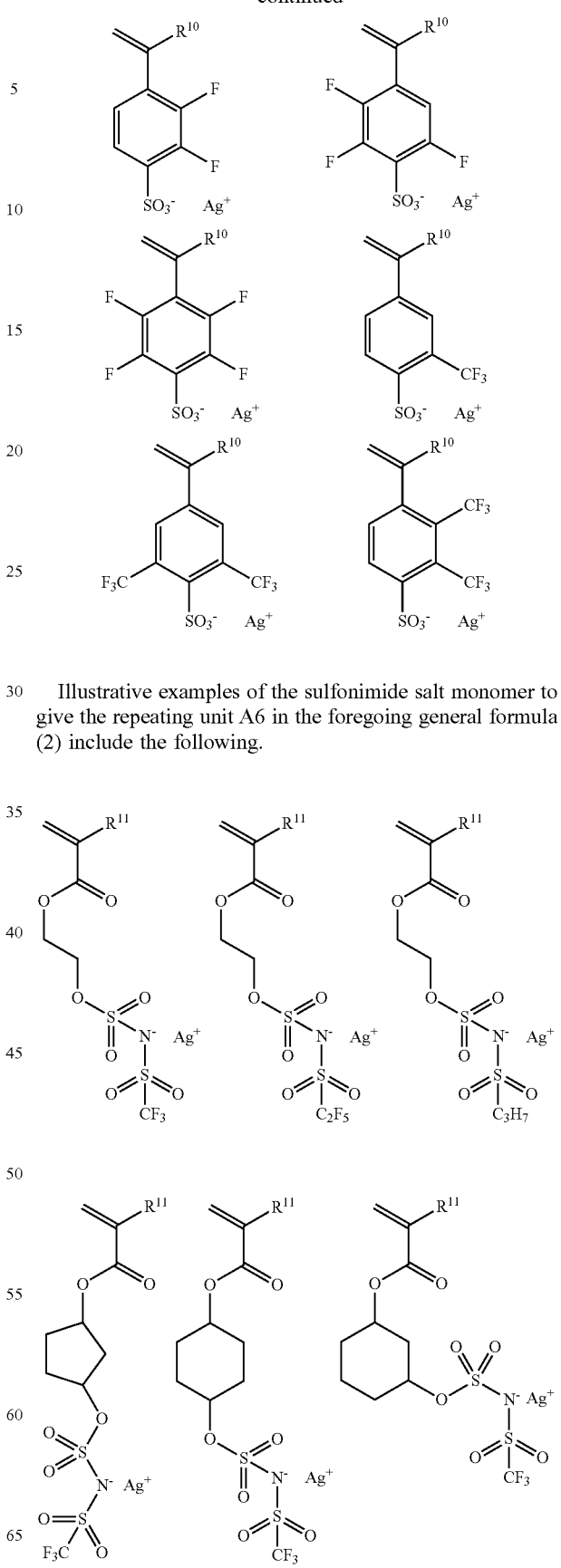
Illustrative examples of the sulfonimide salt monomer to give the repeating unit A6 in the foregoing general formula (2) include the following.

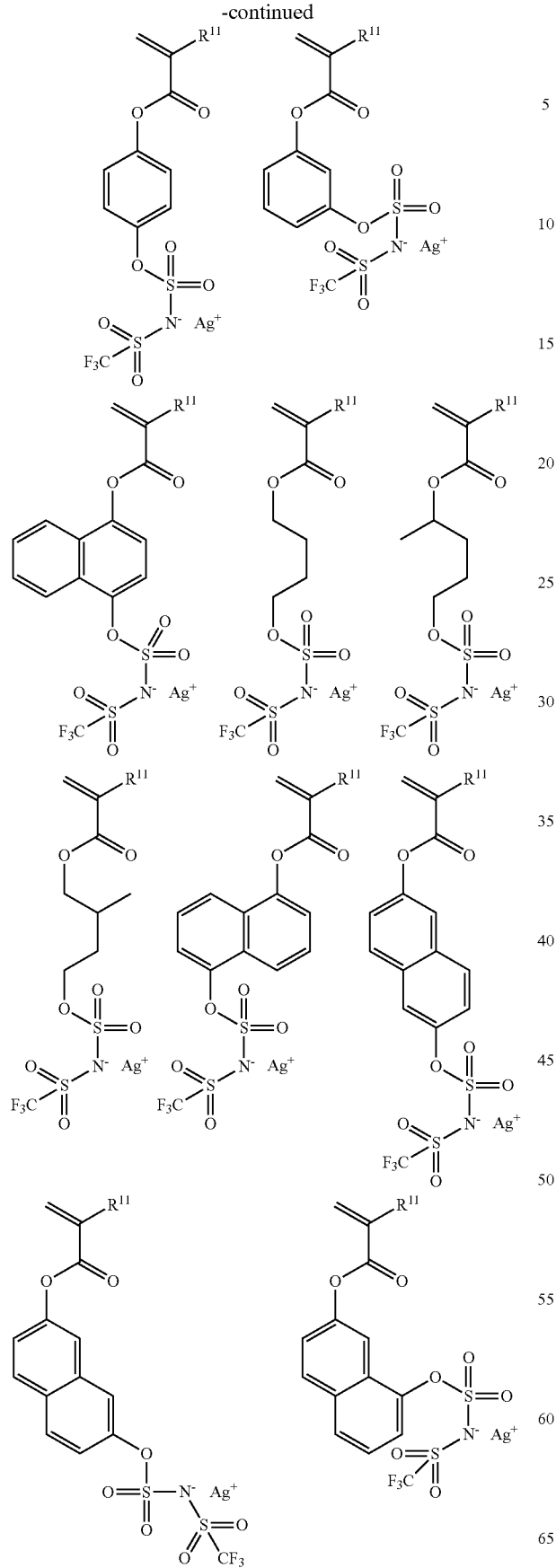
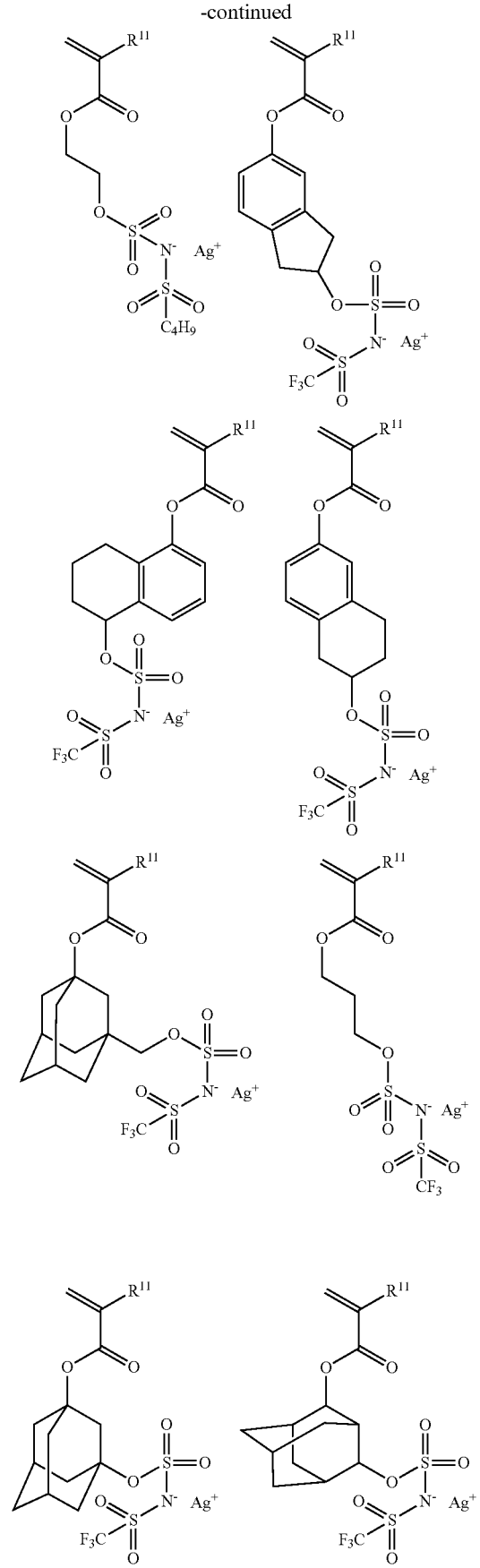

-continued
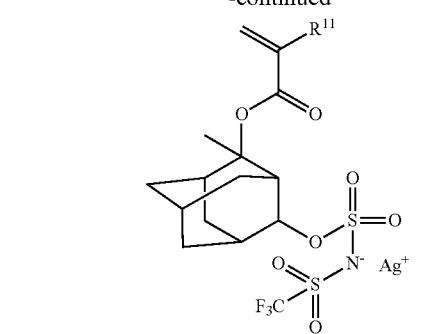
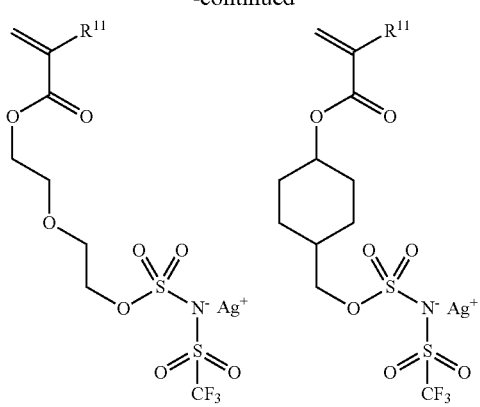
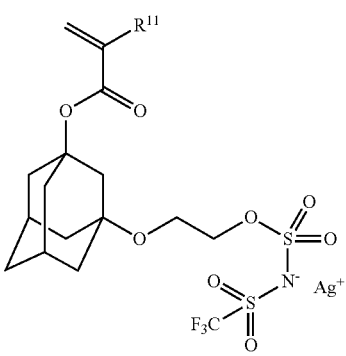
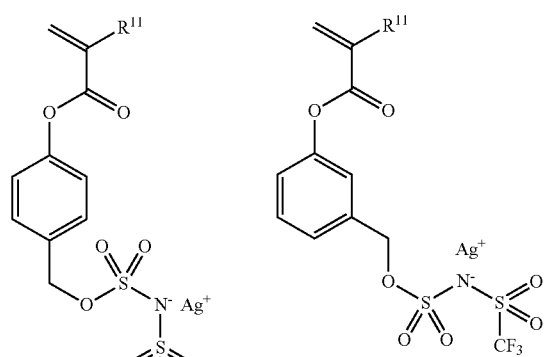
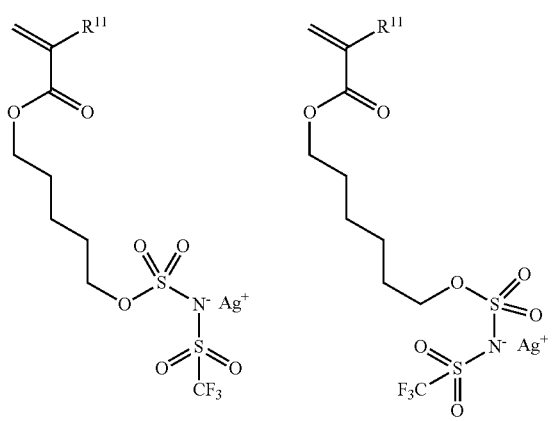
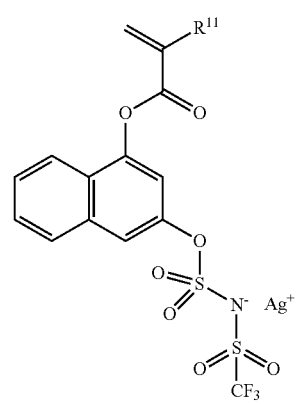
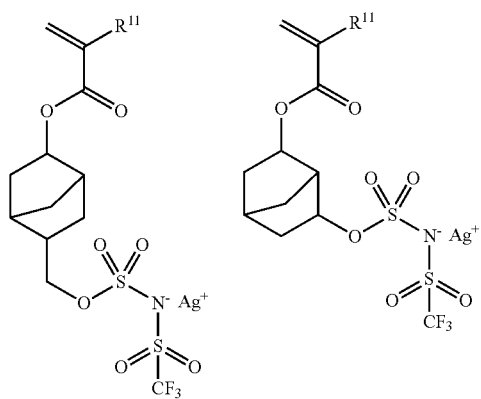

-continued
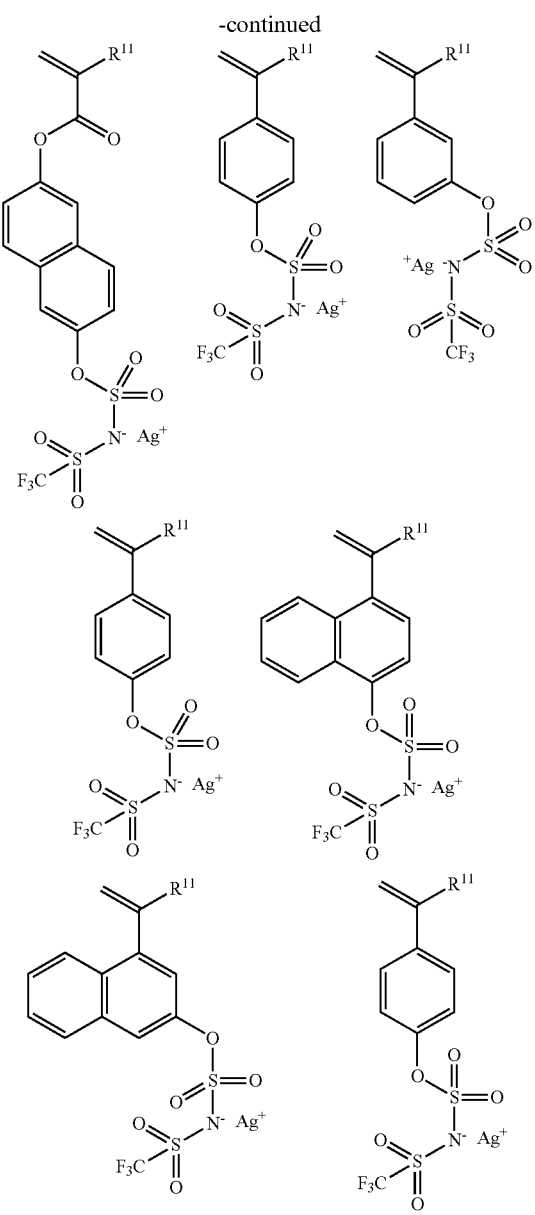
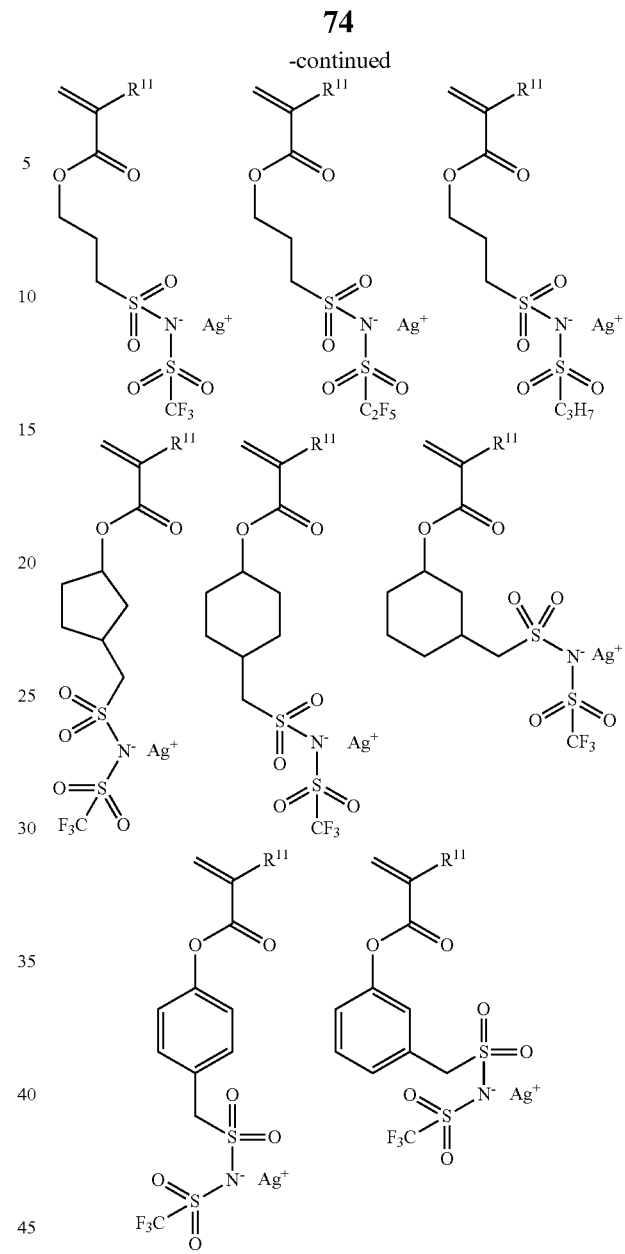
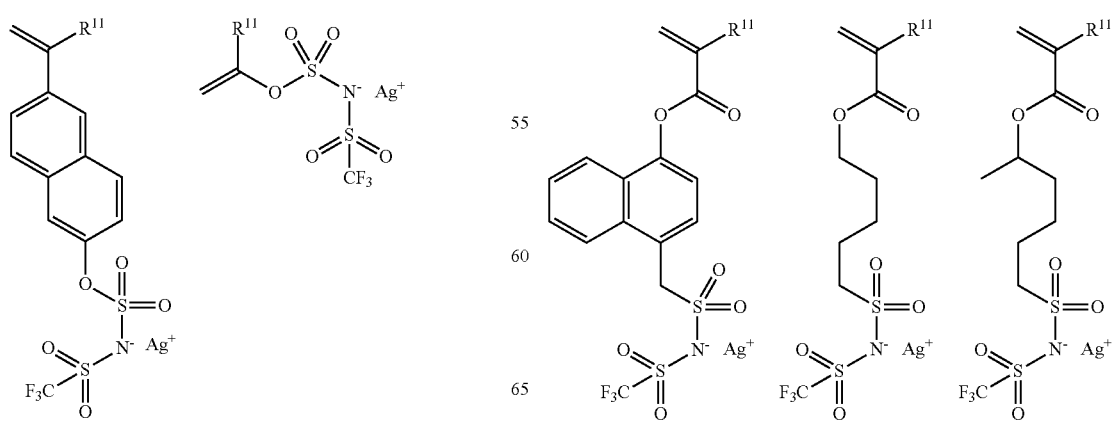

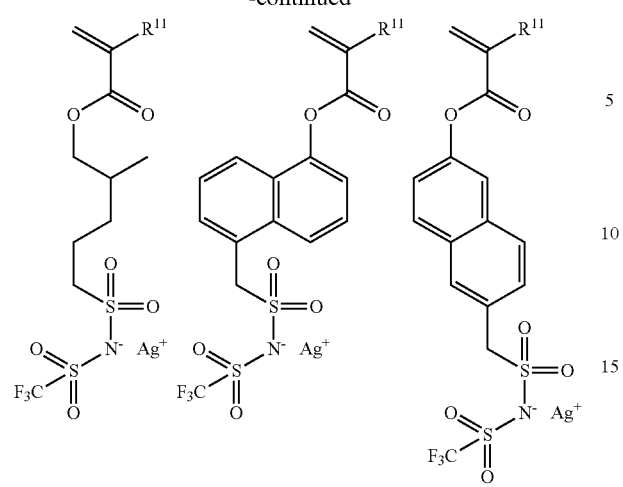
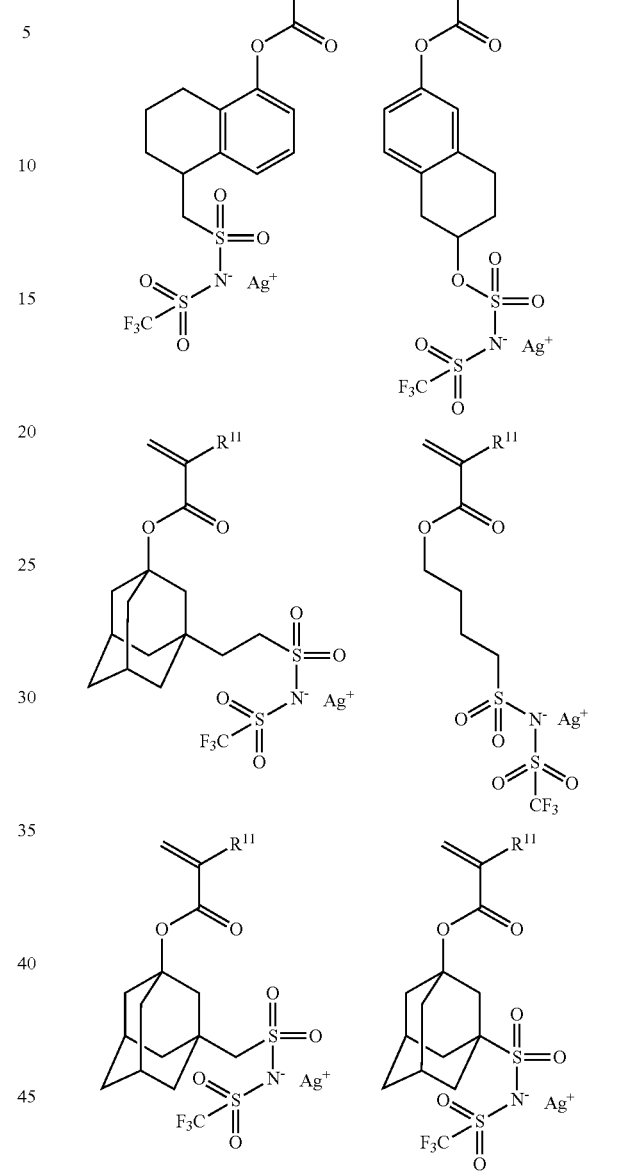
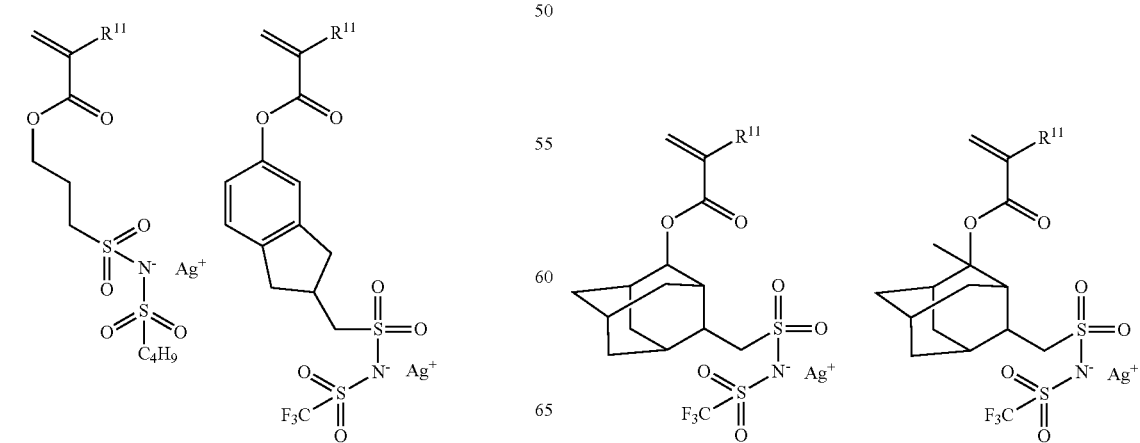

77
-continued
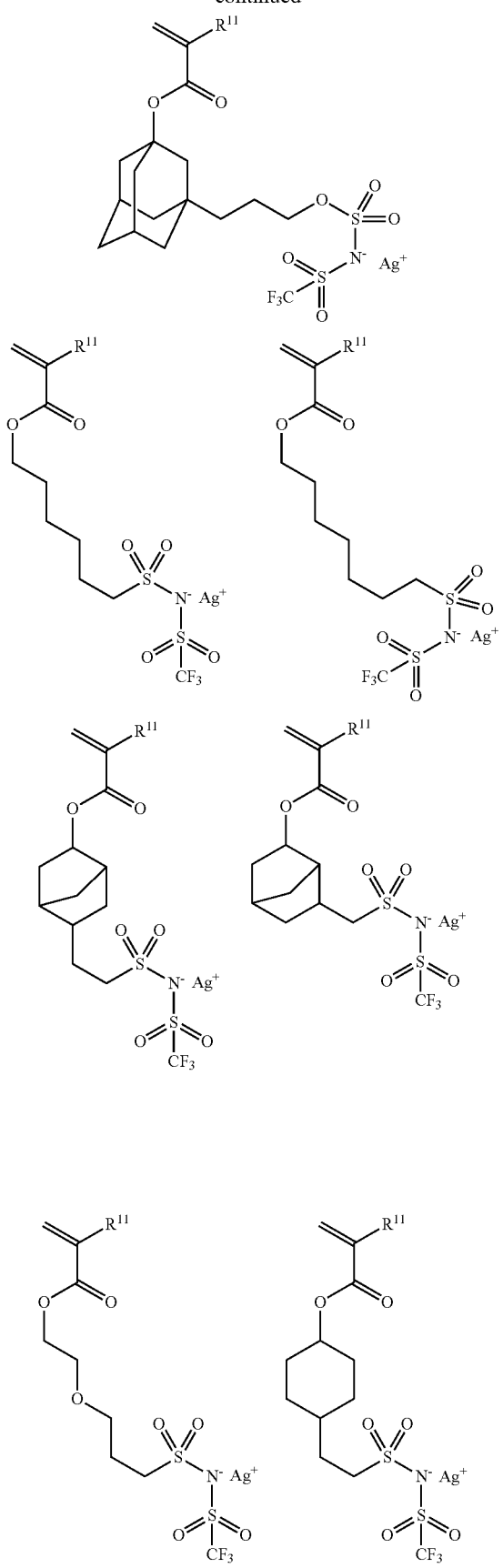
78
-continued
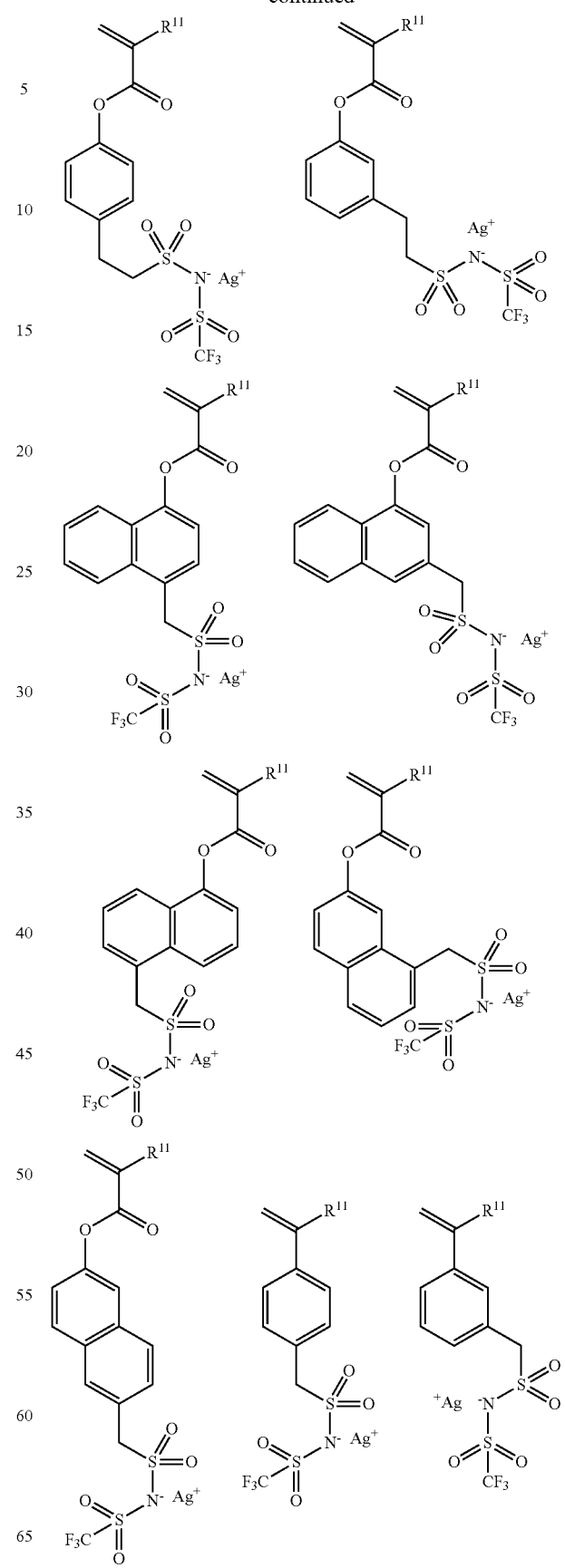

79
-continued
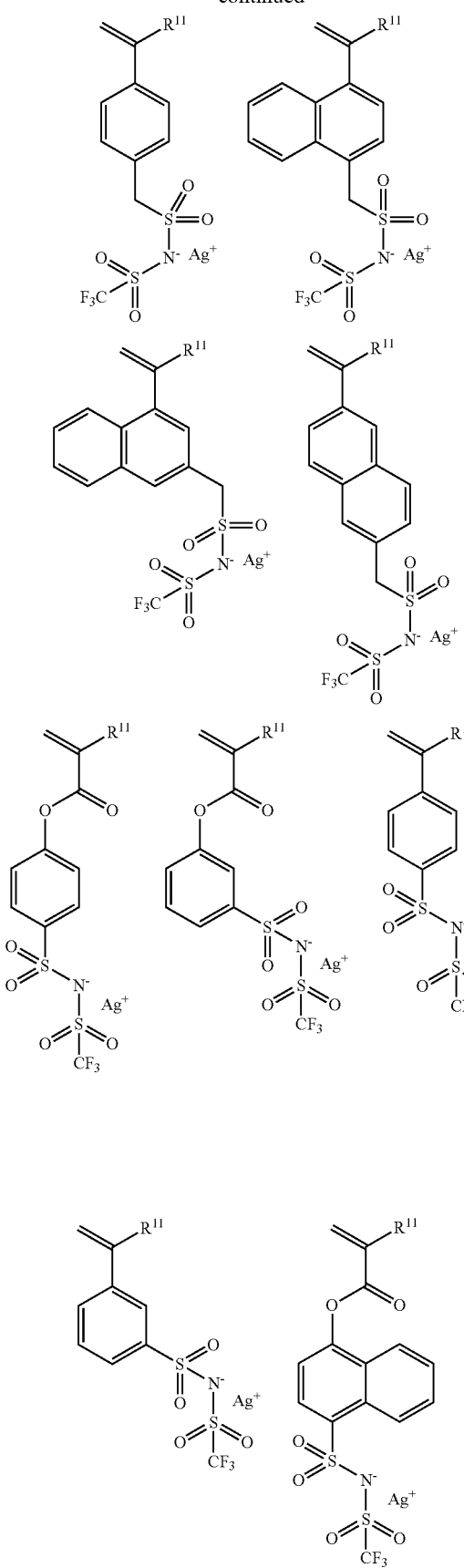
80
-continued
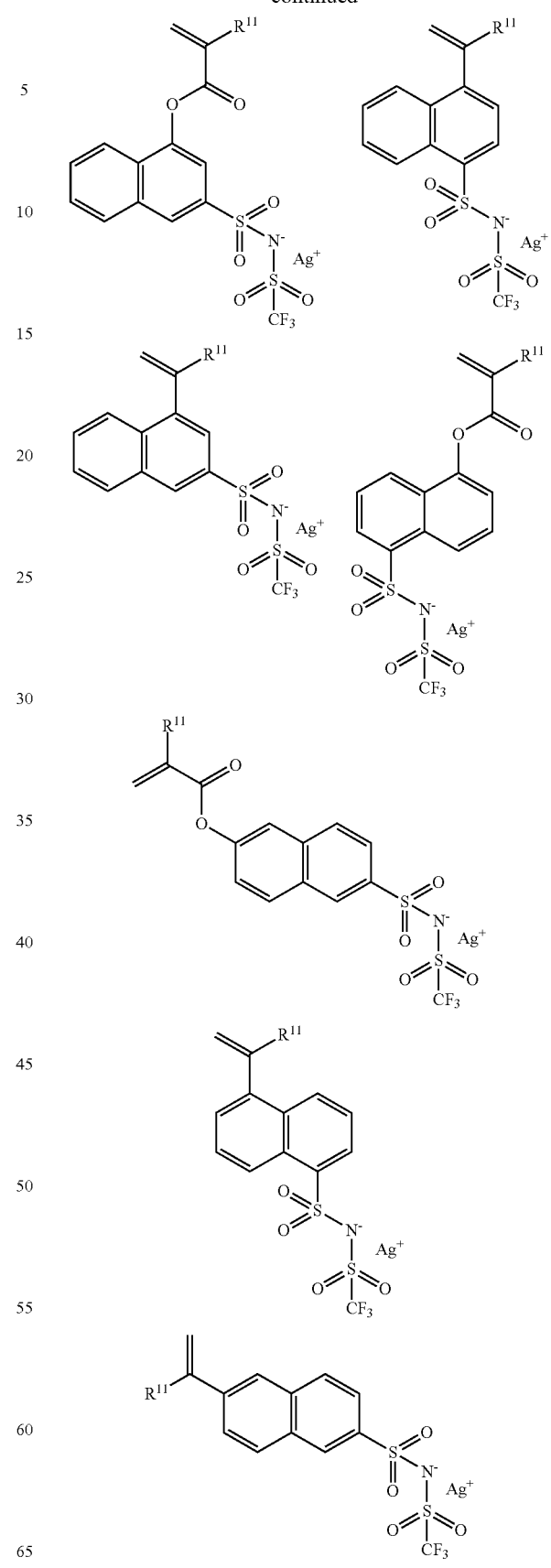

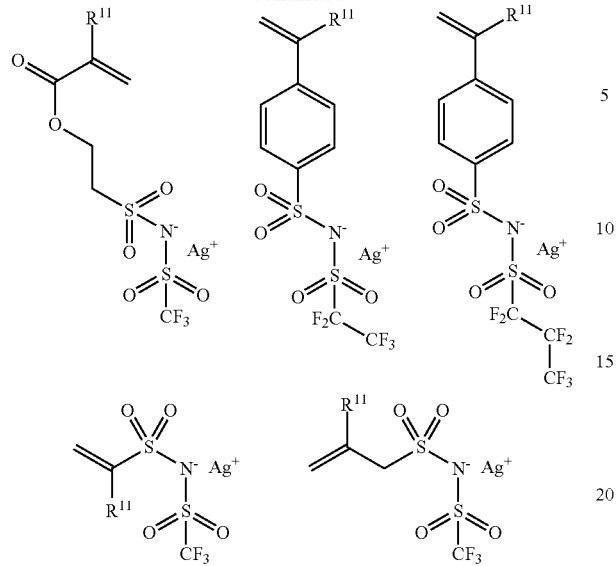
Illustrative examples of the sulfonamide salt monomer to give the repeating unit A7 in the foregoing general formula (2) include the following.
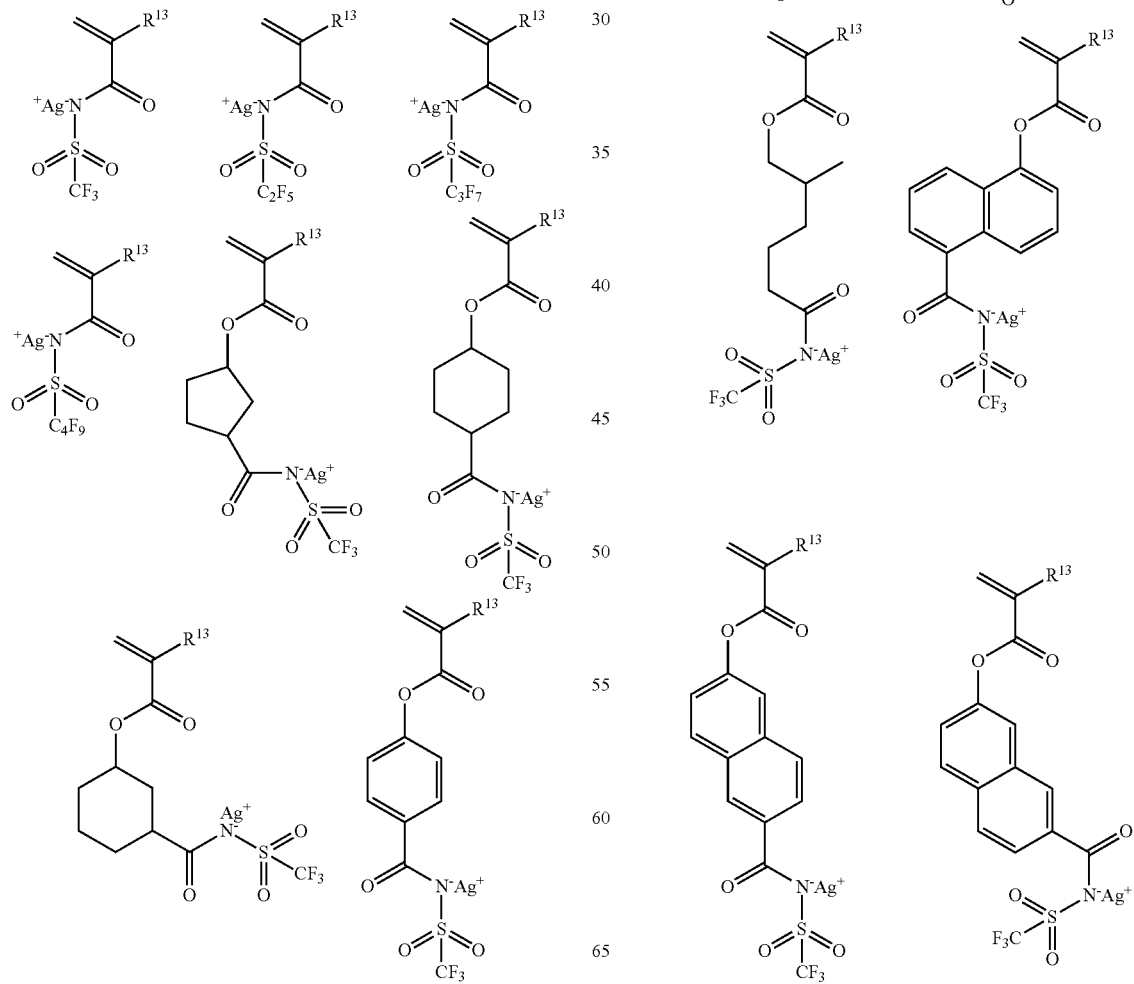
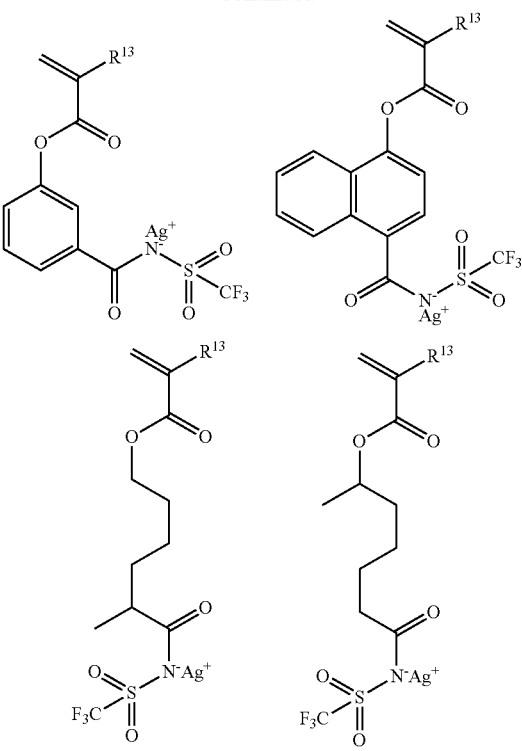

-continued
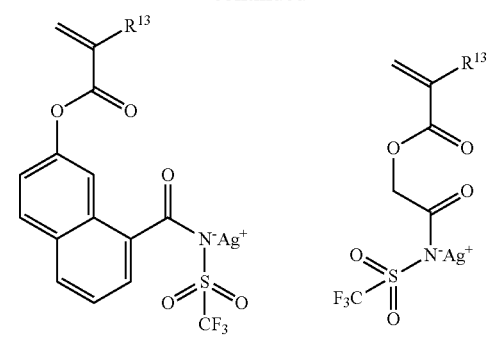
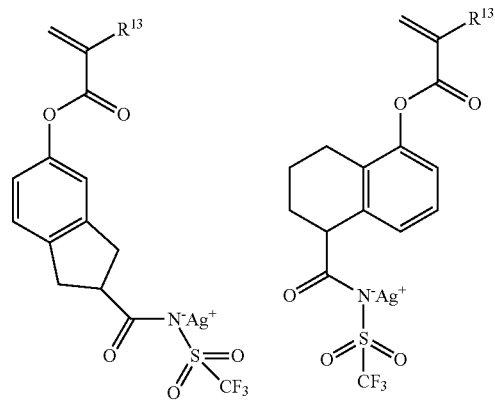
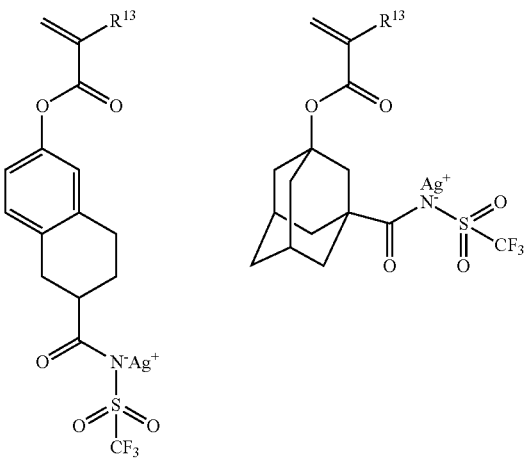
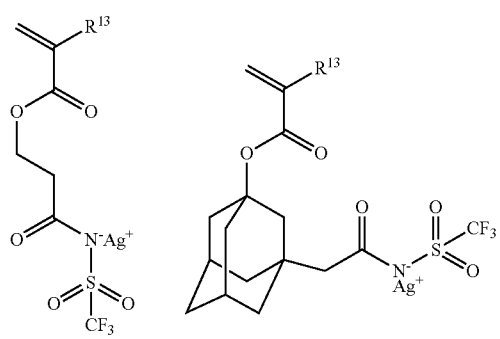
-continued
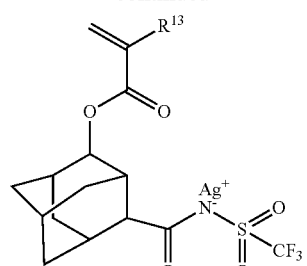
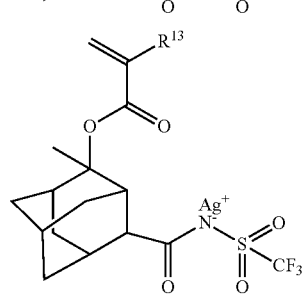
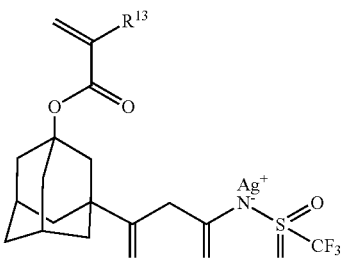
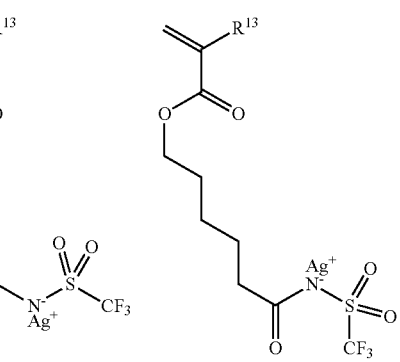
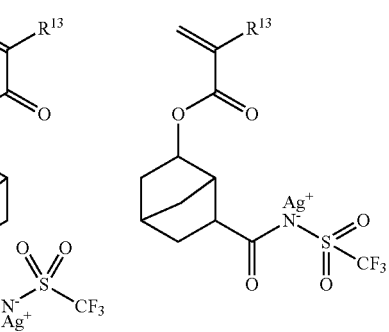

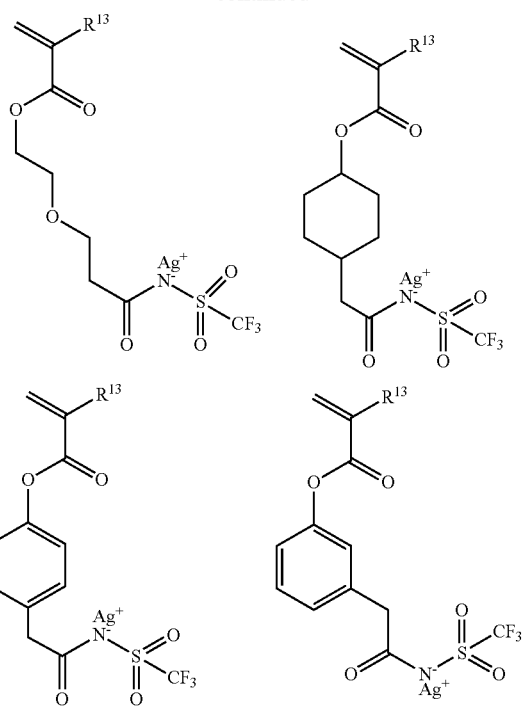
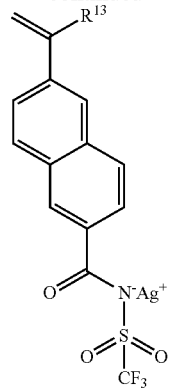
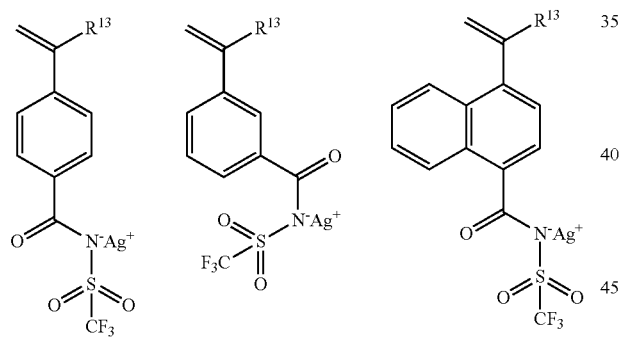
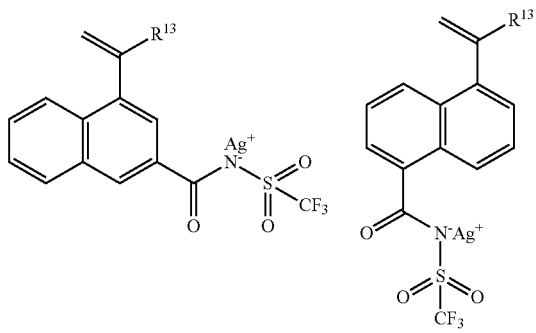

In these formulae, $R^1$, $R^3$, $R^5$, $R^8$, $R^{10}$, $R^{11}$, and $R^{13}$ are as described above.

As a method for synthesizing the silver salt monomer to give the repeating units A1 to A7 shown by the general formula (2), the monomer can be obtained by the method of mixing silver chloride with ammonium salt composed of an ammonium cation and the fluorosulfonic acid (fluorosulfonate) anion, the fluoroimidic acid (fluorosulfonimide) anion, or the fluoroamic acid (fluorosulfonamide) anion described above, for example, in an organic solvent. In this case, it is preferable to remove ammonium chloride formed as a byproduct by washing with water.

The polymer compound in the inventive bio-electrode composition can also have a repeating unit B having (meth) acrylate shown by the following general formula (3), in addition to the repeating unit A, as a repeating unit to add tackiness.

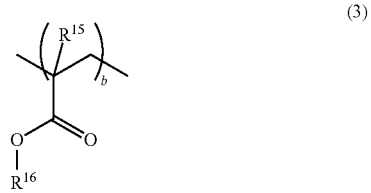

In this formula, $R^{15}$ represents a hydrogen atom or a methyl group; $R^{16}$ represents a linear, branched, or cyclic alkyl group having 1 to 30 carbon atoms, a linear, branched, or cyclic alkenyl group having 2 to 30 carbon atoms, or a linear, branched, or cyclic alkynyl group having 2 to 30 carbon atoms, in which the bonded part with the ester group is preferably a primary or secondary carbon, optionally having a hydroxy group, an ether group, an ester group, or an aromatic group; $R^{16}$ preferably has 4 to 30, more preferably 6 to 28 carbon atoms; and "b" satisfies $0 \leq b < 1.0$.

Illustrative examples of the monomer to give the repeating unit B include the following.

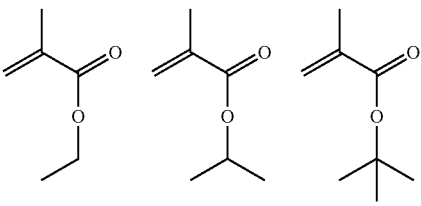

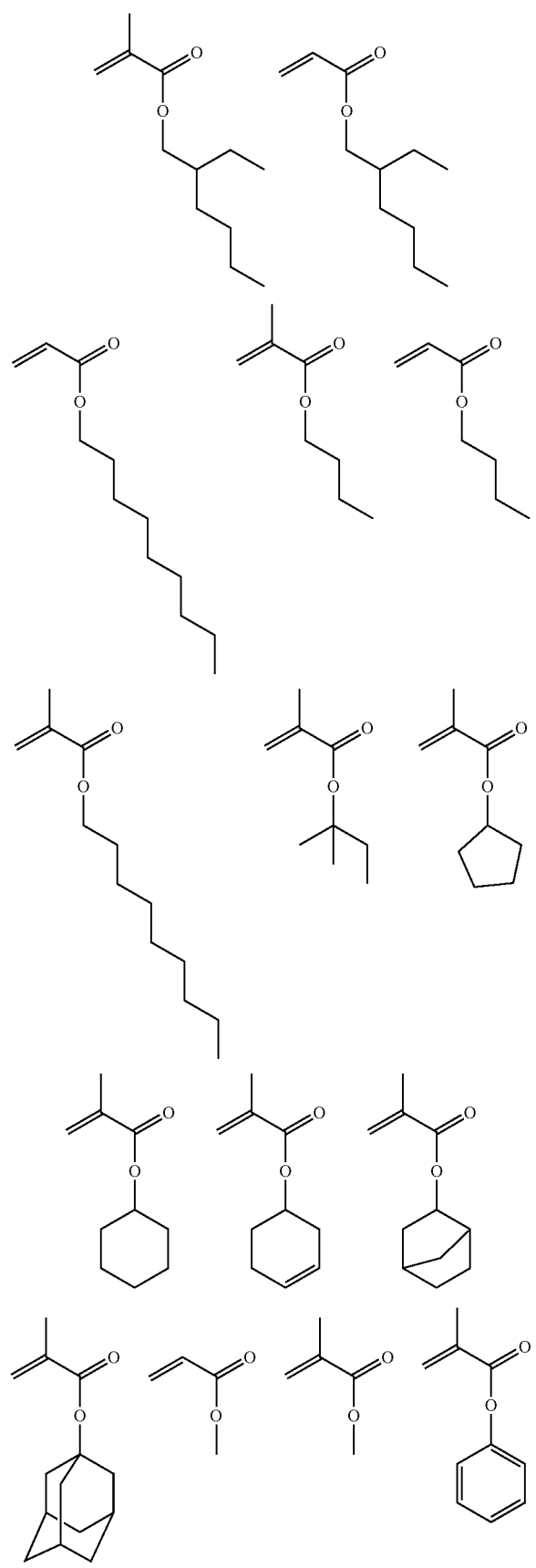
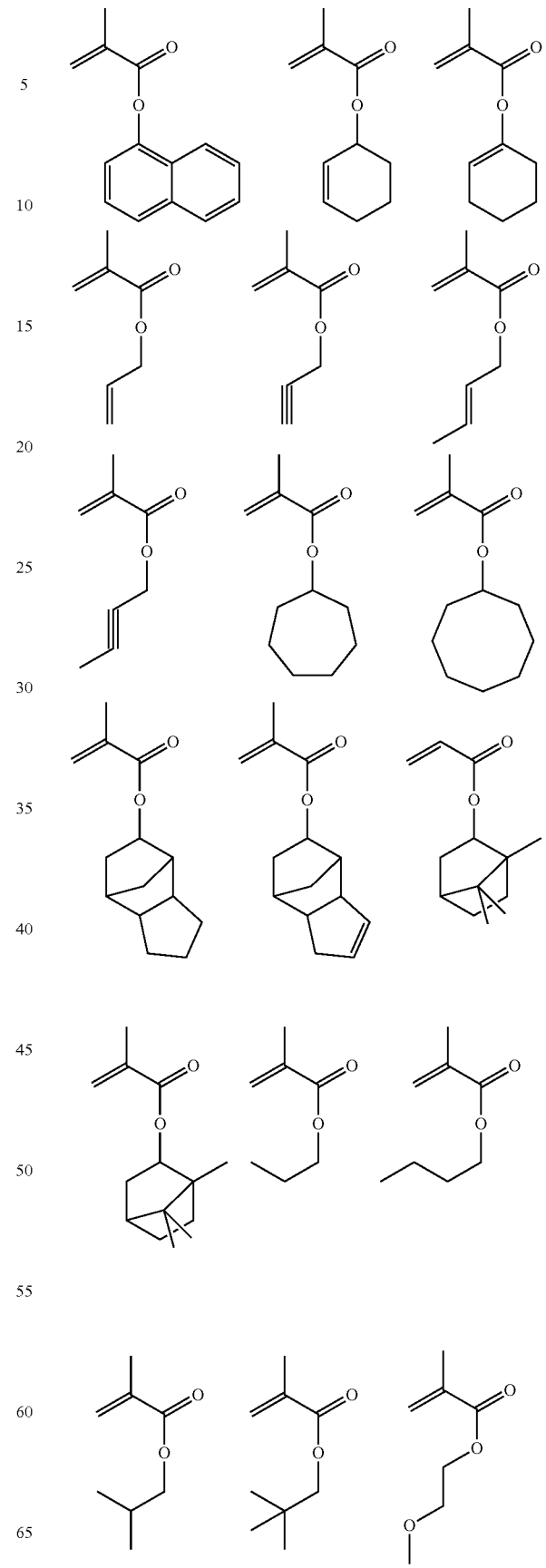

89
-continued
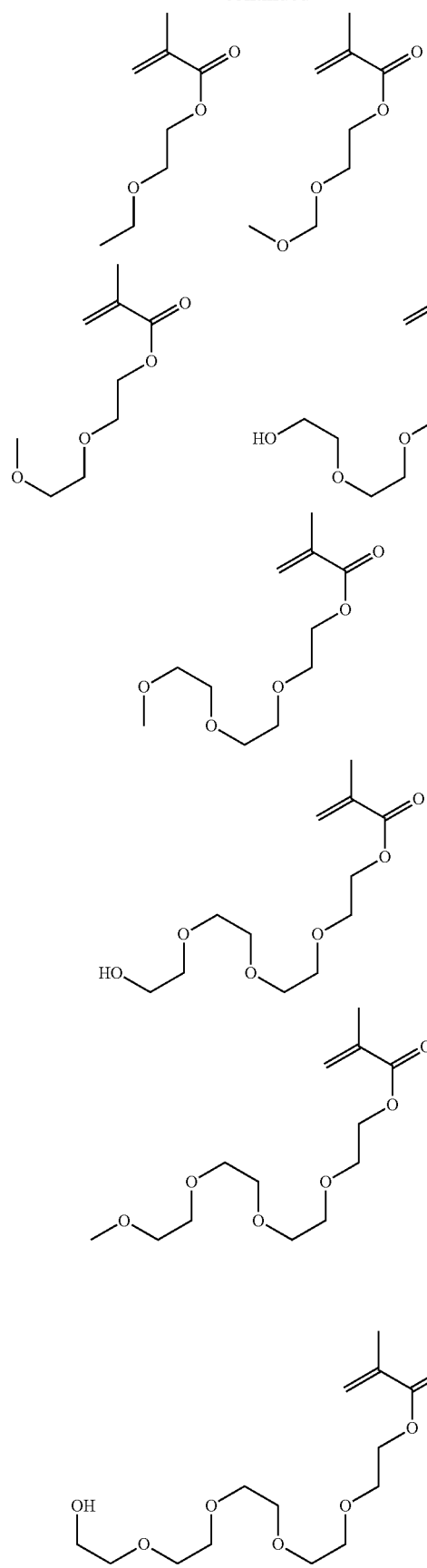
90
-continued
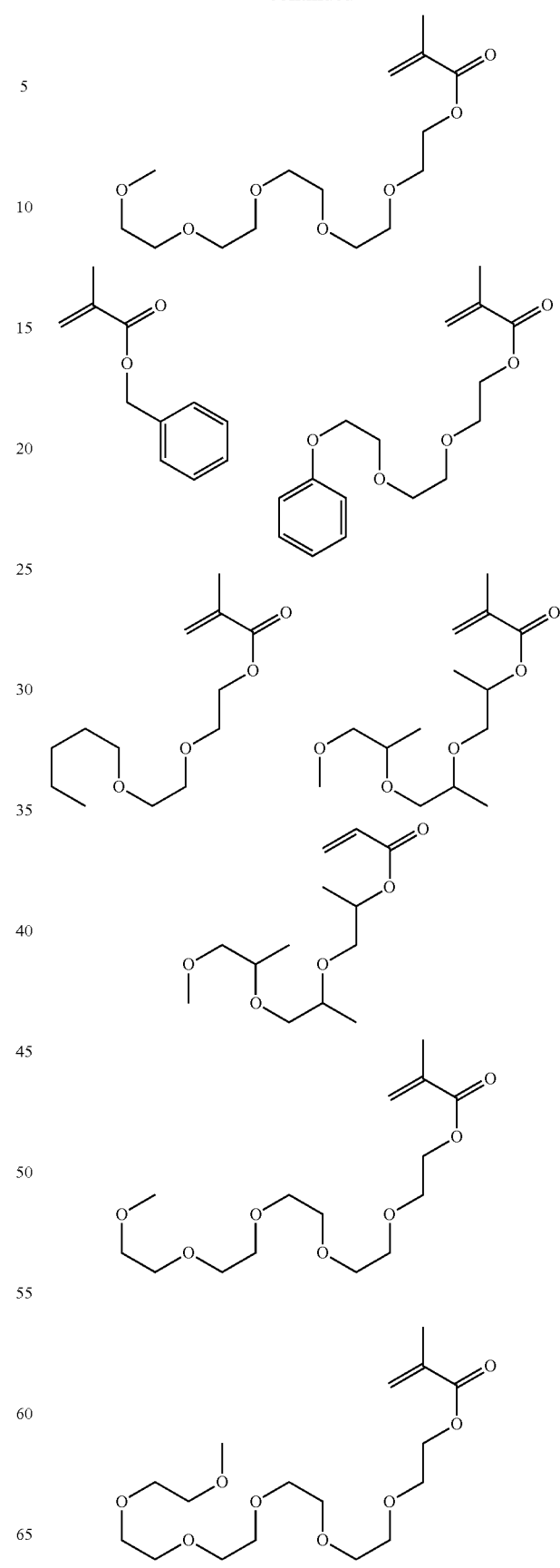

91
-continued
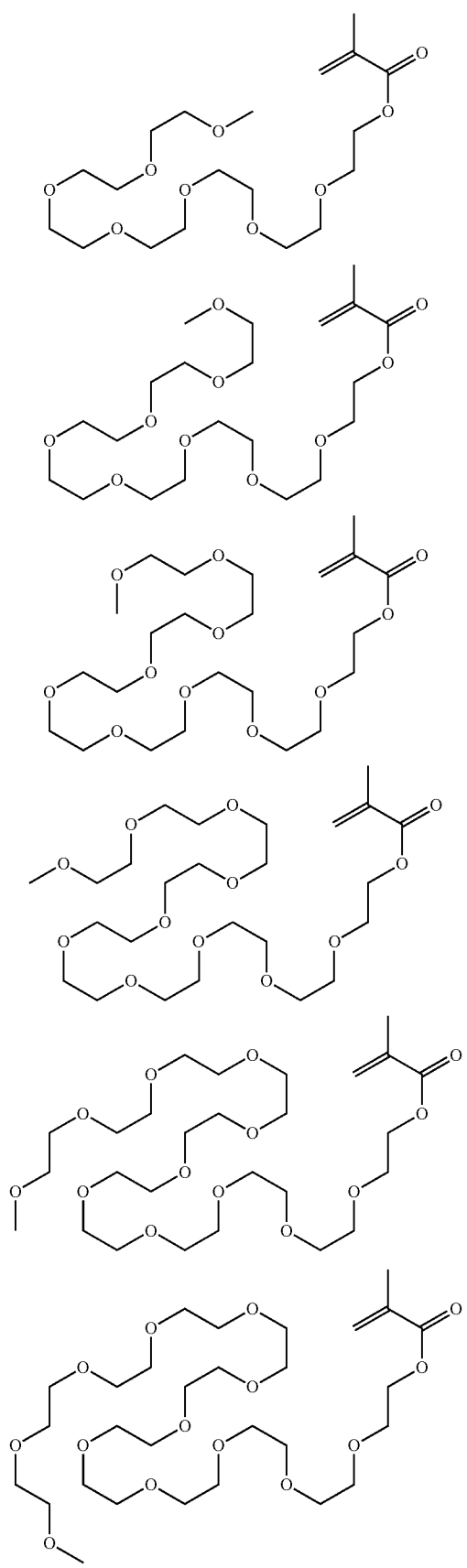
92
-continued
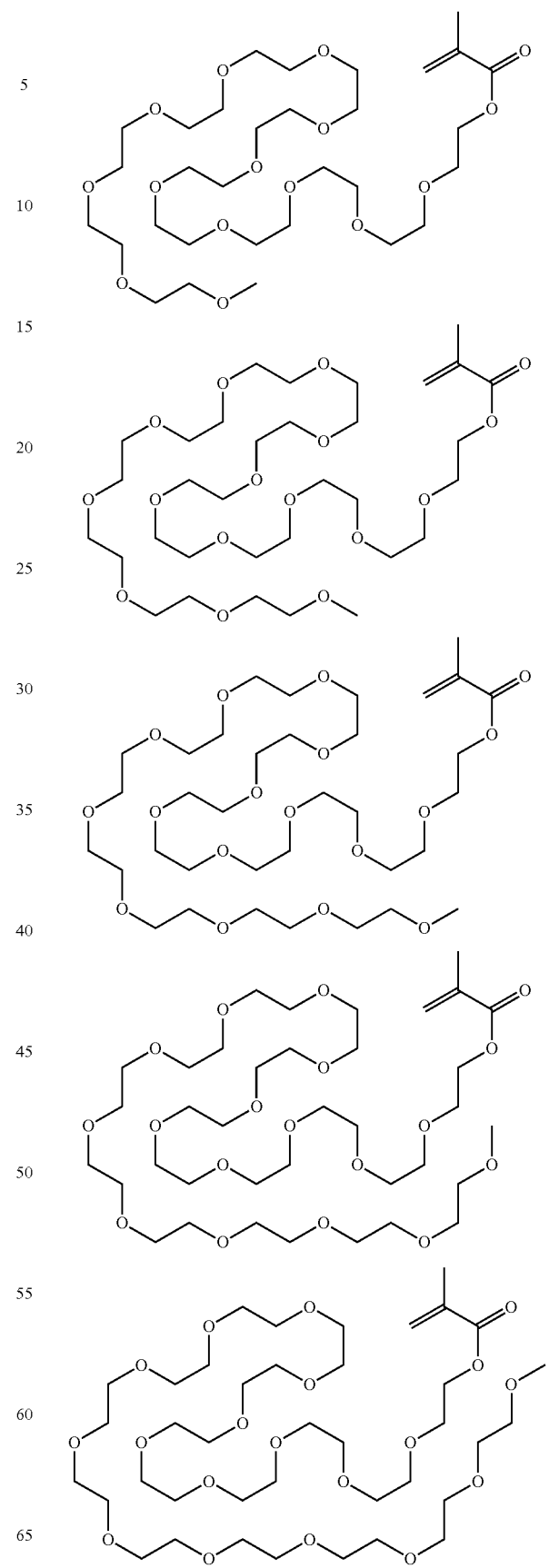

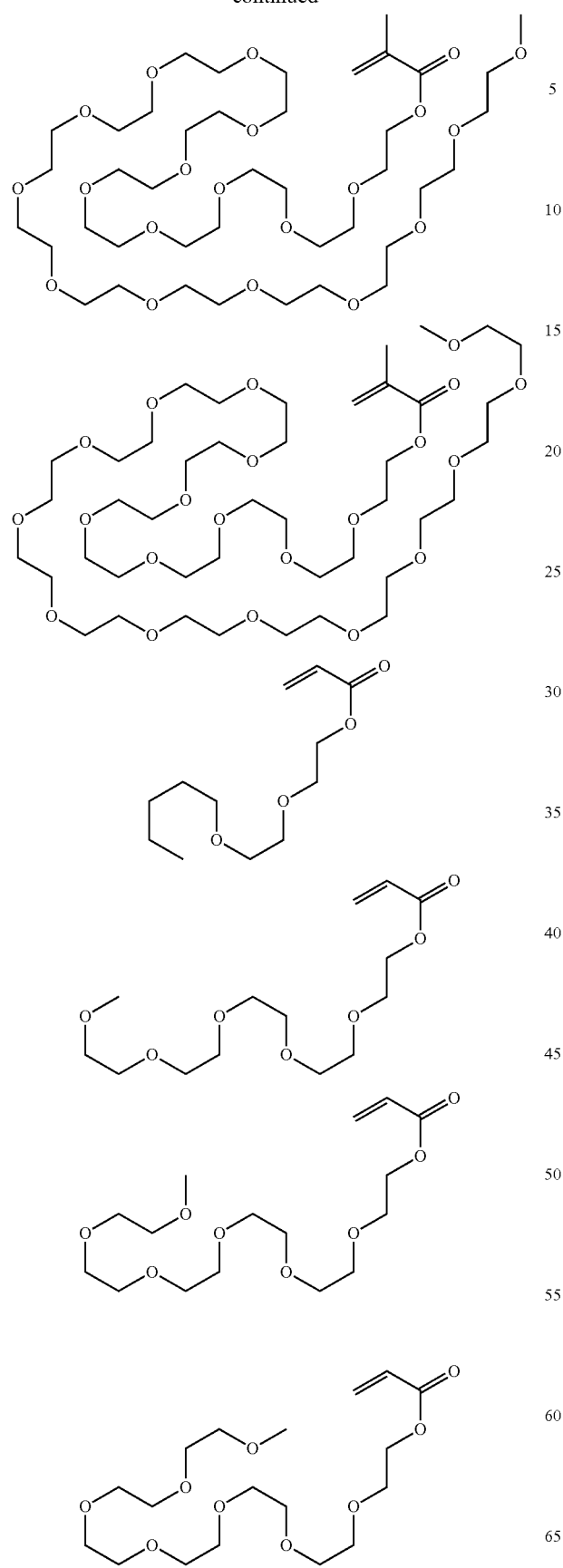
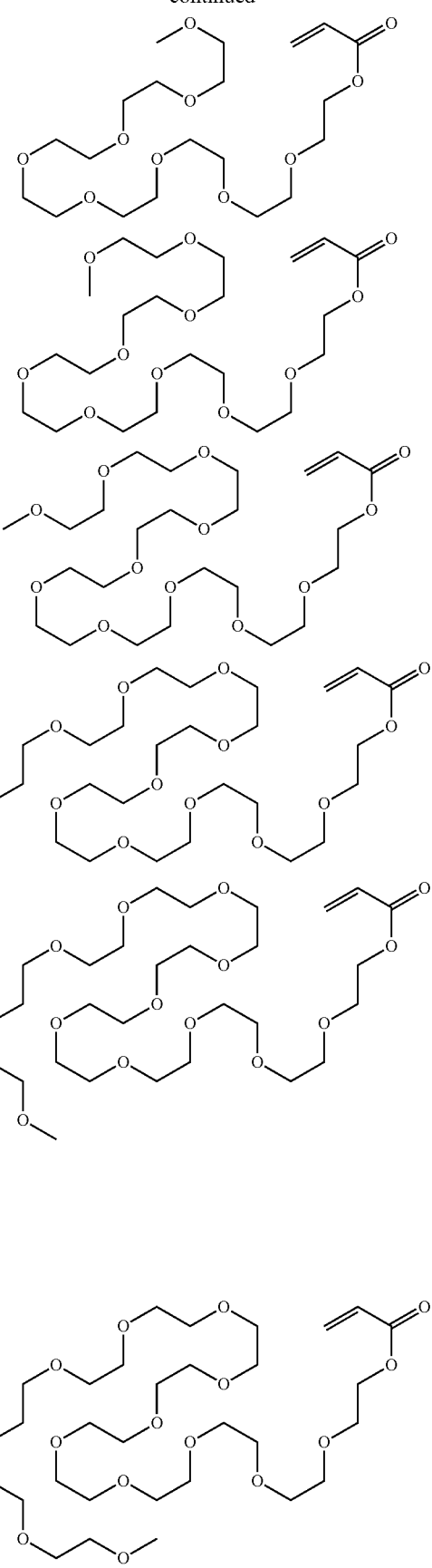

95
-continued
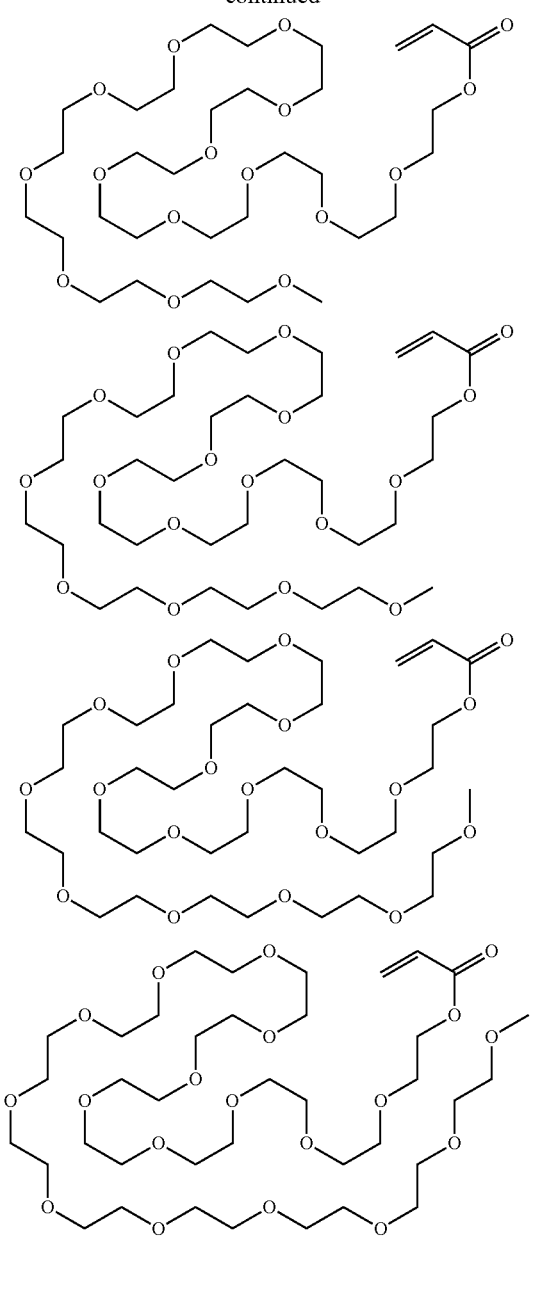
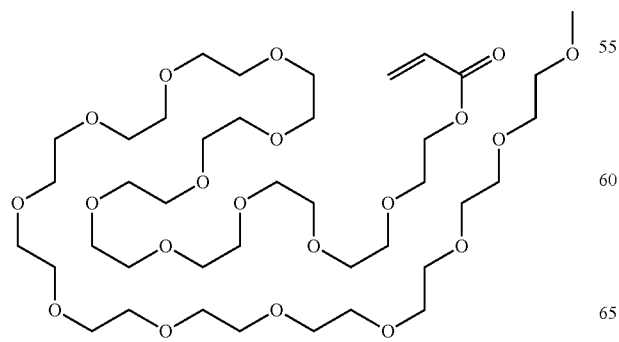
96
-continued
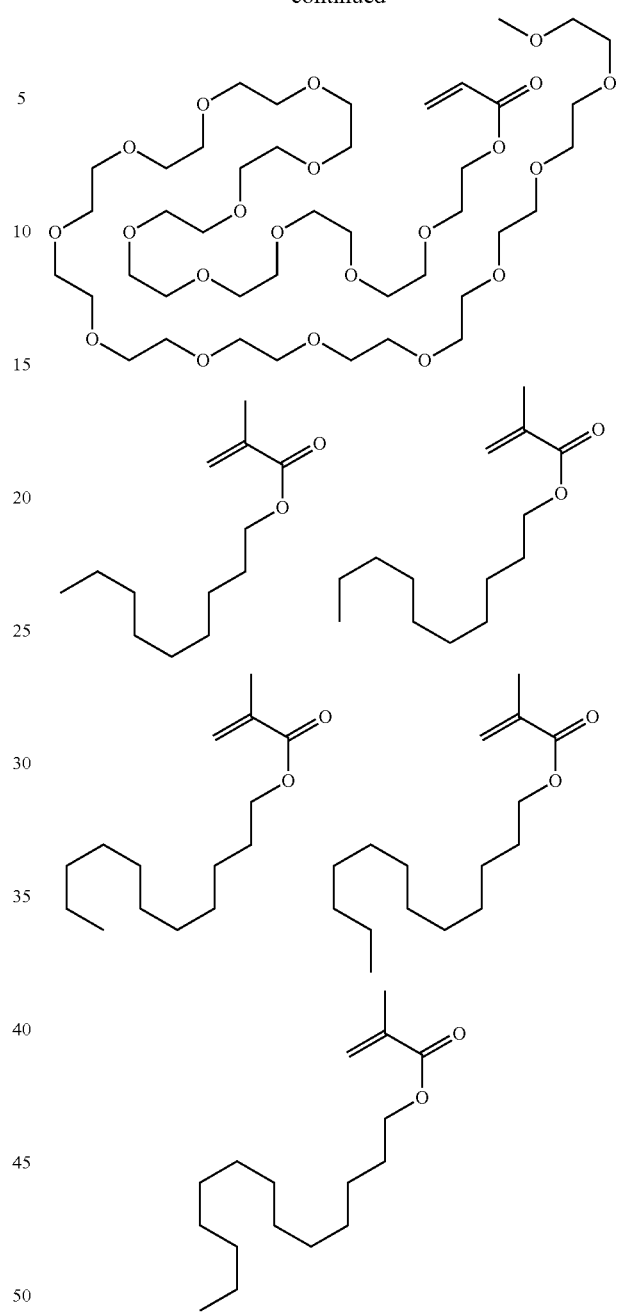
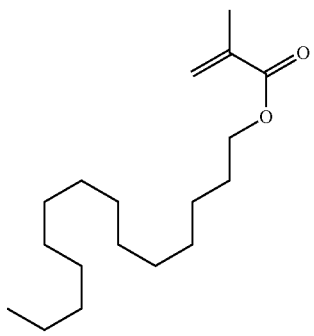

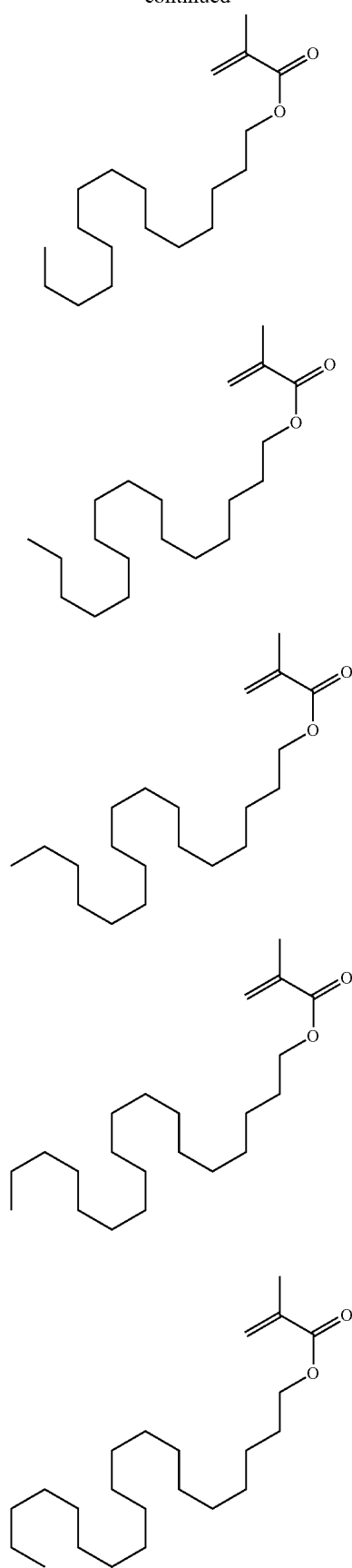
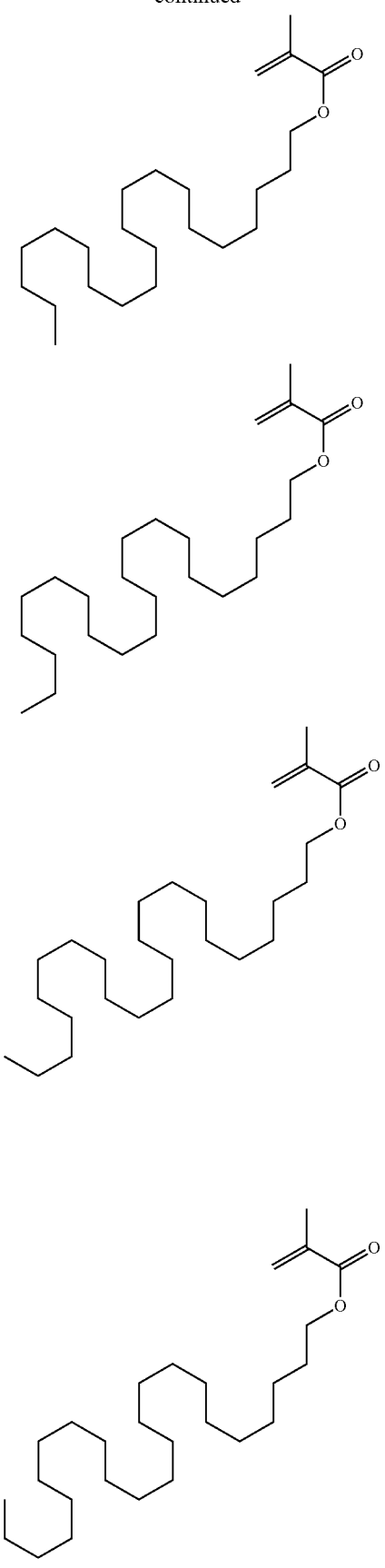

99
-continued
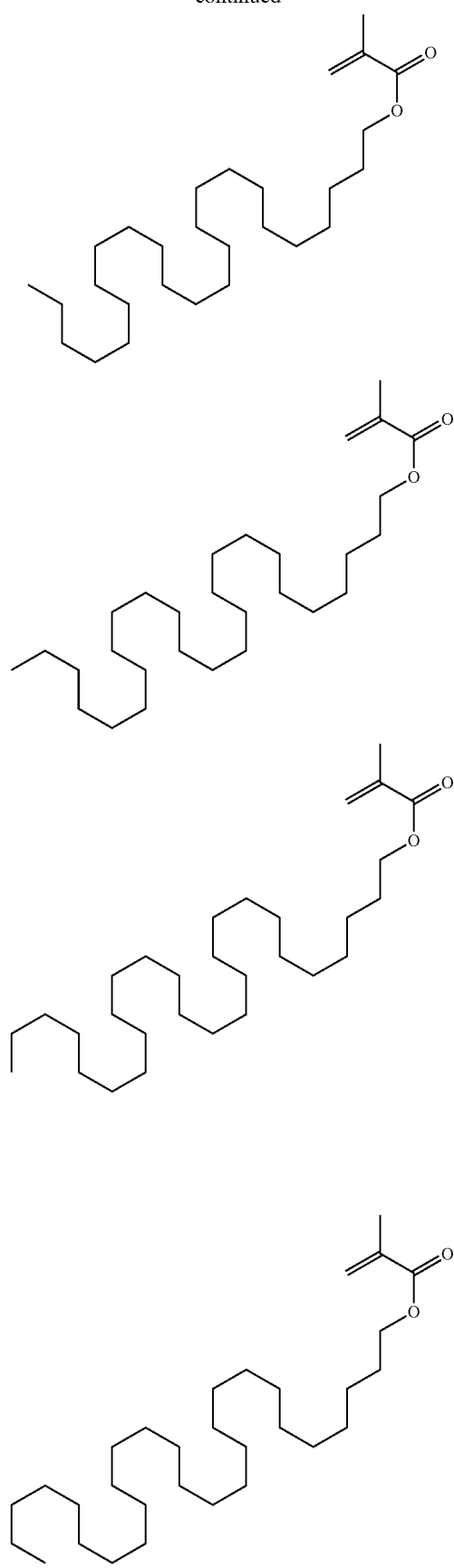
100
-continued
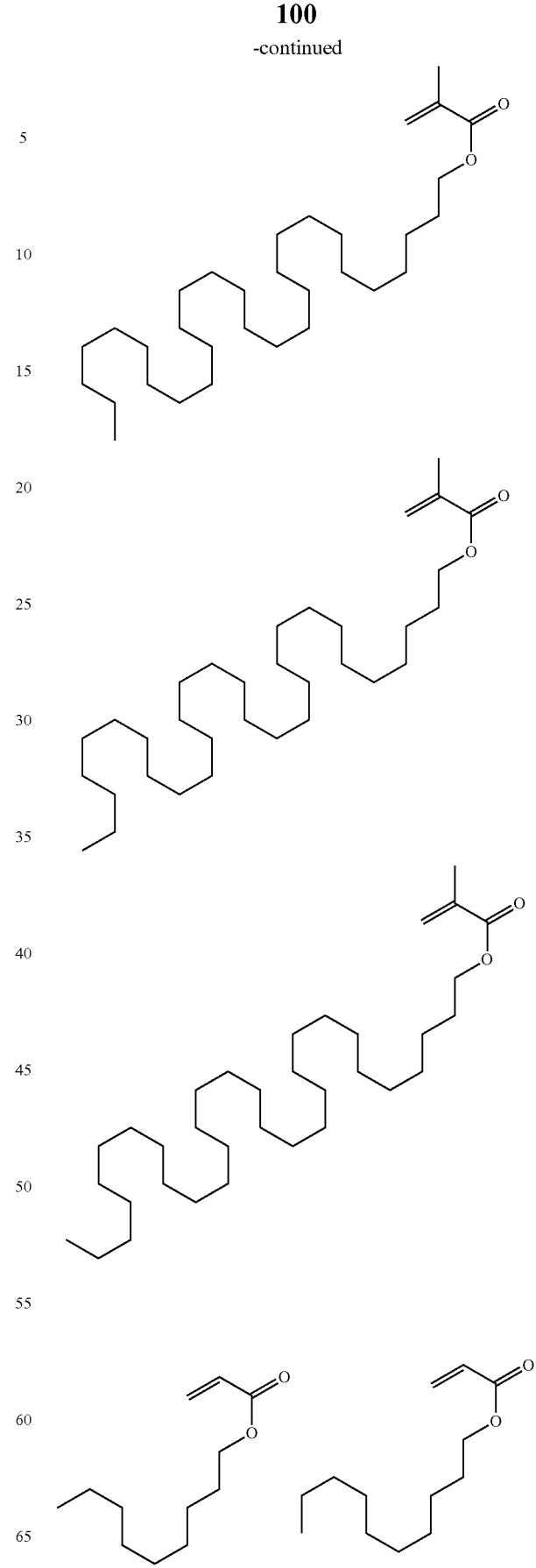

101
-continued
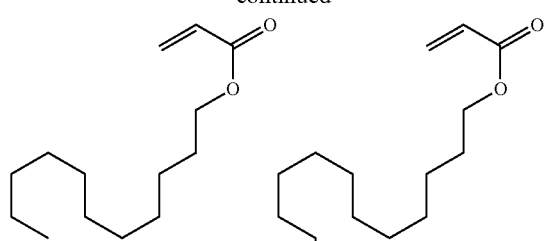
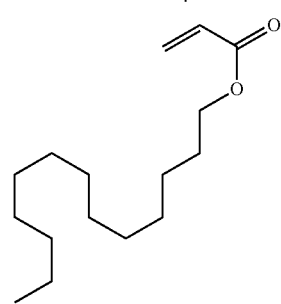
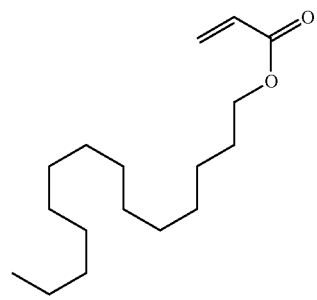
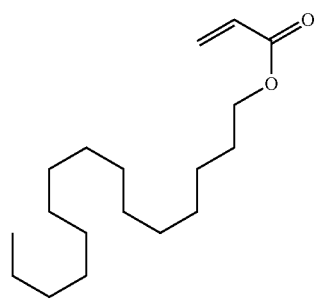
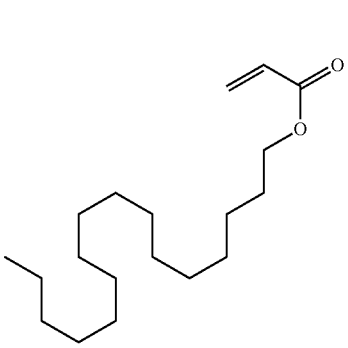
102
-continued
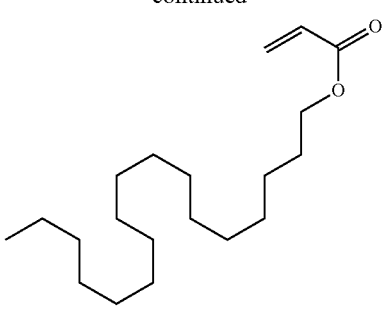
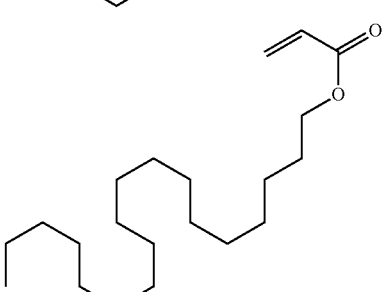
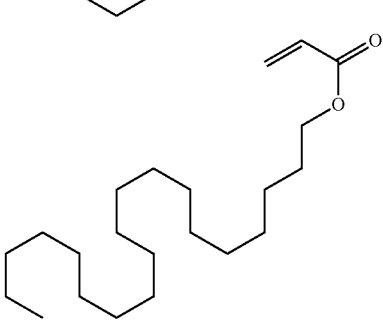
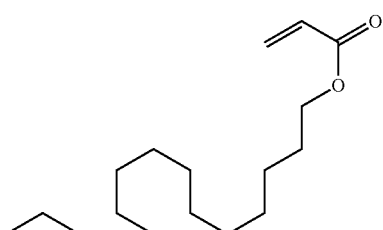
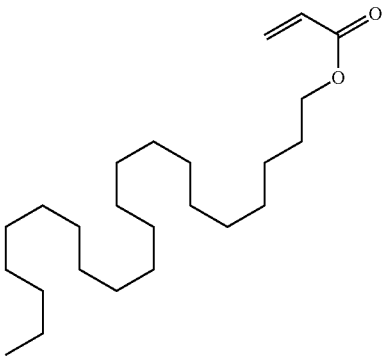

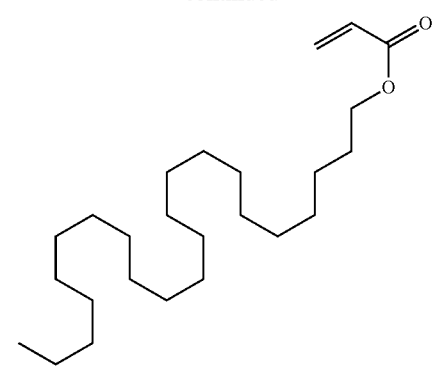
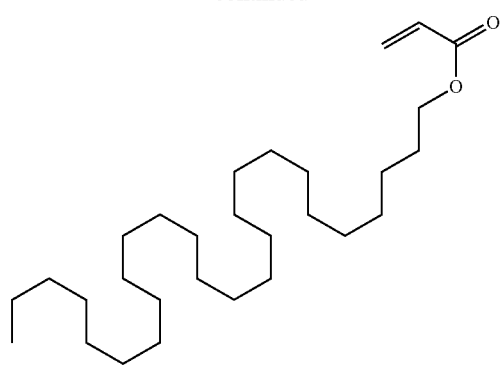

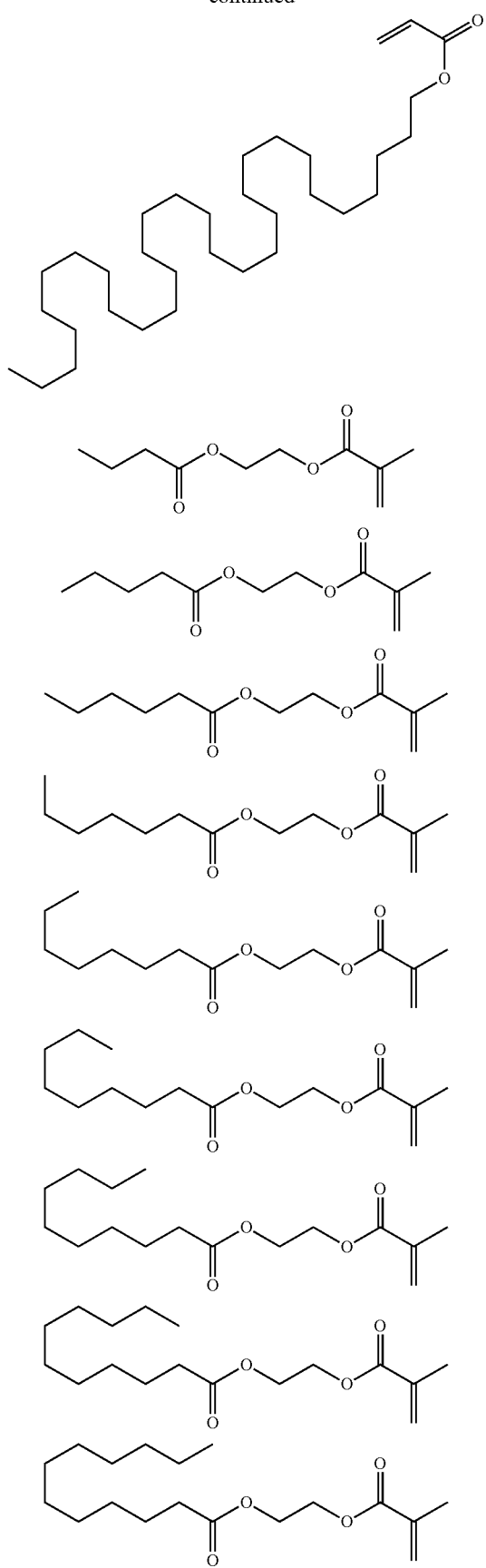
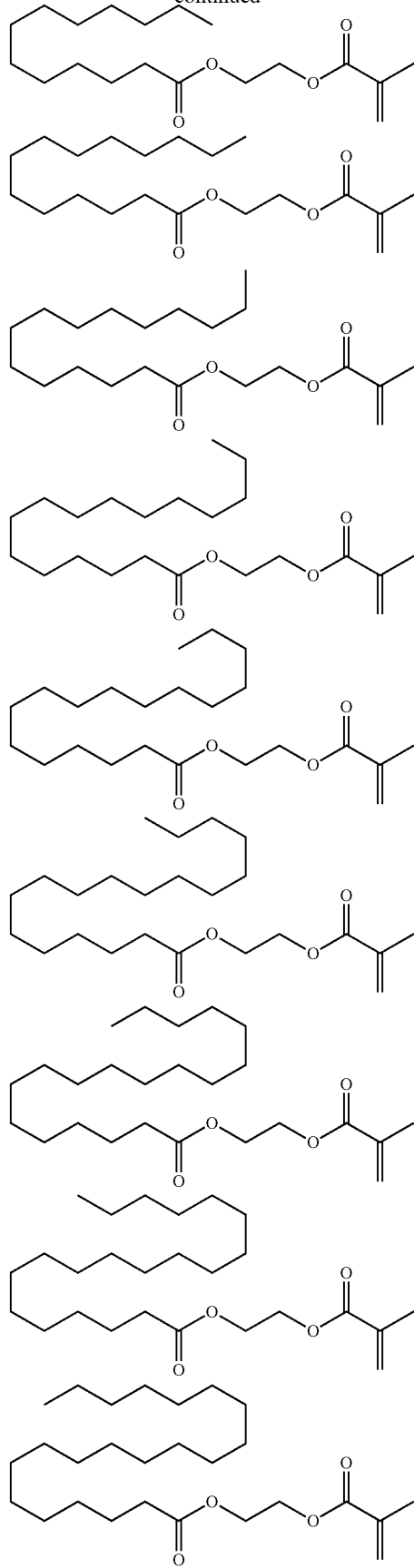

107
-continued
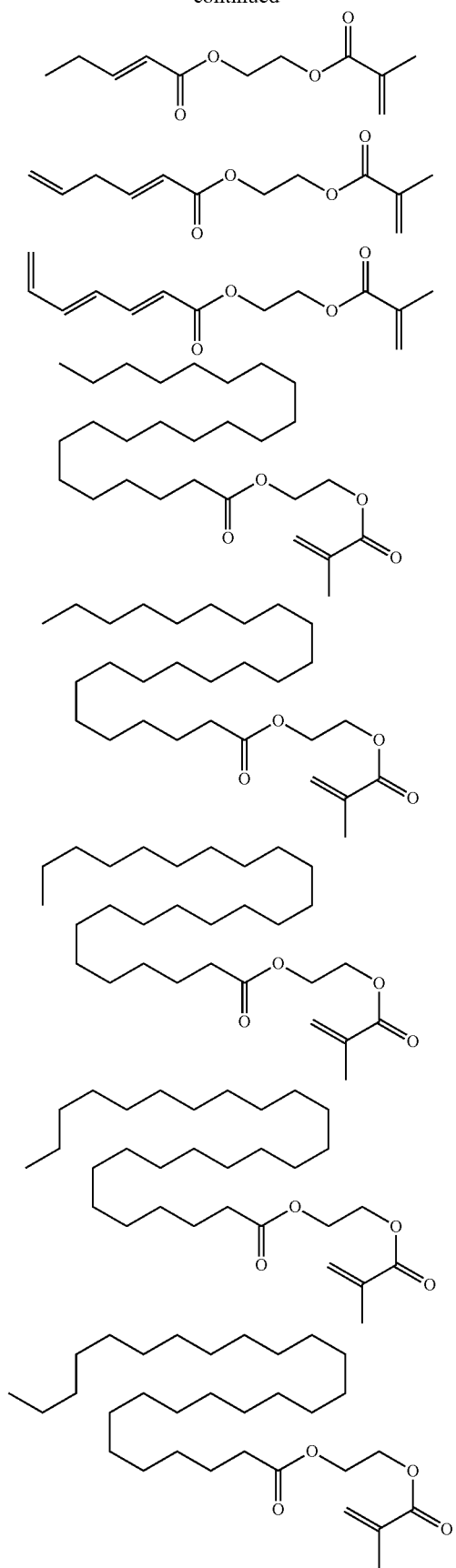
108
-continued
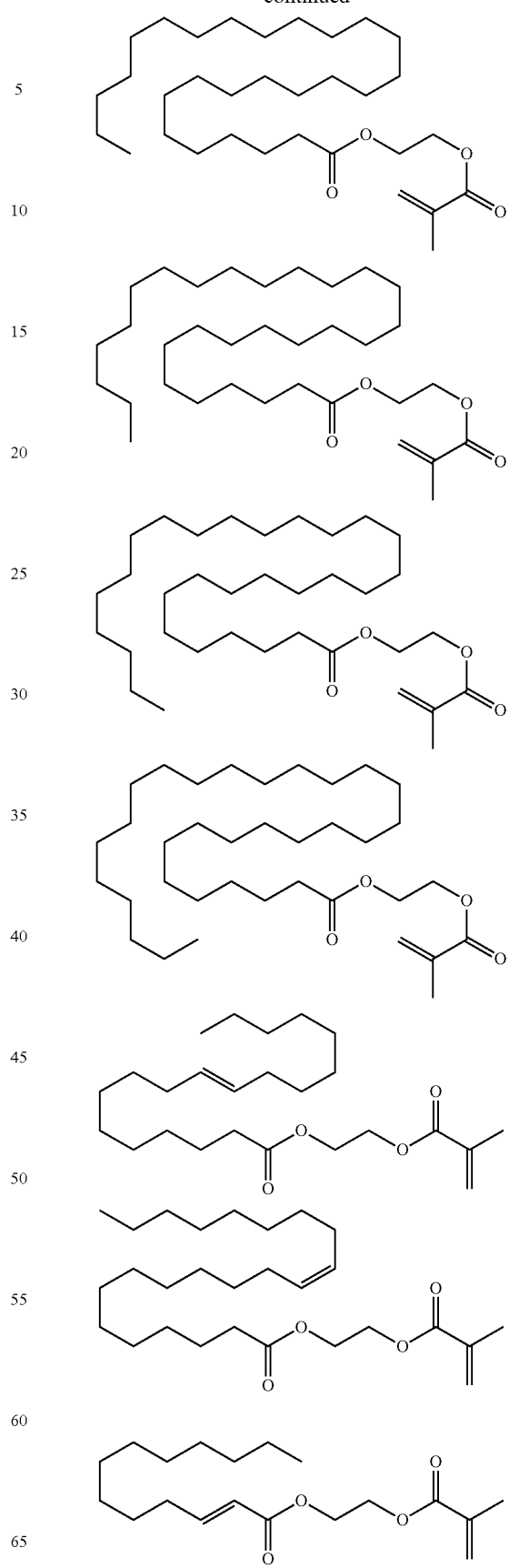

109

-continued

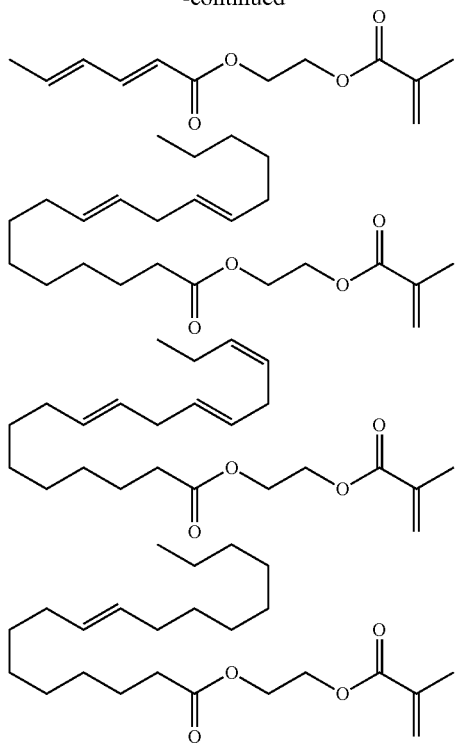

110

-continued

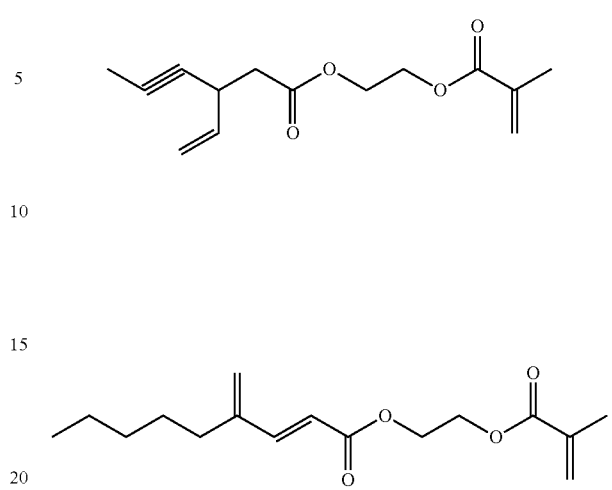

In order to give water repellency to the inventive bio-electrode composition, the polymer compound can be a copolymer in which a repeating unit C having a fluorine atom or a silicon atom is copolymerized. The monomer to give the repeating unit C having a fluorine atom or a silicon atom is not particularly limited, but illustrative examples thereof include the following.

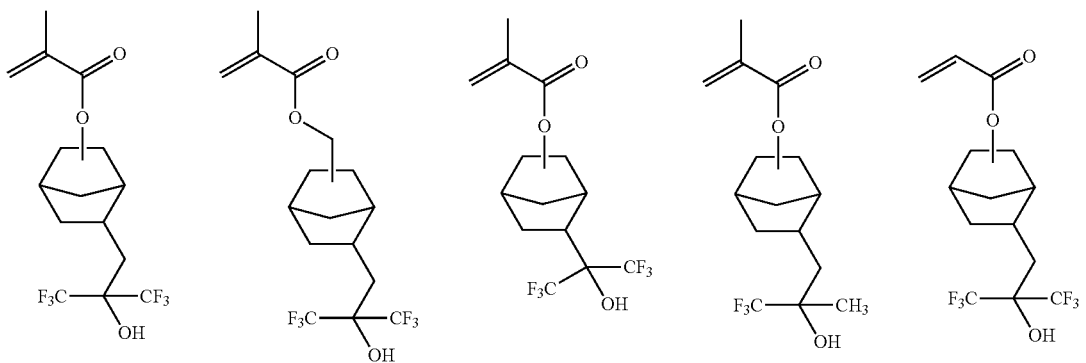

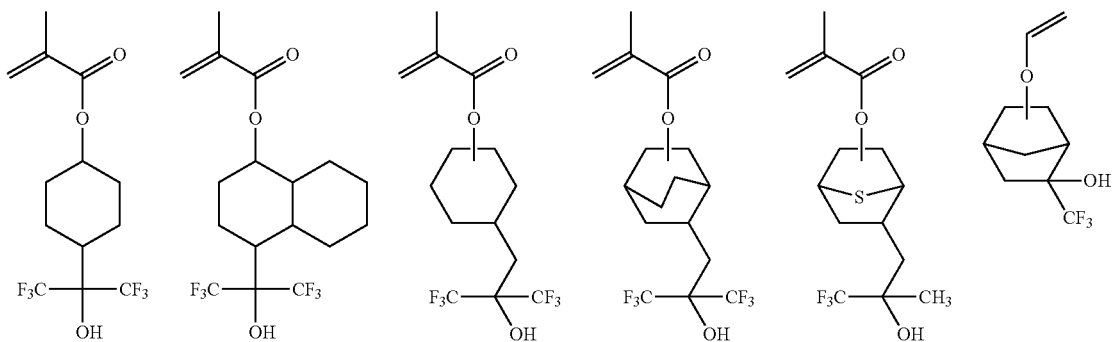

111  -continued  112
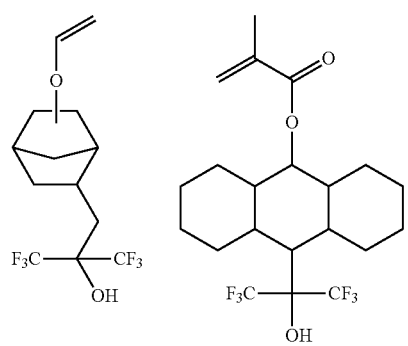 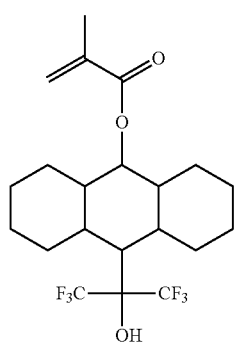 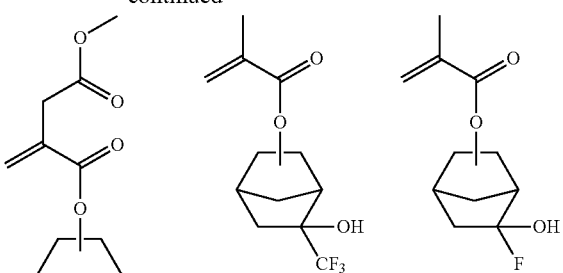 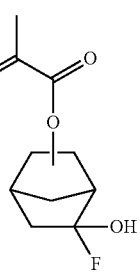
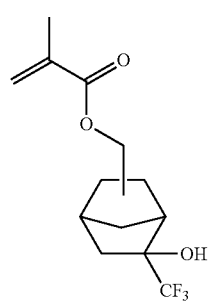 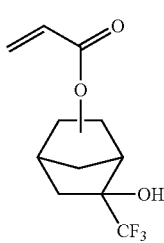 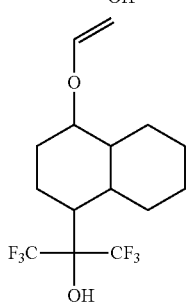 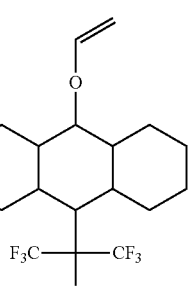 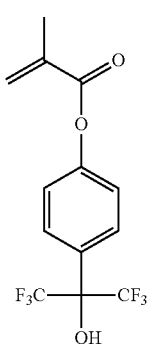
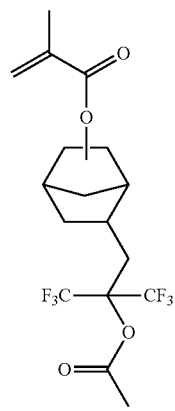 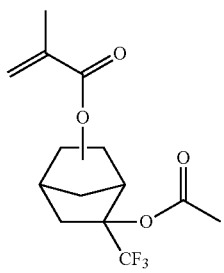 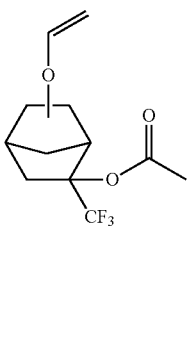 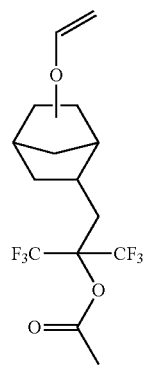 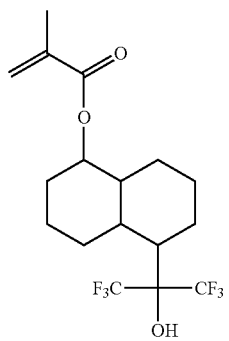
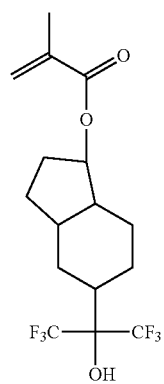 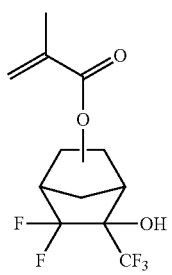 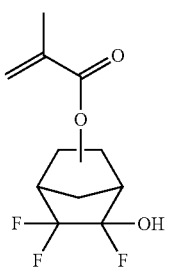 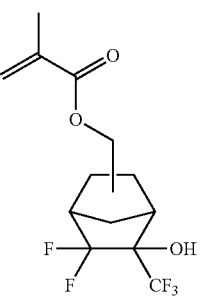 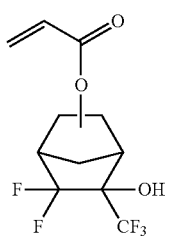

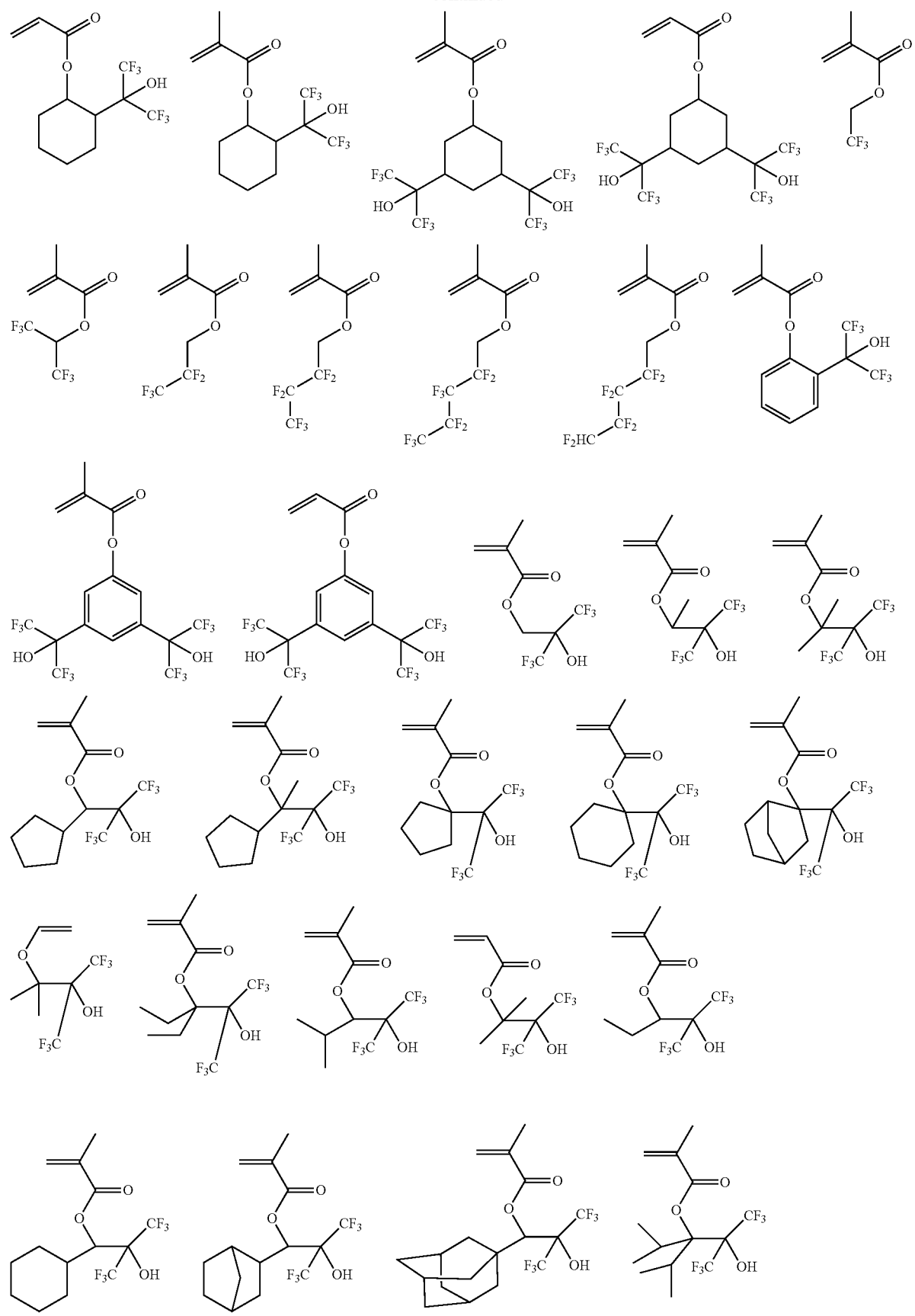

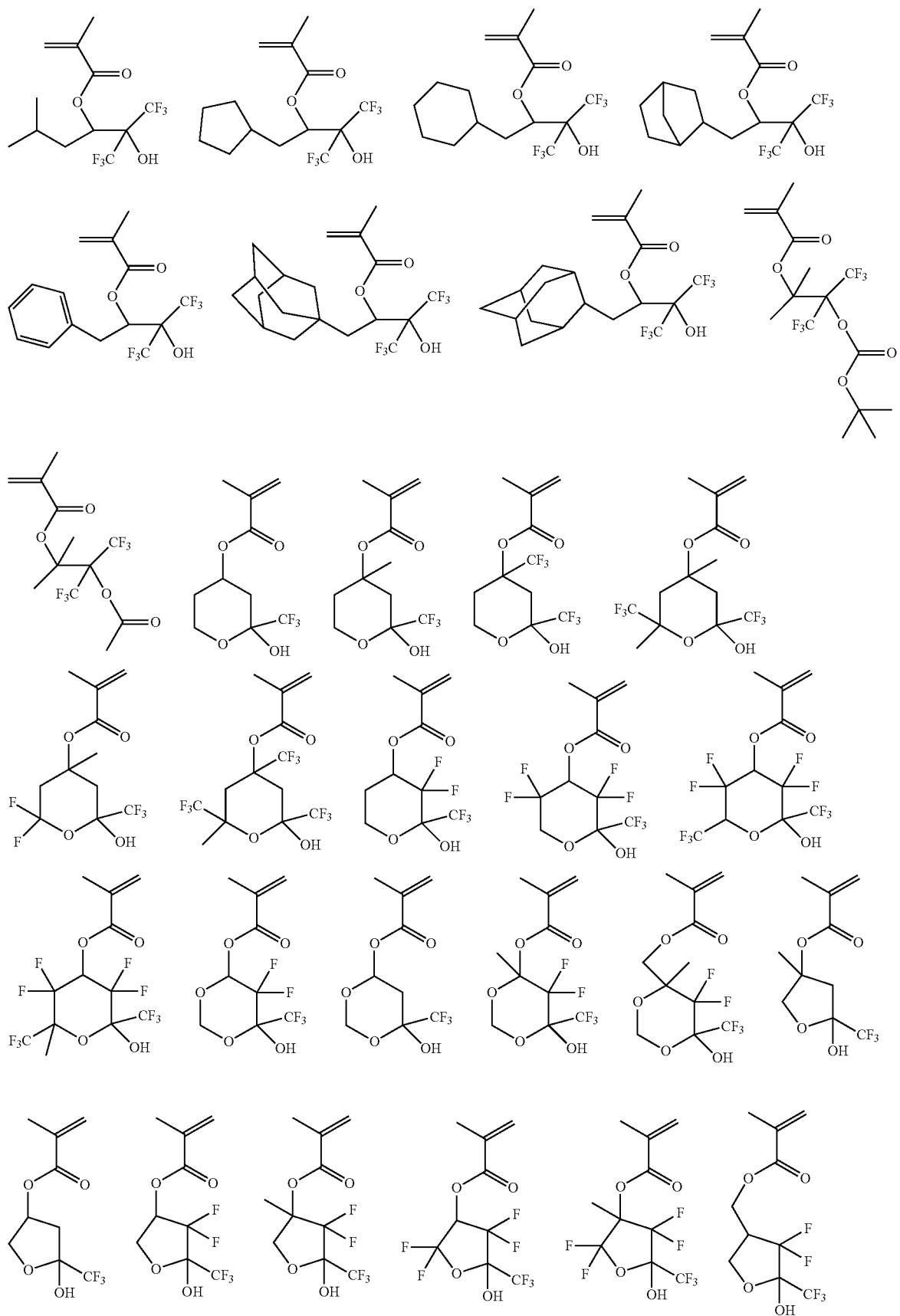

-continued
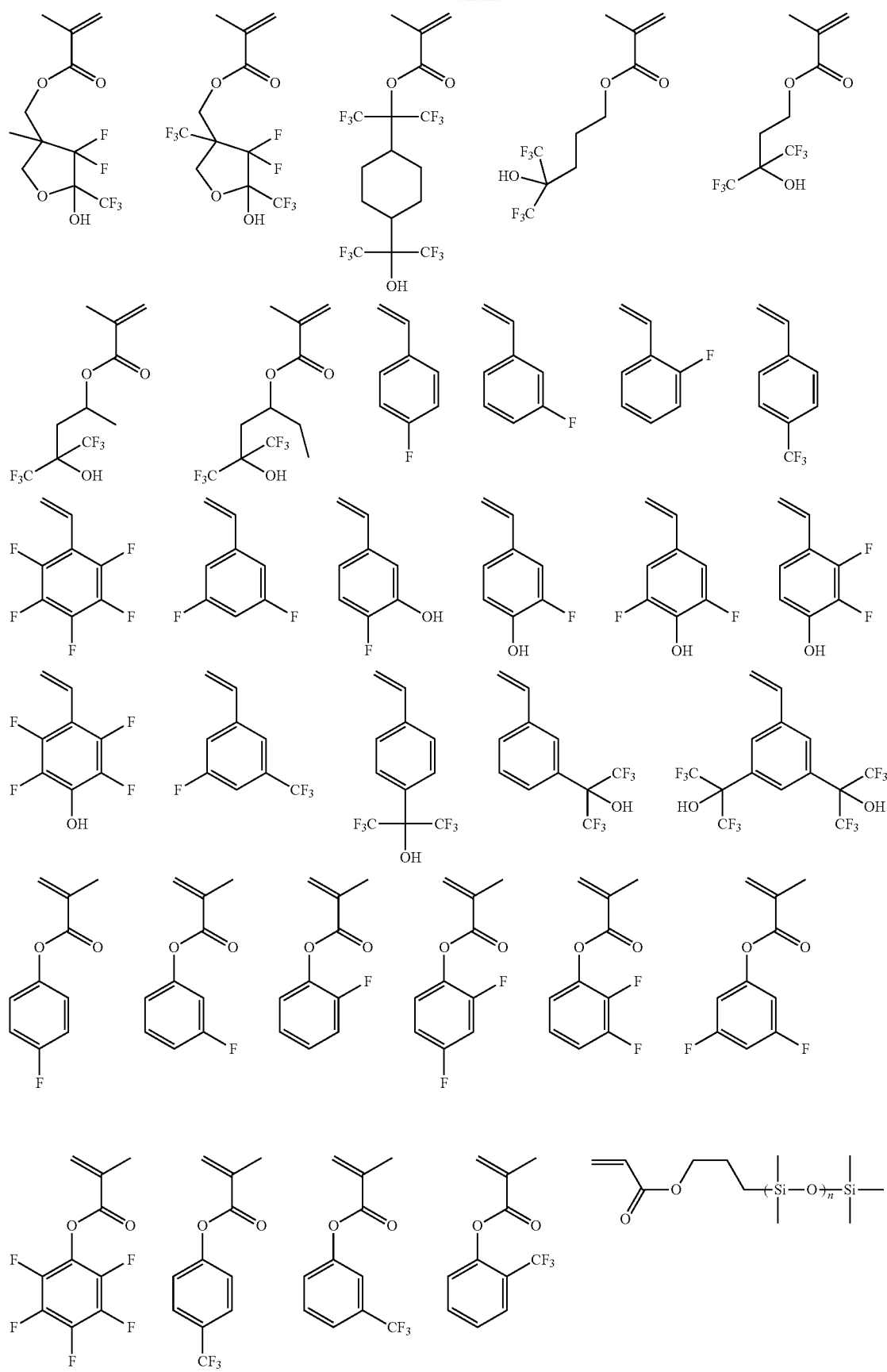

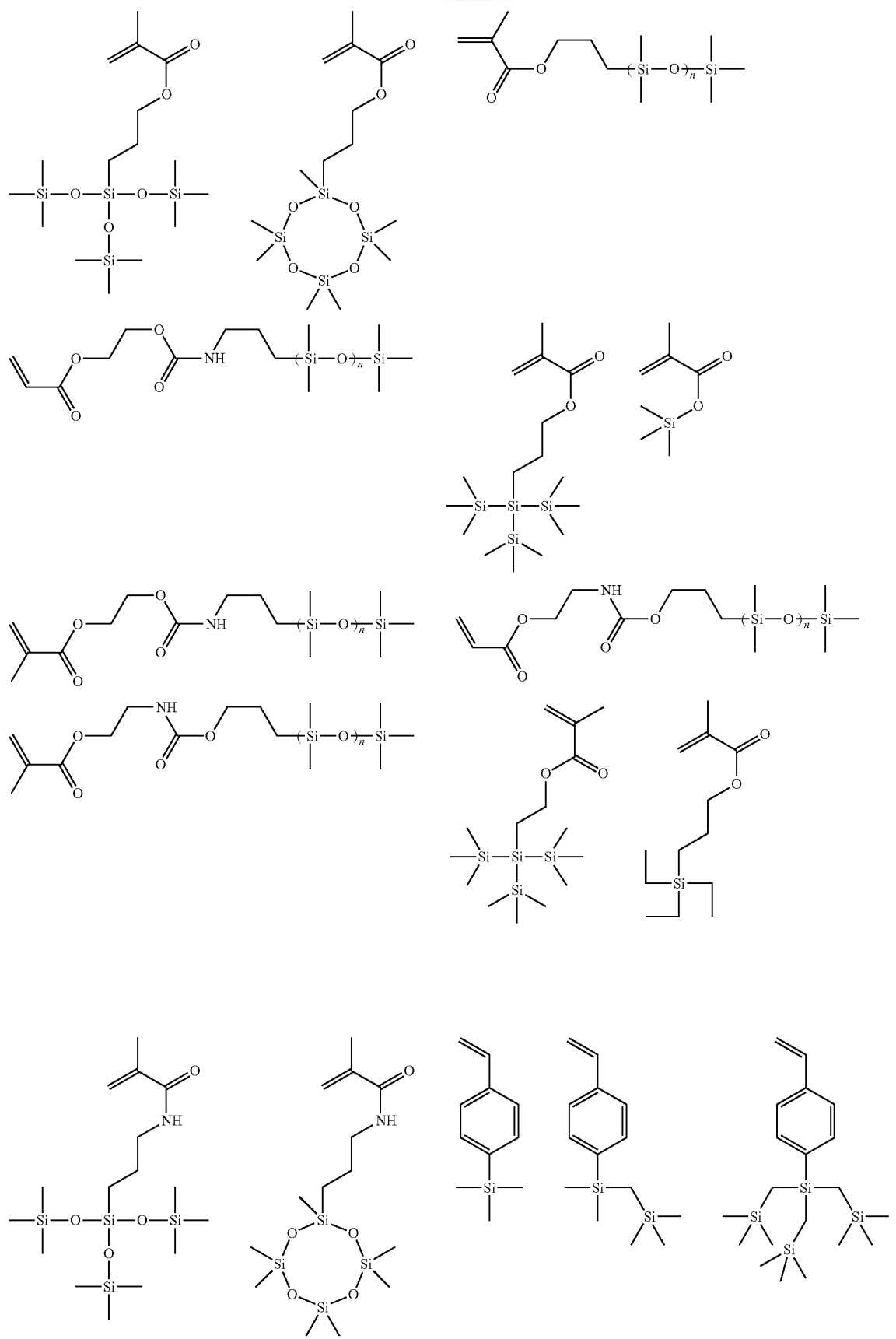
-continued

121
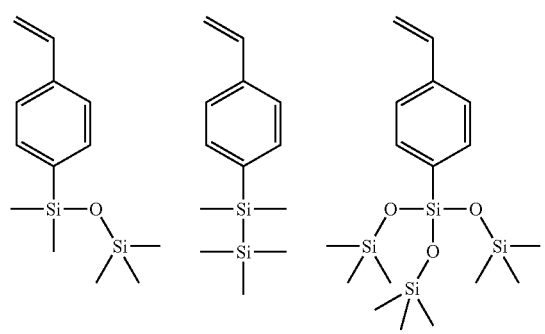
122
-continued
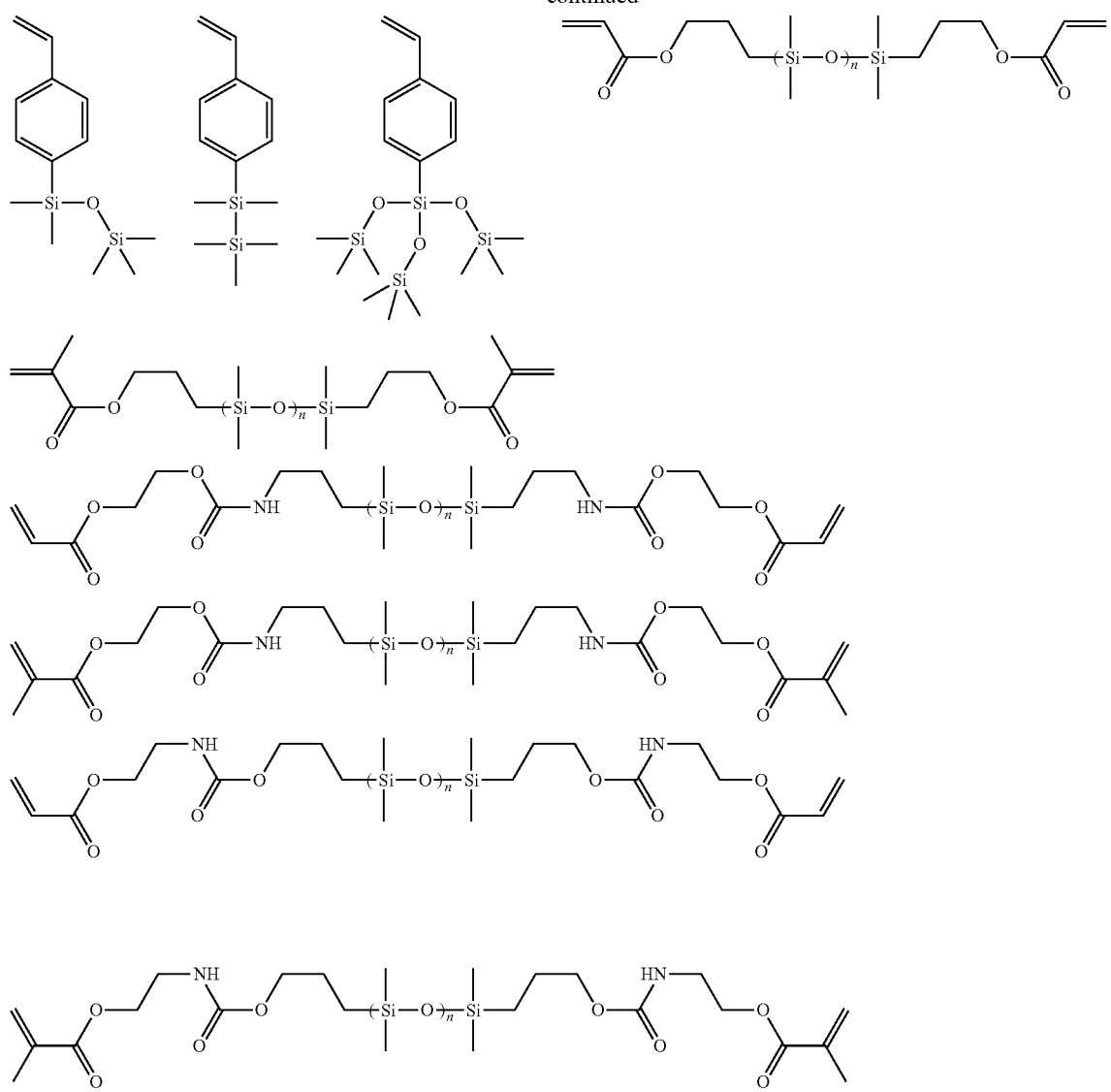
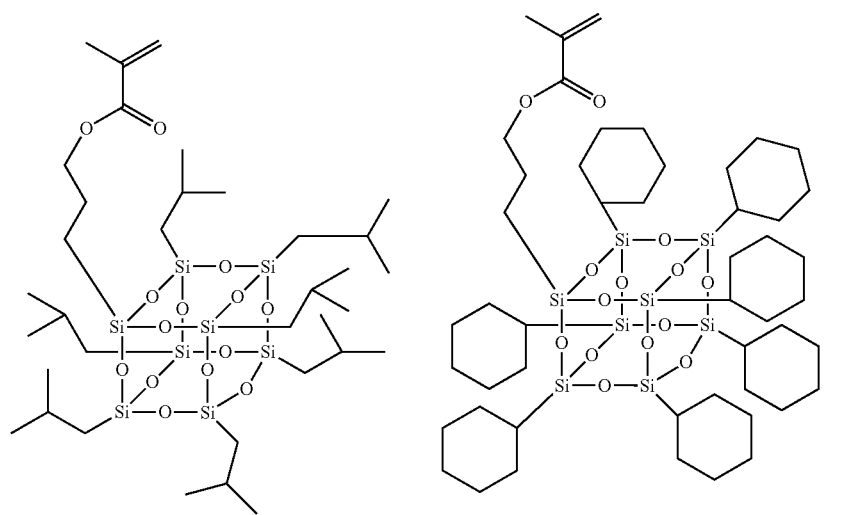

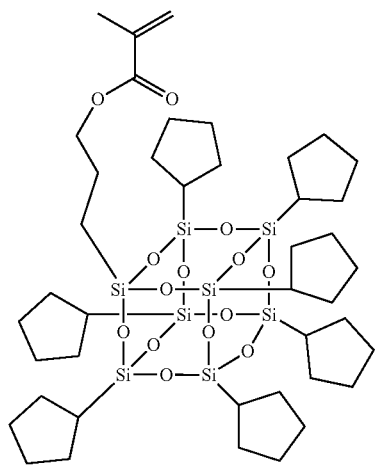

In the formulae, "n" is an integer of 0 to 100.

In the polymer compound, it is also possible to copolymerize a repeating unit D, which is crosslinkable, having one or more groups selected from the group consisting of a hydroxy group, a carboxy group, an oxirane group, and an oxetane group. The monomer to give the crosslinkable repeating unit D is not particularly limited, but illustrative examples thereof include the following.

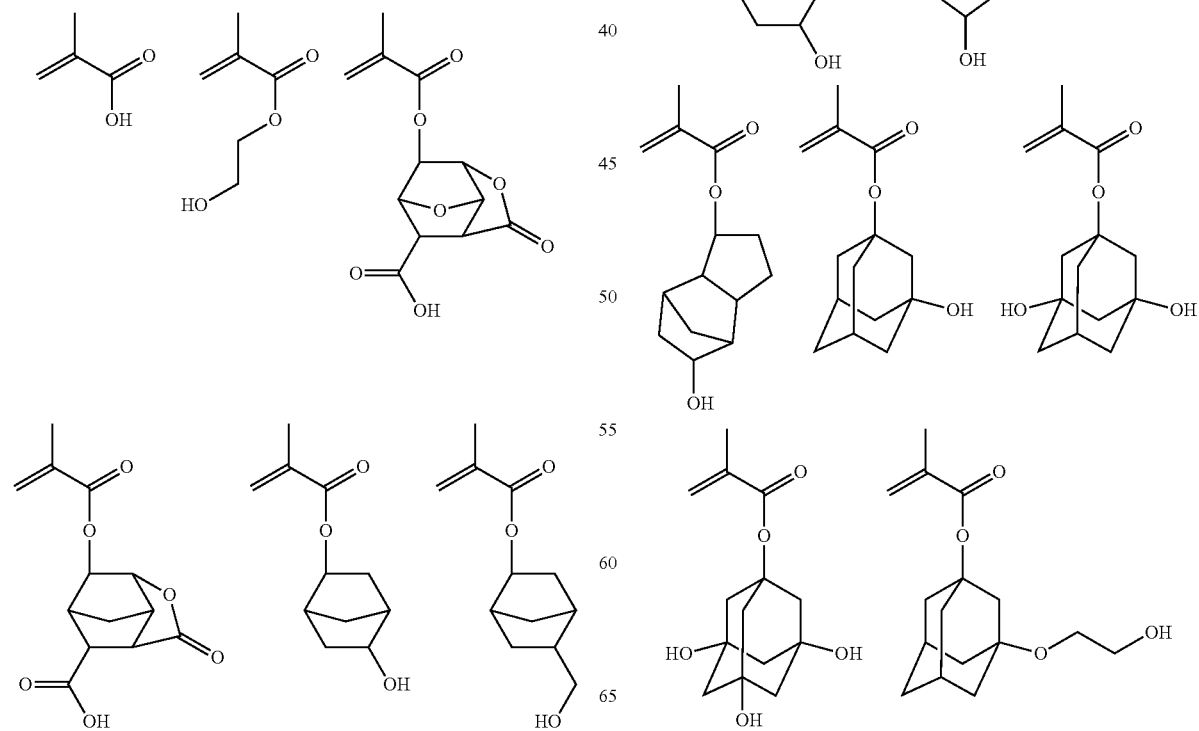

125
-continued
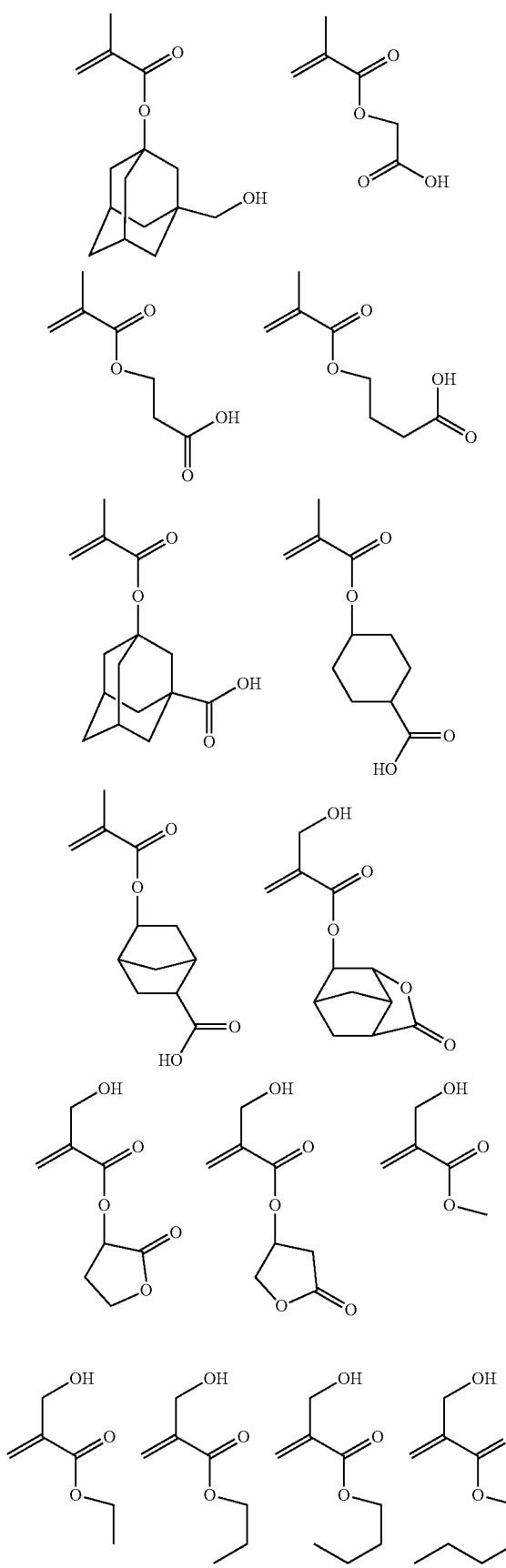
126
-continued
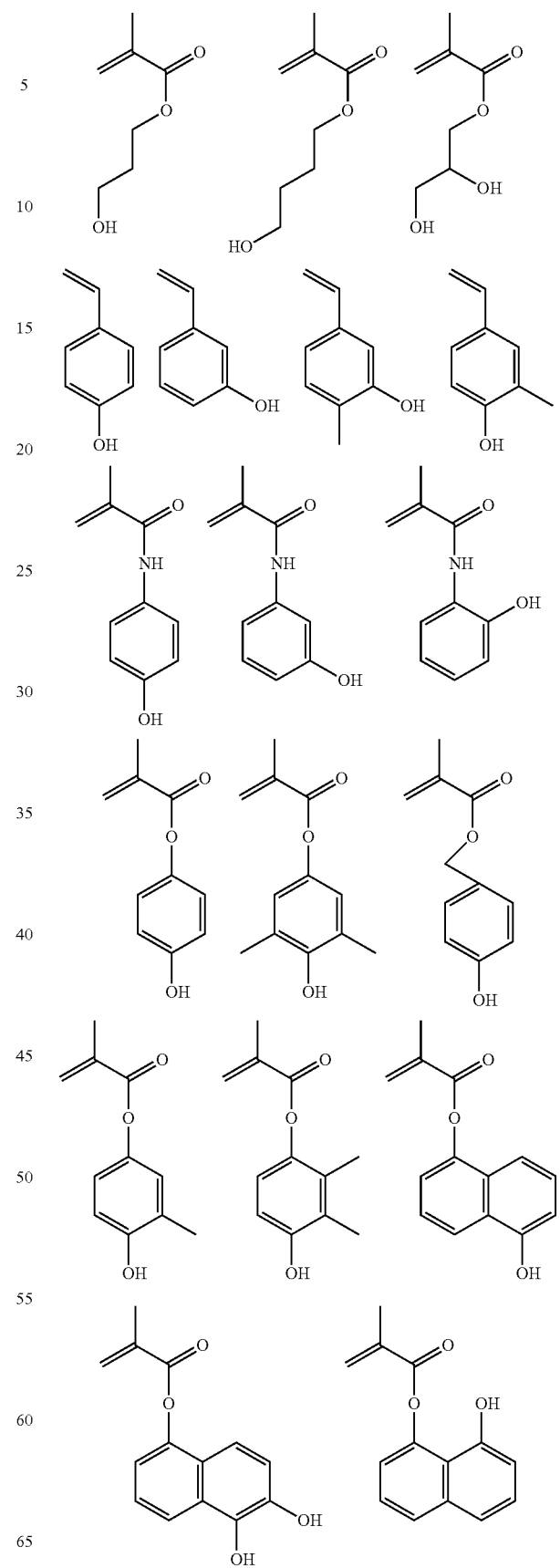

127
-continued
128
-continued
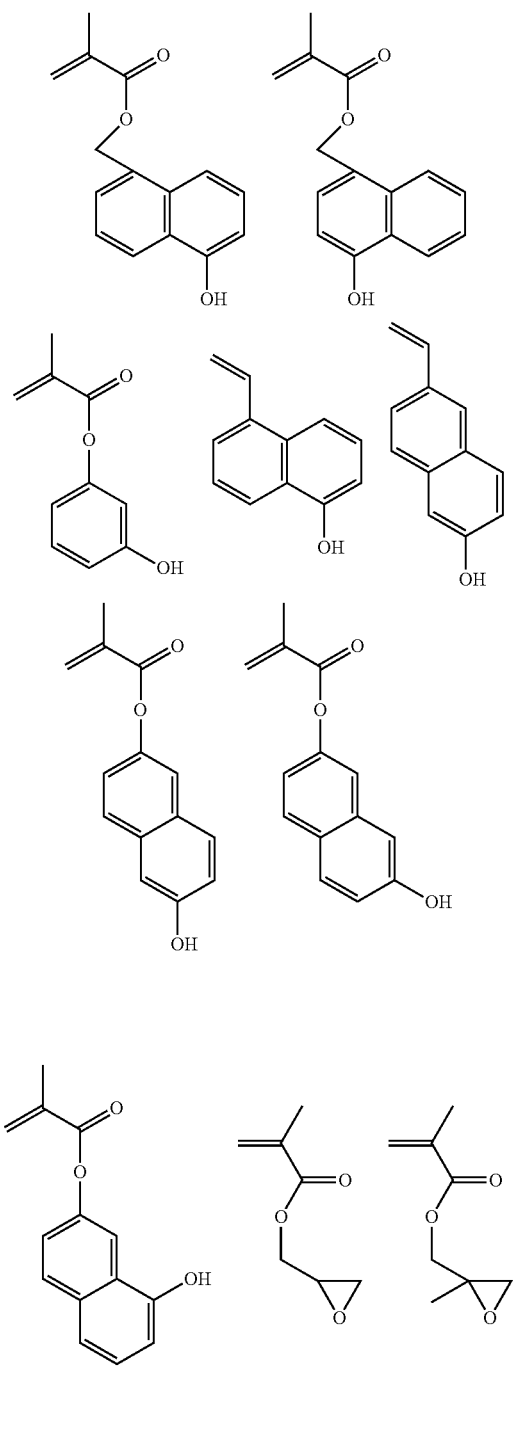
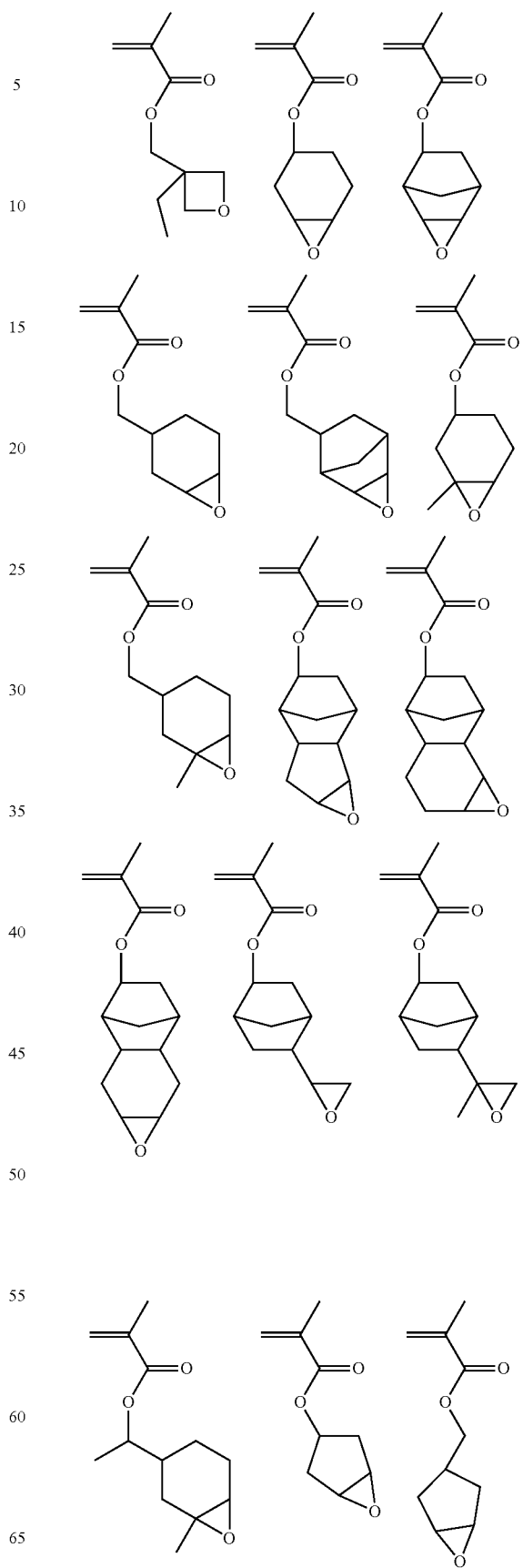

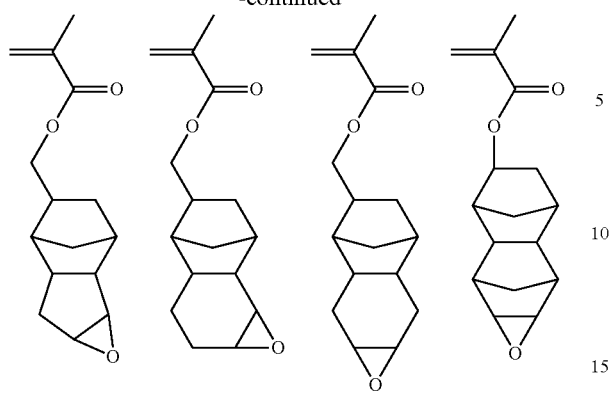
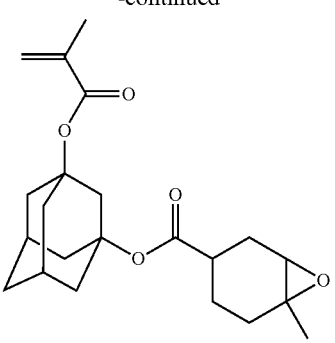
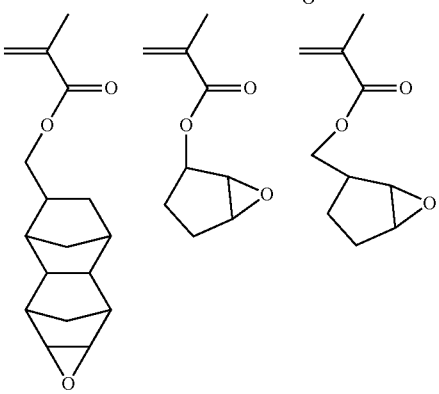
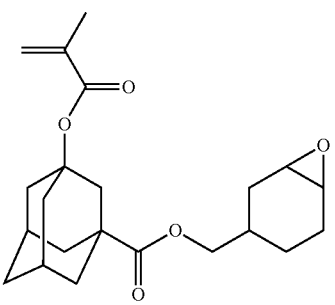
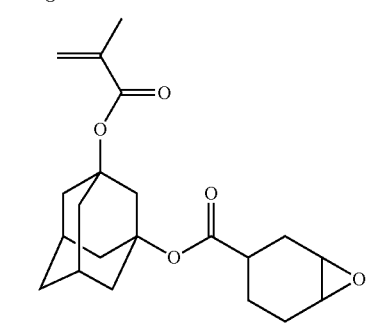
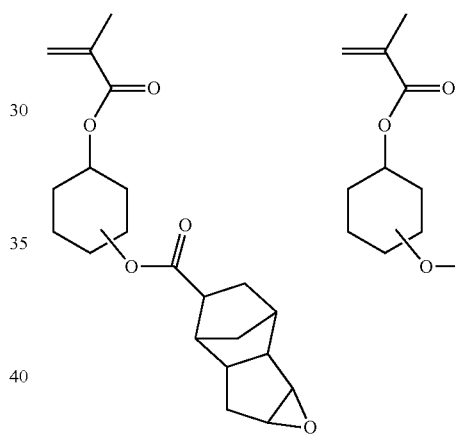
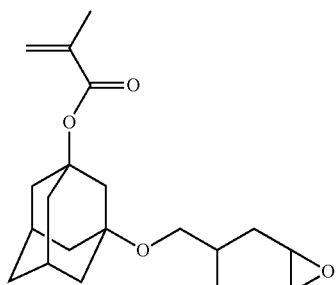
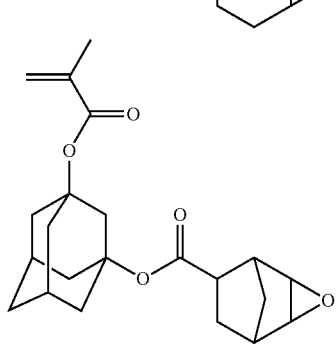
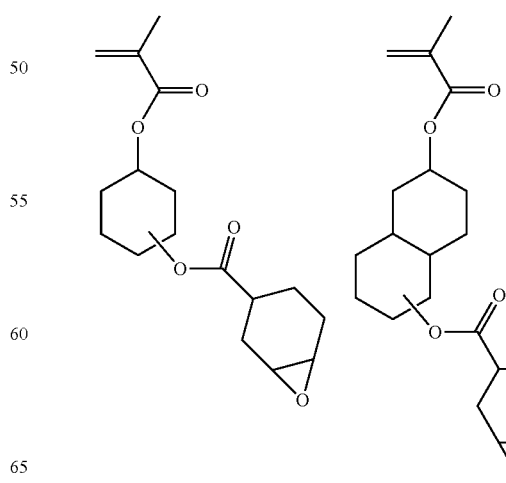

131
-continued

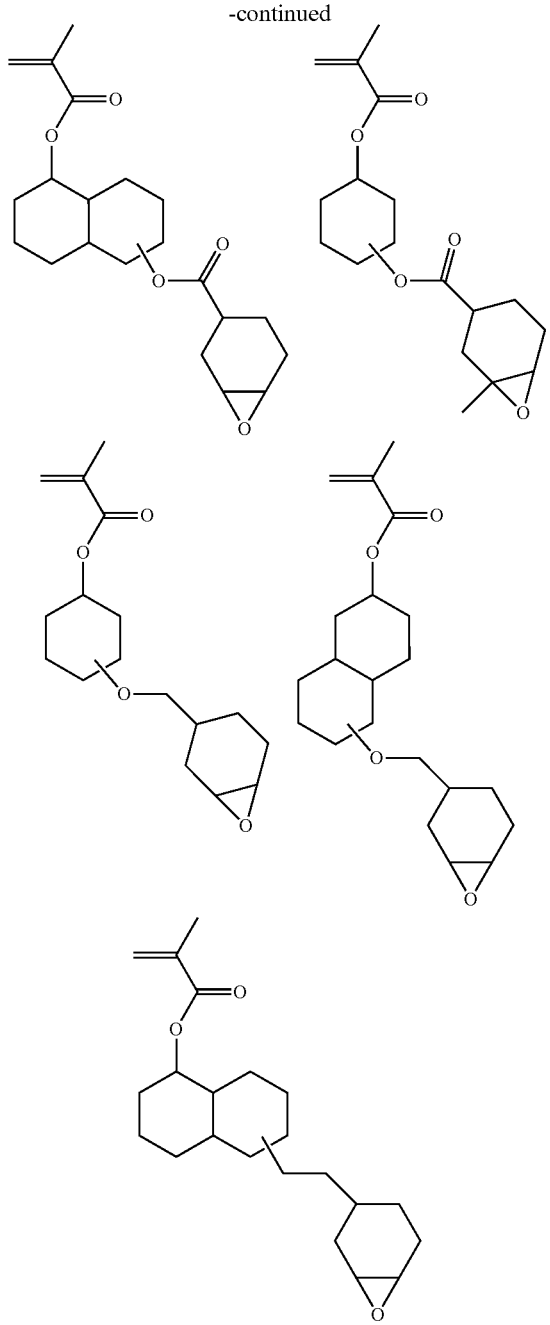

132
-continued

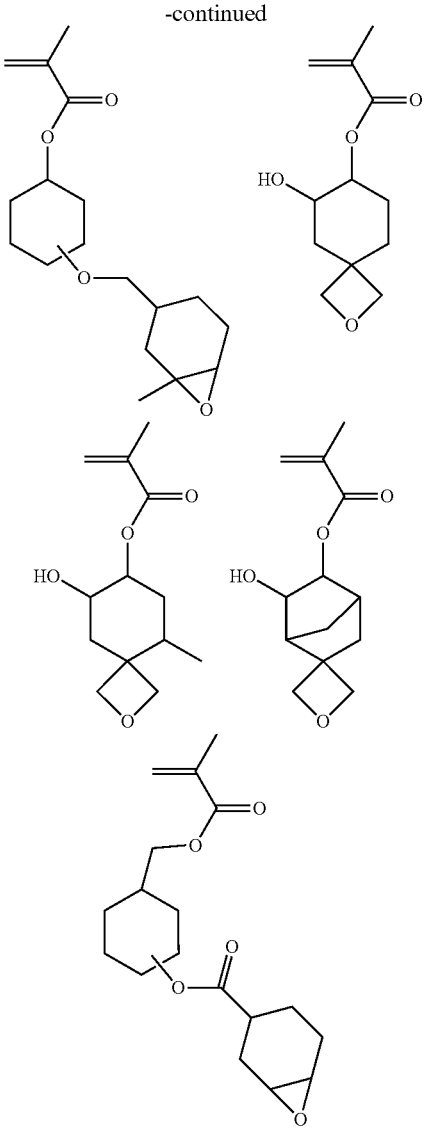

In addition, it is also possible to copolymerize a repeating unit E having a polymerizable double bond. This allows crosslinking between polymers after the polymerization. The monomer that has plurality of polymerizable double bonds to give the repeating unit E, which has a polymerizable double bond, is not particularly limited, but illustrative examples thereof include the following.

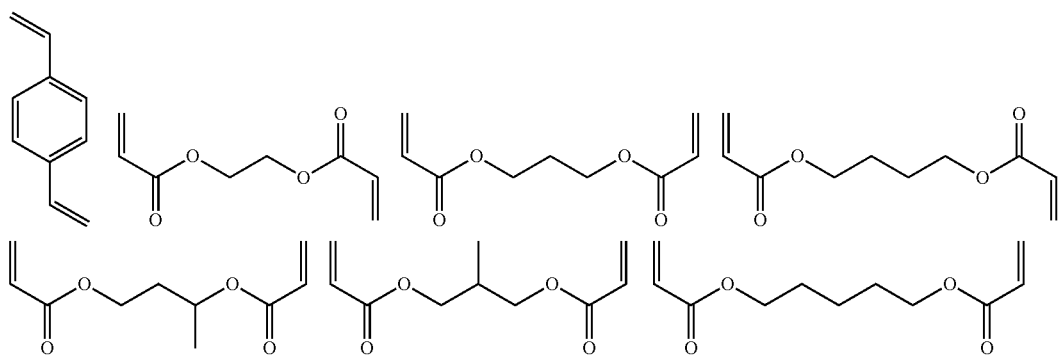

-continued
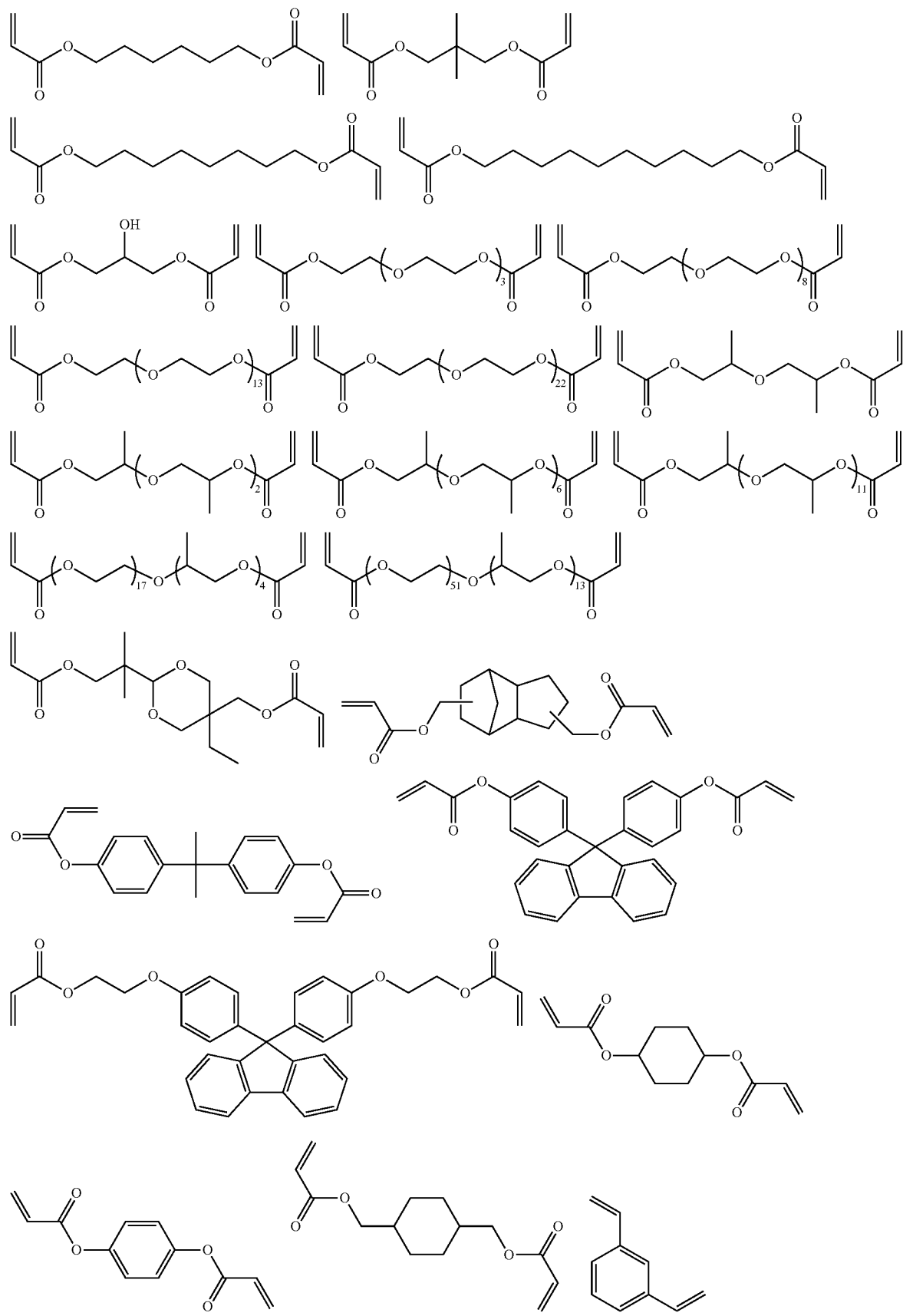

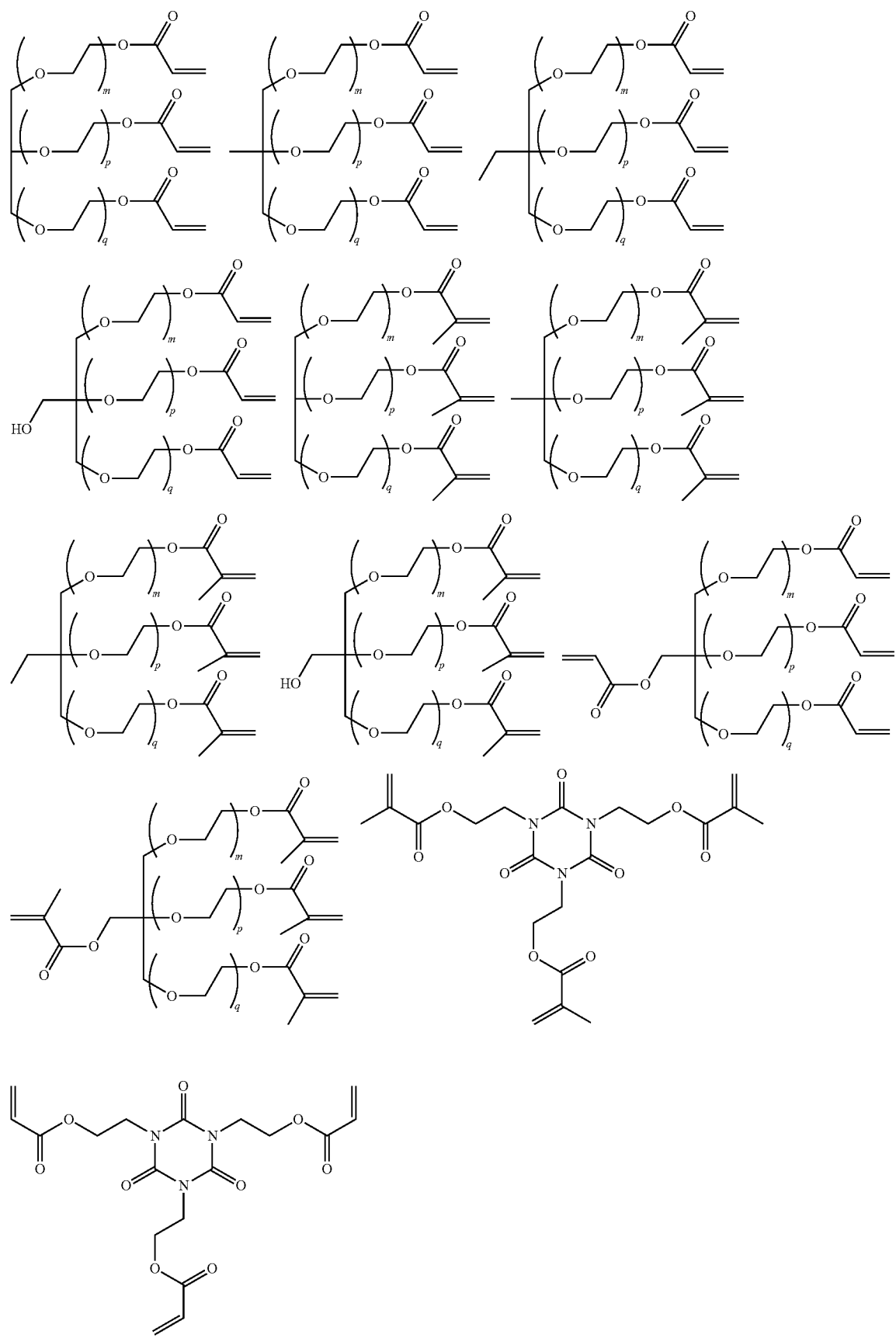

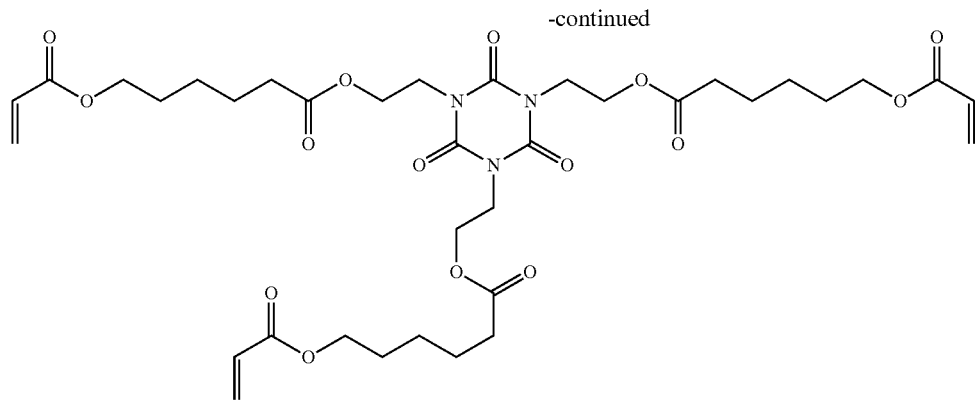

In the formulae, "m", "p", and "q" satisfy $3 \leq m+p+q \leq 30$.

The polymer compound like this can be produced by a synthesis method such as a heat polymerization method in which the copolymer compound is obtained by heat polymerization of a desired monomer having one or more repeating units A1 to A7, selected from monomers to give the repeating units A1 to A7, B, C, D, and E, in an organic solvent by adding radical polymerization initiator.

Illustrative examples of the organic solvent used in the polymerization include toluene, benzene, tetrahydrofuran, diethyl ether, and dioxane. Illustrative examples of the radical polymerization initiator include 2,2'-azobis(isobutyronitrile) (AIBN), 2,2'-azobis(2,4-dimethylvaleronitrile), dimethyl 2,2'-azobis (2-methylpropionate), benzoyl peroxide, and lauroyl peroxide.

The temperature of heat polymerization is preferably 50 to 80° C. The reaction time is preferably 2 to 100 hours, more preferably 5 to 20 hours.

The copolymerization of hydroxystyrene or hydroxyvinylnaphthalene can be performed by using acetoxystyrene or acetoxyvinylnaphthalene instead of hydroxystyrene or hydroxyvinylnaphthalene, and de-protecting the acetoxy group by alkaline hydrolysis after the polymerization to form polyhydroxystyrene or hydroxypolyvinylnaphthalene, as an optional method.

In the alkaline hydrolysis, aqueous ammonia, triethylamine, and so on can be used as a base. The reaction temperature is preferably −20 to 100° C., more preferably 0 to 60° C.; and the reaction time is preferably 0.2 to 100 hours, more preferably 0.5 to 20 hours.

The ratio of the repeating units A1 to A7, B, C, D, and E is preferably such that $0 \leq a1 \leq 1.0$, $0 \leq a2 \leq 1.0$, $0 \leq a3 \leq 1.0$, $0 \leq a4 \leq 1.0$, $0 \leq a5 \leq 1.0$, $0 \leq a6 \leq 1.0$, $0 \leq a7 \leq 1.0$, $0 < a1+a2+a3+a4+a5+a6+a7 \leq 1.0$, $0 \leq b < 1.0$, $0 \leq c < 1.0$, $0 \leq d \leq 0.7$, and $0 \leq e \leq 0.4$; more preferably $0 \leq a1 \leq 0.9$, $0 \leq a2 \leq 0.9$, $0 \leq a3 \leq 0.9$, $0 \leq a4 \leq 0.9$, $0 \leq a5 \leq 0.9$, $0 \leq a6 \leq 0.9$, $0 \leq a7 \leq 0.9$, $0.01 \leq a1+a2+a3+a4+a5+a6+a7 \leq 0.9$, $0.05 \leq b < 0.9$, $0 \leq c \leq 0.8$, $0 \leq d \leq 0.6$, and $0 \leq e \leq 0.3$; still more preferably $0 \leq a1 \leq 0.8$, $0 \leq a2 \leq 0.8$, $0 \leq a3 \leq 0.8$, $0 \leq a4 \leq 0.8$, $0 \leq a5 \leq 0.8$, $0 \leq a6 \leq 0.8$, $0 \leq a7 \leq 0.8$, $0.02 \leq a1+a2+a3+a4+a5+a6+a7 \leq 0.8$, $0.1 \leq b \leq 0.8$, $0 \leq c \leq 0.7$, $0 \leq d \leq 0.5$, and $0 \leq e \leq 0.2$.

Incidentally, a+b+c=1, for example, means that the total amount of the repeating units A, B, and C is 100% by mole based on the total amount of the whole repeating units in a polymer compound containing repeating units A, B, and C; and a+b+c<1 means that the total amount of the repeating units A, B, and C is less than 100% by mole based on the total amount of the whole repeating units, and other repeating unit(s) is contained in addition to the repeating units A, B, and C.

The polymer compound preferably has a molecular weight of 500 or more, more preferably 1,000 or more and 1,000,000 or less, much more preferably in a range of 2,000 or more and 500,000 or less as a weight averaged molecular weight. When the ionic monomer that is not incorporated into the polymer compound (residual monomer) is smaller after the polymerization, it is possible to exclude the risk of permeation thereof into skin in a biocompatible test to cause allergies. Accordingly, it is preferable to decrease the amount of residual monomer. The amount of residual monomer is preferably 10% by mass or less on the basis of the total 100 parts by mass of the whole polymer compound.

[Organic Solvent]

The inventive bio-electrode composition may contain organic solvent. Illustrative examples of the organic solvent include aromatic hydrocarbon solvent such as toluene, xylene, cumene, 1,2,3-trimethylbenzene, 1,2,4-trimethylbenzene, 1,3,5-trimethylbenzene, styrene, α-methylstyrene, butylbenzene, sec-butylbenzene, isobutylbenzene, cymene, diethylbenzene, 2-ethyl-p-xylene, 2-propyltoluene, 3-propyltoluene, 4-propyltoluene, 1,2,3,5-tetramethylbenzene, 1,2,4,5-tetramethylbenzene, tetrahydronaphthalene, 4-phenyl-1-butene, tert-amylbenzene, amylbenzene, 2-tert-butyltoluene, 3-tert-butyltoluene, 4-tert-butyltoluene, 5-isopropyl-m-xylene, 3-methylethylbenzene, tert-butyl-3-ethylbenzene, 4-tert-butyl-o-xylene, 5-tert-butyl-m-xylene, tert-butyl-p-xylene, 1,2-diisopropylbenzene, 1,3-diisopropylbenzene, 1,4-diisopropylbenzene, dipropylbenzene, 3,9-dodecadiyne, pentamethylbenzene, hexamethylbenzene, hexylbenzene, and 1,3,5-triethylbenzene; aliphatic hydrocarbon solvent such as n-heptane, isoheptane, 3-methylhexane, 2,3-dimethylpentane, 3-ethylpentane, 1,6-heptadiene, 5-methyl-1-hexyn, norbornane, norbornene, dicyclopentadiene, 1-methyl-1,4-cyclohexadiene, 1-heptyne, 2-heptyne, cycloheptane, cycloheptene, 1,3-dimethylcyclopentane, ethylcyclopentane, methylcyclohexane, 1-methyl-1-cyclohexene, 3-methyl-1-cyclohexene, methylenecyclohexane, 4-methyl-1-cyclohexene, 2-methyl-1-hexene, 2-methyl-2-hexene, 1-heptene, 2-heptene, 3-heptene, n-octane, 2,2-dimethylhexane, 2,3-dimethylhexane, 2,4-dimethylhexane, 2,5-dimethylhexane, 3,3-dimethylhexane, 3,4-dimethylhexane, 3-ethyl-2-methylpentane, 3-ethyl-3-methylpentane, 2-methylheptane, 3-methylheptane, 4-methylheptane, 2,2,3-trimethylpentane, 2,2,4-trimethylpentane, cyclooctane, cyclooctene, 1,2-dimethylcyclohexane, 1,3-dimethylcyclohexane, 1,4-dimethylcyclohexane, ethylcyclohexane, vinylcyclohexane, isopropylcyclopentane, 2,2-dimethyl-3-hexene, 2,4-dimethyl-1-hexene, 2,5-dimethyl-1-hexene, 2,5-dimethyl-2-hexene, 3,3-dimethyl-1-hexene, 3,4-dimethyl-1- hexene, 4,4-dimethyl-1-hexene, 2-ethyl-1-hexene, 2-methyl-1-heptene, 1-octene, 2-octene, 3-octane, 4-octane, 1,7-octadiene, 1-octyne, 2-octyne, 3-octyne, 4-octyne, n-nonane, 2,3-dimethylheptane, 2,4-dimethylheptane, 2,5-dimethylheptane, 3,3-dimethylheptane, 3,4-dimethylheptane, 3,5-dimethylheptane, 4-ethylheptane, 2-methyloctane, 3-methyloctane, 4-methyloctane, 2,2,4,4-tetramethylpentane, 2,2,4-trimethylhexane, 2,2,5-trimethylhexane, 2,2-dimethyl-3-heptene, 2,3-dimethyl-3-heptene, 2,4-dimethyl-1-heptene, 2,6-dimethyl-1-heptene, 2,6-dimethyl-3-heptene, 3,5-dimethyl-3-heptene, 2,4,4-trimethyl-1-hexene, 3,5,5-trimethyl-1-hexene, 1-ethyl-2-methylcyclohexane, 1ethyl-3-methylcyclohexane, 1-ethyl-4-methylcyclohexane, propylcyclohexane, isopropylcylohexane, 1,1,3-trimethylcyclohexane, 1,1,4-trimethylcyclohexane, 1,2,3-trimethylcyclohexane, 1,2,4-trimethylcyclohexane, 1,3,5-trimethylcyclohexane, allylcyclohexane, hydrindane, 1,8-nonadiene, 1-nonyne, 2-nonyne, 3-nonyne, 4-nonyne, 1-nonene, 2-nonene, 3-nonene, 4-nonene, n-decane, 3,3-dimethyloctane, 3,5-dimethyloctane, 4,4-dimethyloctane, 3-ethyl-3-methylheptane, 2-methylnonane, 3-methylnonane, 4-methylnonane, tert-butylcyclohexane, butylcyclohexane, isobutylcyclohexane, 4-isopropyl-1-methylcyclohexane, pentylcyclopentane, 1,1,3,5-tetramethylcyclohexane, cyclododecane, 1-decene, 2-decene, 3-decene, 4-decene, 5-decene, 1,9-decadiene, decahydronaphthalene, 1-decyne, 2-decyne, 3-decyne, 4-decyne, 5-decyne, 1,5,9-decatriene, 2,6-dimethyl-2,4,6-octatriene, limonene, myrcene, 1,2,3,4,5-pentamethylcyclopentadiene, α-phellandrene, pinene, terpinene, tetrahydrodicyclopentadiene, 5,6-dihydrodicyclopentadiene, dicyclopentadiene, 1,4-decadiyne, 1,5-decadiyne, 1,9-decadiyne, 2,8-decadiyne, 4,6-decadiyne, n-undecane, amylcyclohexane, 1-undecene, 1,10-undecadiene, 1-undecyne, 3-undecyne, 5-undecyne, tricyclo[6.2.1.0$^{2,7}$]undeca-4-ene, n-dodecane, 2-methylundecane, 3-methylundecane, 4-methylundecane, 5-methylundecane, 2,2,4,6,6-pentamethylheptane, 1,3-dimethyladamantane, 1-ethyladamantane, 1,5,9-cyclododecatriene, 1,2,4-trivinylcyclohexane, isoparaffin; ketone solvent such as cyclohexanone, cyclopentanone, 2-octanone, 2-nonanone, 2-heptanone, 3-heptanone, 4-heptanone, 2-hexanone, 3-hexanone, diisobutyl ketone, methylcyclohexanone, and methyl n-pentyl ketone; alcohol solvent such as 3-methoxybutanol, 3-methyl-3-methoxybutanol, 1-methoxy-2-propanol, and 1-ethoxy-2-propanol; ether solvent such as propylene glycol monomethyl ether, ethylene glycol monomethyl ether, propylene glycol monoethyl ether, ethylene glycol monoethyl ether, propylene glycol dimethyl ether, diethylene glycol dimethyl ether, diisopropyl ether, diisobutyl ether, diisopentyl ether, di-n-pentyl ether, methyl cylopentyl ether, methyl cyclohexyl ether, di-n-butyl ether, di-sec-butyl ether, di-sec-pentyl ether, di-tert-amyl ether, di-n-hexyl ether, and anisole; ester solvent such as propylene glycol monomethyl ether acetate, propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate; lactone solvent such as γ-butyrolactone.

The amount of organic solvent is preferably in a range of 10 to 50,000 parts by mass on the basis of 100 parts by mass of the polymer compound.

[Carbon Material]

The inventive bio-electrode composition can contain a carbon material as an electric conductivity improver to further enhance the electric conductivity. Illustrative examples of the carbon material include carbon black and carbon nanotube. The carbon nanotube may be either single layer or multilayer, and the surface may be modified with an organic group(s). The amount of carbon material is preferably in a range of 1 to 50 parts by mass on the basis of 100 parts by mass of the polymer compound.

[Electric Conductivity Improver Other than Carbon Material]

The inventive bio-electrode composition can also contain an electric conductivity improver other than the carbon material. Illustrative examples thereof include powder of noble metal such as gold, silver, and platinum, as well as copper and nickel; particles of resin coated with noble metal such as gold, silver, and platinum, as well as copper and nickel; nanoparticles of gold, silver, and platinum; as well as particles of metal oxide such as indium-tin oxide (ITO), indium-zinc oxide (IZO), tin oxide, and zinc oxide. In particular, silver powder; ITO particles; powder of a metal selected from silver, gold, platinum, copper, and nickel; or particles coated with a metal like these.

[Crosslinking Agent]

To prevent the living body contact layer of the bio-electrode from sticking to skin after delaminating the bio-electrode from the skin, a crosslinking agent can be added to the inventive bio-electrode composition. The crosslinking agent usable for the present invention is not particularly limited, but illustrative examples thereof include a melamine compound, a guanamine compound, a glycoluril compound, and a urea compound substituted with at least one group selected from a methylol group, an alkoxymethyl group, and an acyloxymethyl group; an epoxy compound; an isocyanate compound, an azide compound, and a compound containing a double bond(s) such as an alkenylether group. They can be used as additives, but may be introduced into the side chain of a polymer compound as a pendant group. It is also possible to use a compound containing a hydroxy group as the crosslinking agent.

Illustrative examples of the crosslinkinq agent based on an epoxy compound include tris(2,3-epoxypropyl)isocyanurate, trimethylolmethane triglycidyl ether, trimethylolpropane triglycidyl ether, triethylolethane triglycidyl ether, and silicone having an epoxy group. Illustrative examples of the melamine compound include hexamethylolmelamine, hexamethoxymethyl melamine, compounds in which 1 to 6 methylol groups of hexamethylolmelamine are converted into methoxymethyl groups or a mixture thereof, hexamethoxyethyl melamine, hexaacyloxymethyl melamine, and compounds in which 1 to6 methylol groups of hexamethylolmelamine are converted into acyloxymethyl groups or a mixture thereof. Illustrative examples of the guanamine compound include tetramethylol guanamine, tetramethoxymethyl guanamine, compounds in which 1 to 4 methylol groups of tetramethylol guanamine are converted into methoxymethyl groups or a mixture thereof, tetramethoxyethyl guanamine, tetraacyloxy guanamine, and compounds in which 1 to 4 methylol groups of tetramethylol guanamine are converted into acyloxymethyl groups or a mixture thereof. Illustrative examples of the glycoluril compound include tetramethylol glycoluril, tetramethoxy glycoluril, tetramethoxymethyl glycoluril, compounds in which 1 to 4 methylol groups of tetramethylol glycoluril are converted into methoxymethyl groups or a mixture thereof, and compounds in which 1 to 4 methylol groups of tetramethylol glycoluril are converted into acyloxymethyl groups or a mixture thereof. Illustrative examples of the urea compound include tetramethylolurea, tetramethoxymethylurea, compounds in which 1 to 4 methylol groups of tetramethylolurea are converted into methoxymethyl groups, or a mixture thereof, and tetramethoxyethylurea.

Illustrative examples of the isocyanate compound include trilene disocyanate, diphenylmethane diisocyanate, hexamethylene diisocyanate, and cyclohexane diisocyanate. Illustrative examples of the azide compound include 1,1'-biphenyl-4,4'-bisazide, 4,4'-methylidenebisazide, and 4,4'-oxybisazide.

Illustrative examples of the compound containing an alkenyl ether group include ethyleneglycol divinyl ether, triethyleneglycol divinyl ether, 1,2-propanediol divinyl ether, 1,4-butanediol divinyl ether, tetramethyleneglycol divinyl ether, neopentyl glycol divinyl ether, trimethylolpropane trivinyl ether, hexanediol divinyl ether, 1,4-cyclohexanediol divinyl ether, pentaerythritol trivinyl ether, pentaerythritol tetravinyl ether, sorbitol tetravinyl ether, and sorbitol pentavinyl ether.

As described above, the inventive bio-electrode composition can form a living body contact layer for a bio-electrode that can efficiently convert changes of ion concentration from skin into electric signals and conduct the signals to a device (i.e., having excellent electric conductivity), is free from the risk of causing allergies even when it is worn on skin for a long time (i.e., having excellent biocompatibility) since the ionic component of polymer is prevented from permeating skin, is prevented from lowering the electric conductivity due to perspiration or washing since the ionic component is prevented from extraction even when it is wetted with water, is light in weight, can be manufactured at low cost, and can also function as a tackiness agent. The electric conductivity can be more improved by adding a carbon material or particles coated with noble metal, and a bio-electrode with high adhesion and high elasticity can be manufactured. It is also possible to control the tackiness and elasticity by adjusting the composition of the polymer compound or the thickness of the living body contact layer appropriately.

<Bio-Electrode>

The present invention also provides a bio-electrode comprising an electro-conductive base material and a living body contact layer formed on the electro-conductive base material; wherein the living body contact layer is a cured material of the inventive bio-electrode composition described above.

Hereinafter, the inventive bio-electrode will be specifically described by reference to the FIGS., but the present invention is not limited thereto.

FIG. 1 is a schematic sectional view showing an example of the inventive bio-electrode. The bio-electrode 1 of FIG. 1 has the electro-conductive base material 2 and the living body contact layer 3 formed on the electro-conductive base material 2. The living body contact layer 3 is a layer containing the electric conductivity improver 4 dispersed in the polymer compound (resin) 5.

Figure 2:
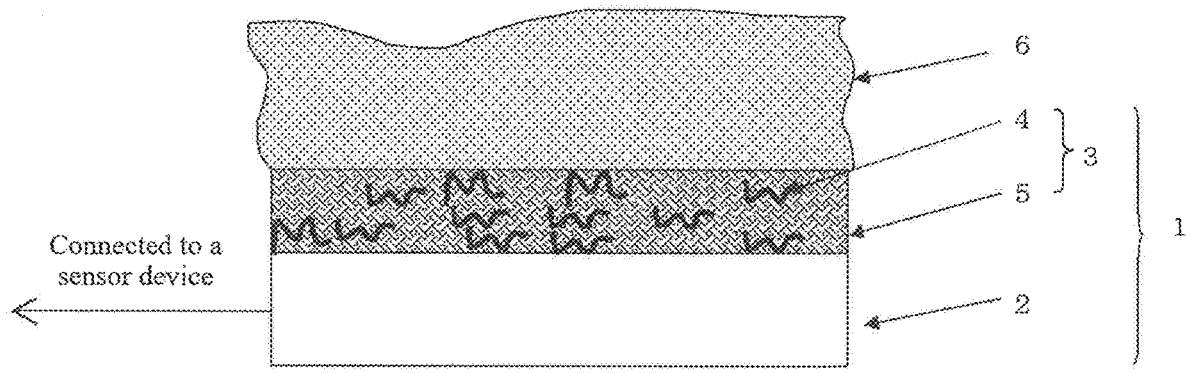
FIG. 2 is a schematic sectional view showing an example of the inventive bio-electrode worn on a living body.

When using the bio-electrode 1 of FIG. 1 like this, electric signals are picked from the living body 6 through the polymer compound 5 and the electric conductivity improver 4 while bringing the living body contact layer 3 (i.e., the layer containing the electric conductivity improver 4 dispersed in the polymer compound 5) into contact with the living body 6, and then conducted to a sensor device (not shown) through the electro-conductive base material 2 as shown in FIG. 2. As described above, the inventive bio-electrode can cope with both electric conductivity and biocompatibility by using the polymer compound described above, can improve the electric conductivity further by adding electric conductivity improver such as a carbon material in accordance with needs, and can obtain electric signals from skin stably in high sensitivity because the contact area with skin is kept constant due to the tackiness thereof.

Hereinafter, each constituent composing the inventive bio-electrode will be more specifically described.

[Electro-Conductive Base Material]

The inventive bio-electrode comprises an electro-conductive base material. This electro-conductive base material is usually connected electrically with a sensor device and so on, and conduct electrical signals picked from a living body through the living body contact layer to the sensor device and so on.

As the electro-conductive base material, any electro-conductive material can be used without being limited to particular ones. However, it is preferable to comprise one or more species selected from gold, silver, silver chloride, platinum, aluminum, magnesium, tin, tungsten, iron, copper, nickel, stainless, chromium, titanium, and carbon, for example.

The electro-conductive base material may be a hard electro-conductive substrate, an electro-conductive film having flexibility, a cloth with the surface being coated with electro-conductive paste, and a cloth into which electro-conductive polymer is kneaded without being limited to particular substrates. The electro-conductive substrate may be flat, uneven, or mesh-form of woven metal wires, which can be appropriately selected in accordance with the use of the bio-electrode.

[Living Body Contact Layer]

The inventive bio-electrode comprises a living body contact layer formed on the electro-conductive base material. This living body contact layer, which is a part to be actually in contact with a living body when using the bio-electrode, has electric conductivity and tackiness. The living body contact layer is a cured material of the inventive bio-electrode composition described above, that is to say, a tacky resin layer that contains the foregoing polymer compound having a tack function, together with additives such as a carbon material in accordance with needs.

The living body contact layer preferably has adhesion in a range of 0.1 N/25 mm or more and 20 N/25 mm or less. The adhesion is commonly measured by the method shown in JTS Z 0237, in which a metal substrate such as a stainless steel (SUS) substrate or a polyethylene terephthalate (PET) substrate can be used as a base material or, alternatively, human skin can be used for measuring. Human skin has lower surface energy compared to metals and various plastics, which energy is as low as that of Teflon (registered trade mark), and is hard to adhere.

The living body contact layer of the bio-electrode preferably has a thickness of 0.1 µm or more and 5 mm or less, more preferably 0.2 µm or more and 3 mm or less. A thinner living body contact layer has lower adhesion, but has improved flexibility and lighter weight to improve compatibility with skin. The thickness of the living body contact layer can be selected based on the balance of adhesion and texture.

The inventive bio-electrode may be provided with a tacky film separately on the living body contact layer as previous bio-electrodes (e.g., the bio-electrode described in Japanese Unexamined Patent Application Publication No. 2004-033468) in order to prevent peeling off of the bio-electrode from a living body during the use. When the tacky film is prepared separately, the tacky film may be formed by using a raw material for the tacky film such as an acrylic type, an urethane type, and a silicone type. Particularly, the silicone type is suitable because of the high transparency of oxygen, which enables breathing through the skin while pasting the same, the high water repellency, which decreases lowering of tackiness due to perspiration, and the low stimuli to skin. It is to be noted that the inventive bio-electrode does not necessarily require the tacky film that is prepared separately described above, because peeling off from a living body can be prevented by adding tackifier to the bio-electrode composition or using a polymer compound having good tackiness to a living body as described above.

When the inventive bio-electrode is used as a wearable device, the components such as wiring between the bio-electrode and a sensor device may be any material without being limited to particular ones. For example, it is possible to apply the ones described in Japanese Unexamined Patent publication (Kokai) No. 2004-033468.

As described above, the inventive bio-electrode can efficiently conduct electric signals from skin to a device (i.e., having excellent electric conductivity), is free from the risk of causing allergies even when it is worn on skin for a long time (i.e., having excellent biocompatibility), is light in weight, can be manufactured at low cost, and does not cause large lowering of the electric conductivity even when it is wetted with water or dried, because the living body contact layer is formed from a cured material of the inventive bio-electrode composition described above. The electric conductivity can be more improved by adding a carbon material, and a bio-electrode with particularly high adhesion and high elasticity can be manufactured by combining a polymer compound with tackiness and elasticity. The elasticity and tackiness to skin can be improved by additives, and can be adjusted by adjusting the composition of the polymer compound and the thickness of the living body contact layer appropriately. Accordingly, the inventive bio-electrode described above is particularly suitable as a bio-electrode used for a medical wearable device.

<Method for Manufacturing Bio-Electrode>

The present invention also provides a method for manufacturing a bio-electrode having an electro-conductive base material and a living body contact layer formed on the electro-conductive base material, comprising: applying the inventive bio-electrode composition described above onto the electro-conductive base material; and curing the bio-electrode composition; thereby forming the living body contact layer.

Incidentally, the electro-conductive base material, the bio-electrode composition, and so on used for the inventive production method of a bio-electrode may be the same as those described in the explanation of the inventive bio-electrode.

As the method for applying the bio-electrode composition onto the electro-conductive base material, any method can be used without being limited to particular ones; and, for example, dip coating, spray coating, spin coating, roll coating, flow coating, doctor coating, screen printing, flexographic printing, gravure printing, and inkjet printing are suitable.

The method for curing the polymer compound can be appropriately selected based on a kind of polymer compound used for the bio-electrode composition without being limited to particular methods. For example, the polymer compound is preferably cured by either or both of heat and light. The foregoing bio-electrode composition can also be cured by adding a catalyst to generate acid or base, which causes a crosslinking reaction.

In case of heating, the temperature may be appropriately selected based on a kind of polymer compound used for the bio-electrode composition without being limited to particular temperature. For example, it is preferable to be about 50 to 250° C.

When the heating and light irradiation are combined, it is possible to perform the heating and the light irradiation simultaneously, to perform the heating after the light irradiation, or to perform the light irradiation after the heating. It is also possible to perform air-drying to evaporate solvent before heating the coating film.

As described above, the inventive method for manufacturing a bio-electrode can manufacture the inventive bio-electrode easily and at low cost, which has excellent electric conductivity and biocompatibility as well as light weight without causing large lowering of the electric conductivity even when it is wetted with water or dried.

EXAMPLES

Hereinafter, the present invention will be specifically described by reference to Examples and Comparative Examples, but the present invention is not limited thereto.

The following are Ionic polymers 1 to 15, Comparative polymer 1, and Comparative ionic polymers 1 and 2, each blended as a polymer compound to a bio-electrode composition solution.

Each 30 mass % monomer solution in propylene glycol-1-monomethyl ether-2-acetate (PGMEA) was mixed in a reaction vessel. The reaction vessel was cooled to −70° C. under a nitrogen atmosphere, and degassing under reduced pressure and nitrogen blowing were repeated three times. After elevating the temperature to room temperature, azobis (isobutyronitrile) (AIBN) was added as a polymerization initiator in an amount of 0.01 mole per 1 mole of the total monomer. After elevating the temperature to 60° C., this was reacted for 15 hours to give a solution containing a polymer (each of Ionic polymer solutions 1 to 15, Comparative polymer solution 1, and Comparative ionic polymer solutions 1 and 2). The composition of the obtained polymer was confirmed by $^1$H-NMR after drying the solvent. The molecular weight (Mw) and the dispersity (Mw/Mn) of the obtained polymer was confirmed by GPC using THF as a solvent.

Ionic Polymer 1:

Mw=20,900

Mw/Mn=2.21

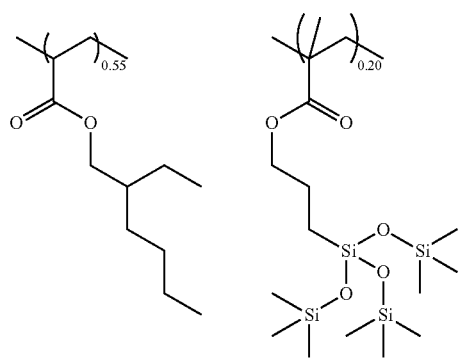

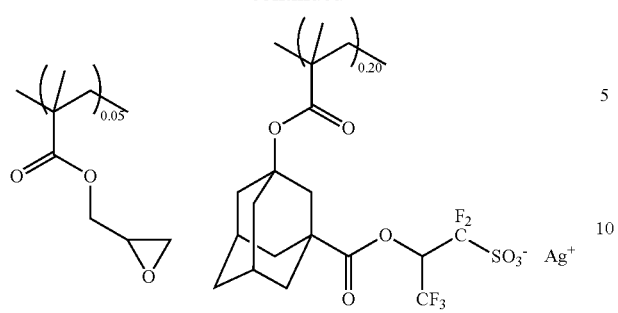
Ionic Polymer 2:
Mw=27,400
Mw/Mn=1.94
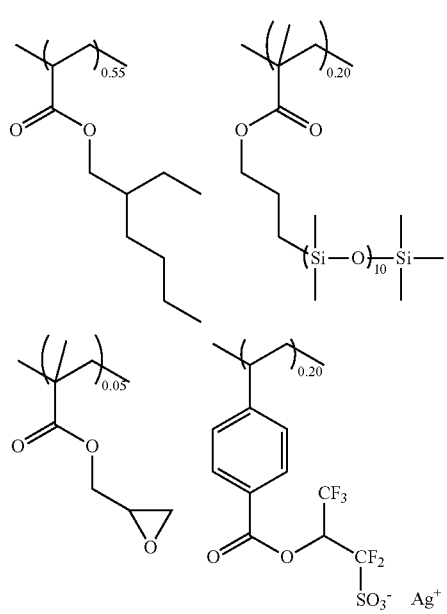
(the repeating number in the formula represents the average value)
Ionic Polymer 3:
Mw=30,600
Mw/Mn=1.88
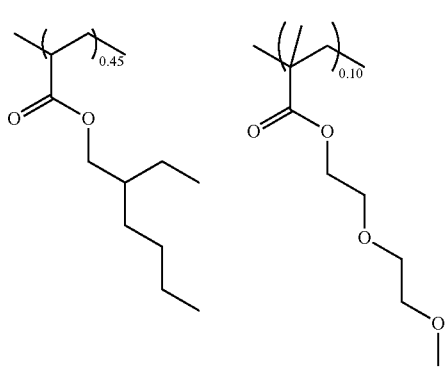
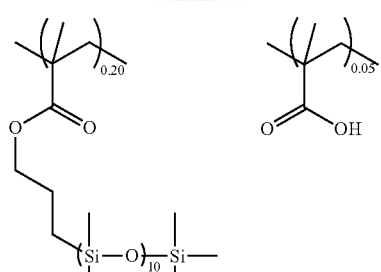
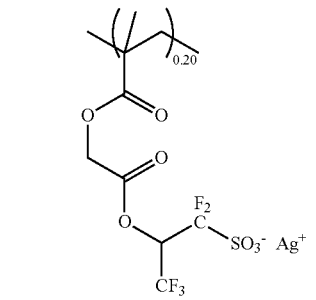
(the repeating number in the formula represents the average value)
Ionic Polymer 4:
Mw=26,600
Mw/Mn=1.86
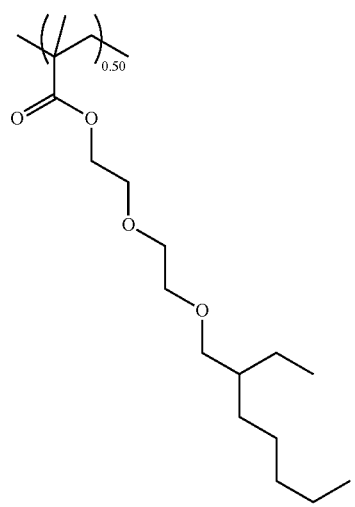
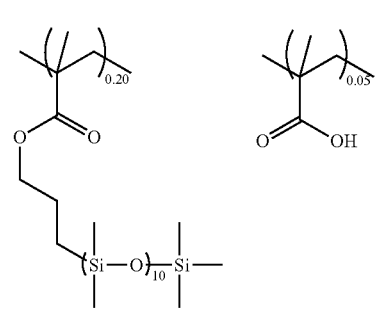

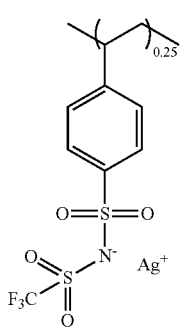
(the repeating number in the formula represents the average value)
Ionic Polymer 5:
  Mw=80,900
  Mw/Mn=4.33
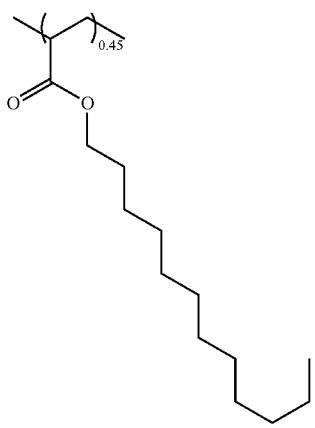
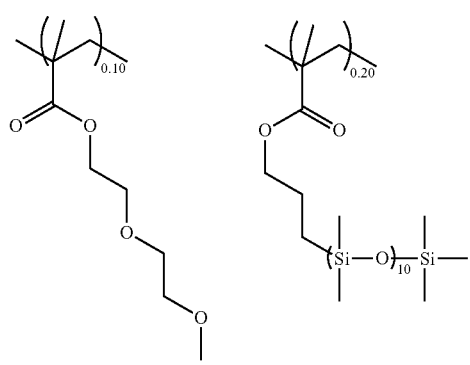
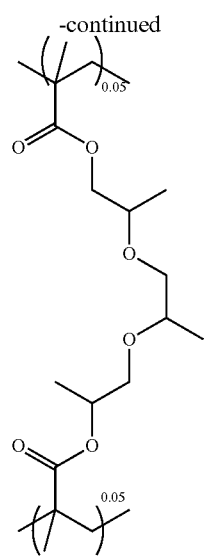
(the repeating number in the formula represents the average value)
Ionic Polymer 6:
  Mw=35,600
  Mw/Mn=2.34
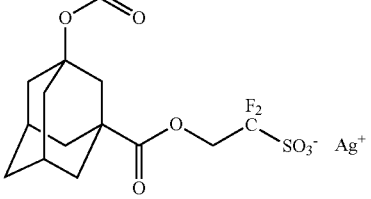
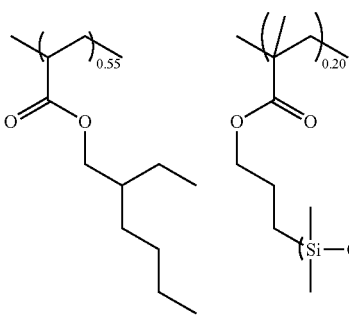
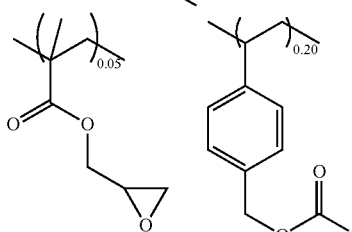
(the repeating number in the formula represents the average value)

Ionic Polymer 7:
 Mw=35,700
 Mw/Mn=2.33
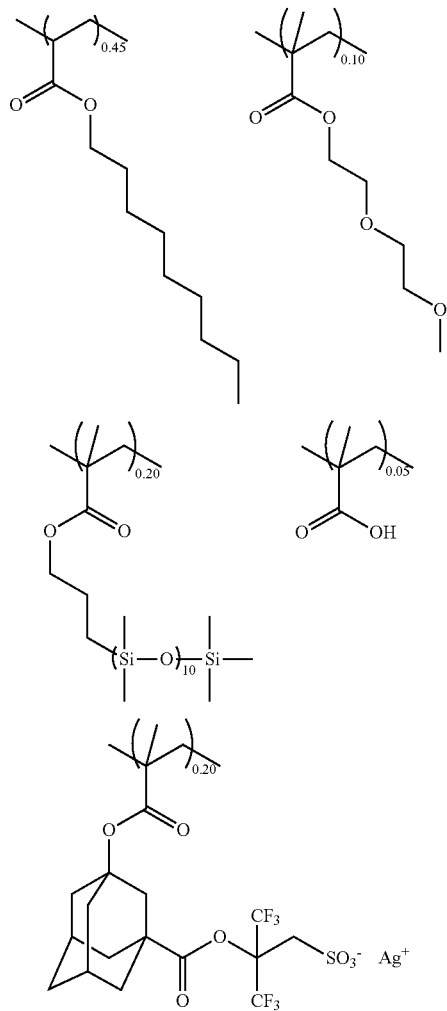
(the repeating number in the formula represents the average value)
Ionic Polymer 8:
 Mw=30,900
 Mw/Mn=2.66
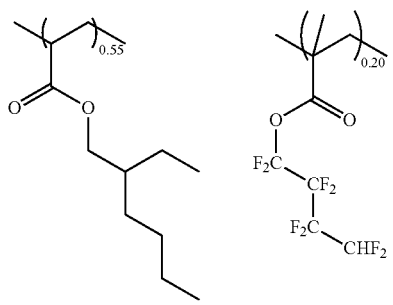
-continued
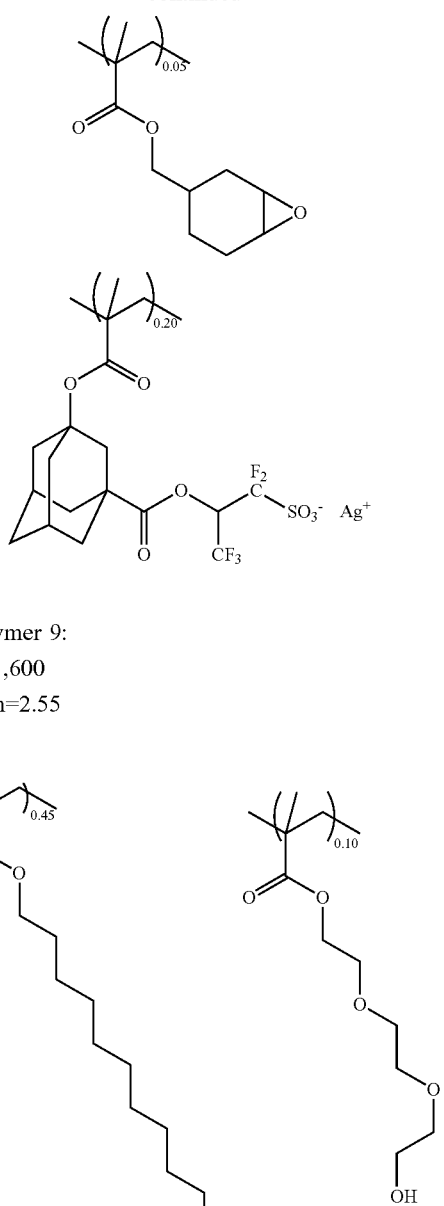
Ionic Polymer 9:
 Mw=51,600
 Mw/Mn=2.55
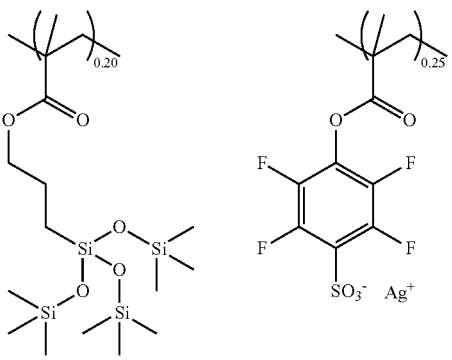

151
Ionic Polymer 10:
Mw=75,600
Mw/Mn=5.38
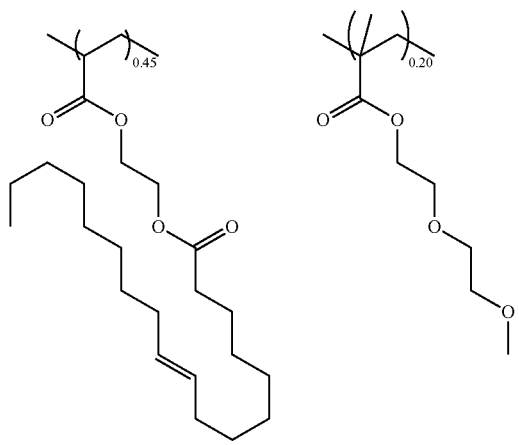
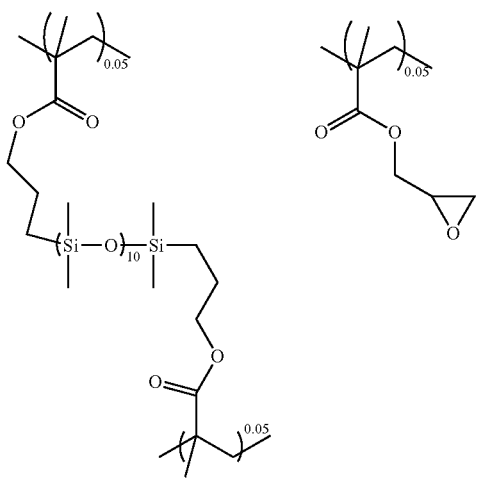
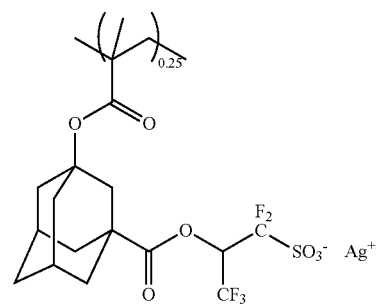
(the repeating number in the formula represents the average value)
152
Ionic Polymer 11:
Mw=65,600
Mw/Mn=5.36
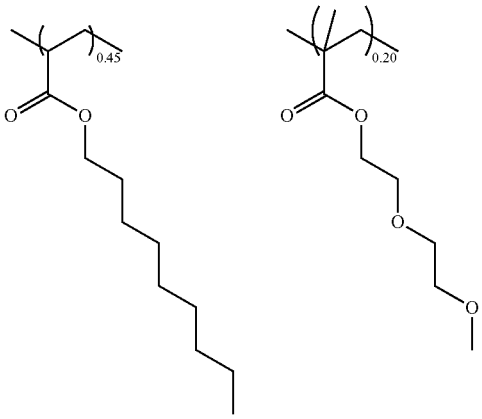
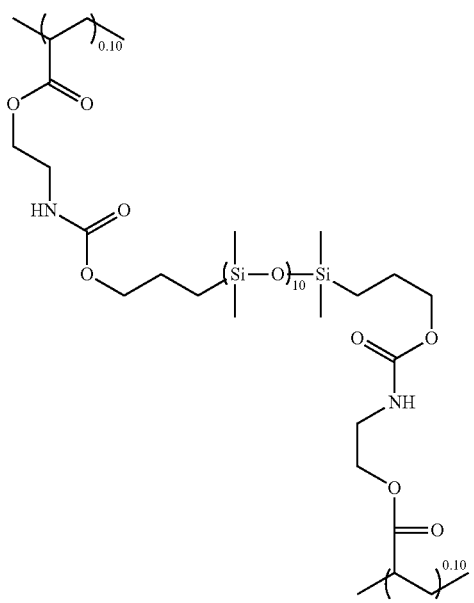
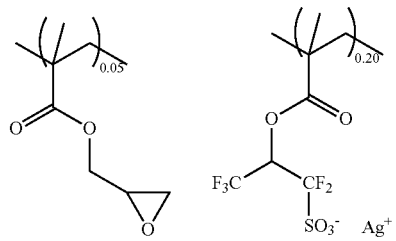
(the repeating number in the formula represents the average value)

Ionic Polymer 12:
 Mw=16,300
 Mw/Mn=1.75
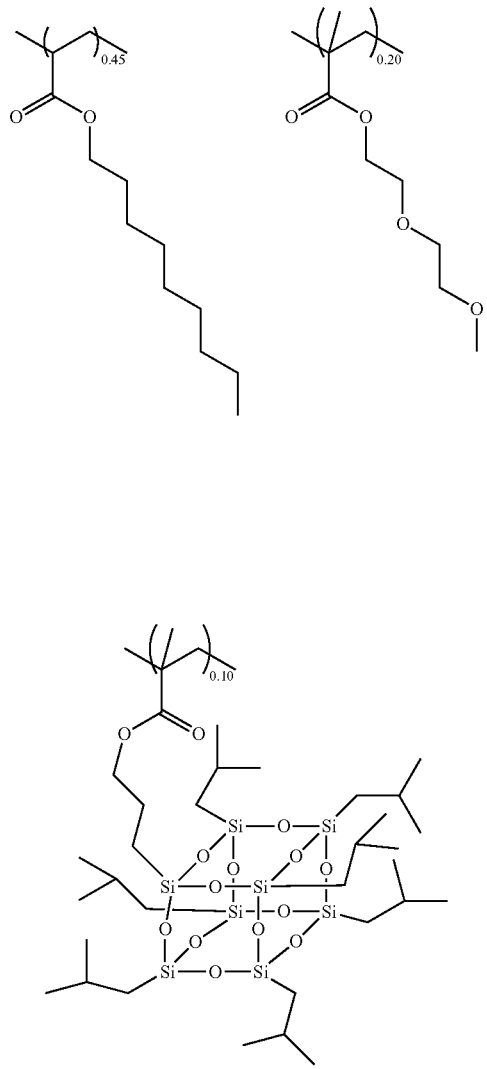
Ionic Polymer 13:
 Mw=29,600
 Mw/Mn=1.89
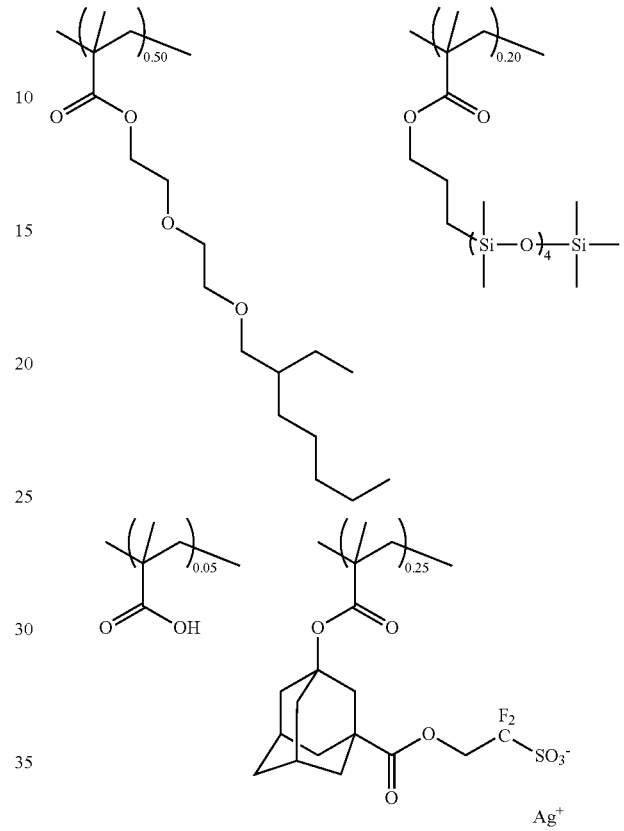
(the repeating number in the formula represents the average value)
Ionic Polymer 14:
 Mw=29,800
 Mw/Mn=2.10
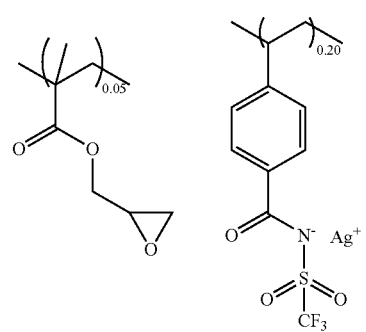
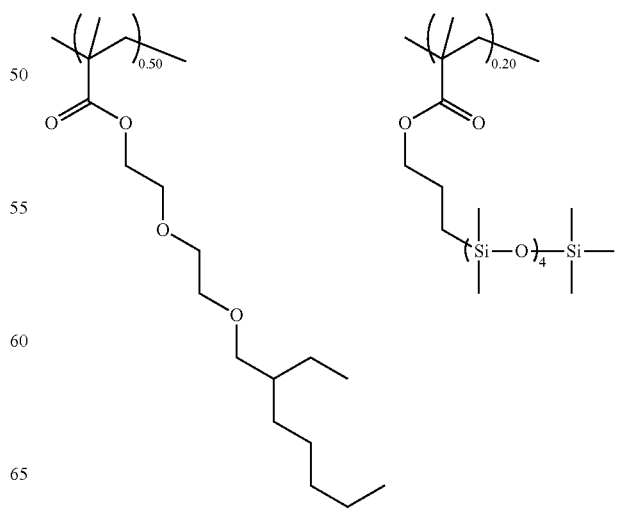

-continued

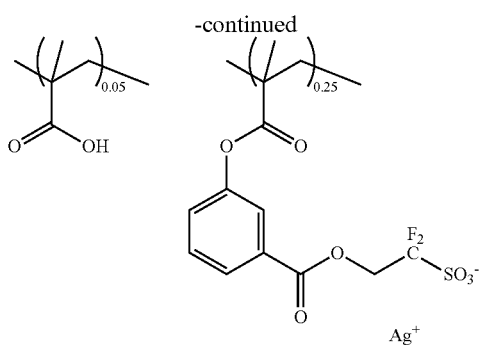

(the repeating number in the formula represents the average value)

Ionic Polymer 15:
  Mw=43,100
  Mw/Mn=2.01

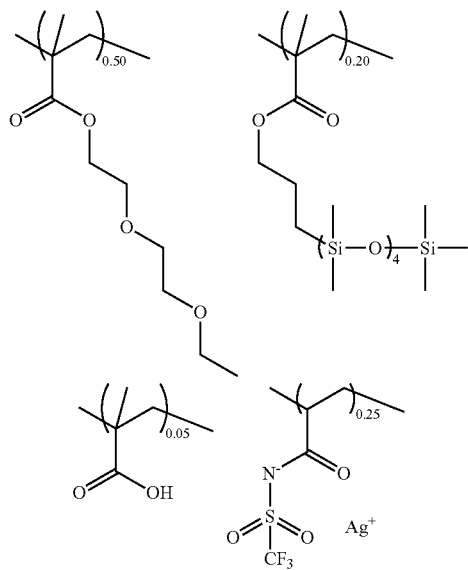

(the repeating number in the formula represents the average value)

Comparative Polymer 1:
  Mw=116,000
  Mw/Mn=2.20

Comparative Polymer 1

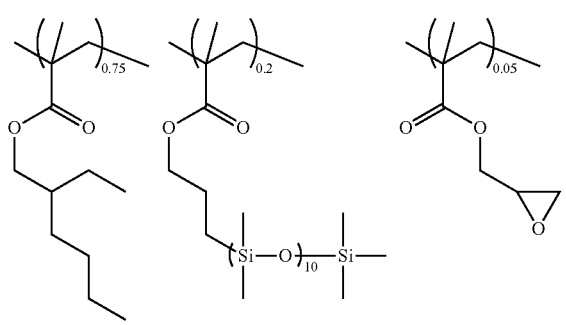

(the repeating number in the formula represents the average value)

Comparative Ionic Polymer 1:
  Mw=44,900
  Mw/Mn=2.59

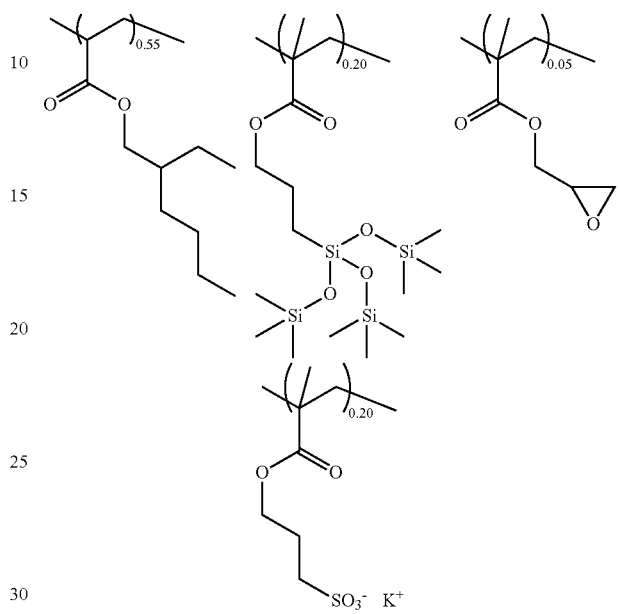

Comparative Ionic Polymer 2:
  Mw=57,900
  Mw/Mn=1.89

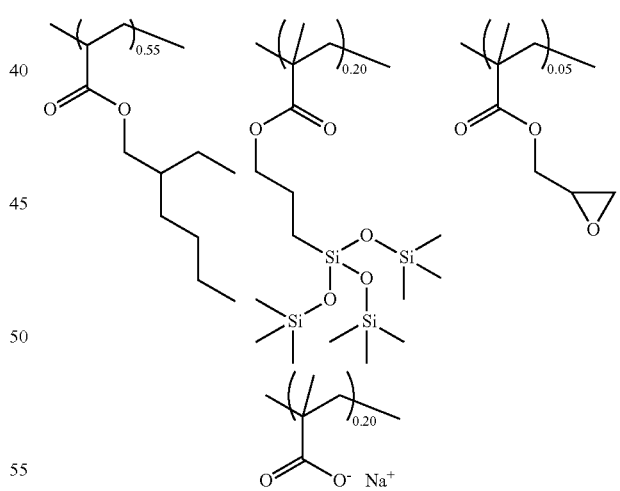

The following are structures of Comparative salts 1 to 4 each blended to the bio-electrode composition solution.

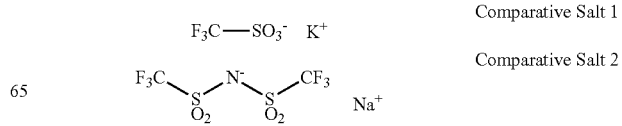

Comparative Salt 1

Comparative Salt 2

-continued

Comparative Salt 3
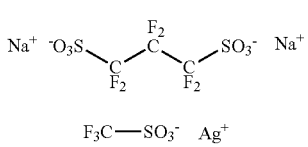

Comparative Salt 4

F₃C—SO₃⁻ Ag⁺

The following is a structure of Crosslinking agent 1 blended to the bio-electrode composition solution as an additive.

Crosslinking agent 1
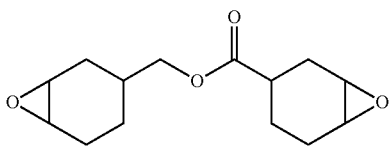

The following are electric conductivity improvers (carbon black, carbon nanotube, Au-coated particle, Ag-coated particle and ITO particle) blended to the bio-electrode composition solution as an additive.

Carbon black: DENKA BLACK HS-100 manufactured by Denka Co., Ltd.

Carbon nanotube: Multi-walled having a diameter of 60 to 100 nm and a length of 5 μm manufactured by Sigma-Aldrich Co. LLC.

Au-coated particle: Micropearl AU (the diameter of 100 μm) manufactured by SEKISUI CHEMICAL CO. LTD.

Ag-coated particle: Ag-coated powder (the diameter of 30 μm) manufactured by Mitsubishi Materials Electronic Chemicals Co., Ltd.

ITO particle: ITO powder (the diameter of 0.03 μm) manufactured by Mitsubishi Materials Electronic Chemicals Co., Ltd.

Examples 1 to 20, Comparative Examples 1 to 6

Each Polymer compound solution, Comparative salt, and additives (electric conductivity improver, crosslinking agent) were blended on the basis of the composition described in Tables 1 to prepare a bio-electrode composition solution (each of Bio-electrode composition solutions 1 to 20, Comparative bio-electrode composition solutions 1 to 6).

TABLE 1

| Bio-electrode composition solution | Polymer compound solutions (parts by mass) | Comparative salts (parts by mass) | Additives (parts by mass) |
|---|---|---|---|
| Bio-electrode composition solution 1 | Ionic polymer solution 1 (10) | — | Carbon black (0.3) |
| Bio-electrode composition solution 2 | Ionic polymer solution 2 (10) | — | Carbon black (0.3) |
| Bio-electrode composition solution 3 | Ionic polymer solution 3 (10) | — | Carbon black (0.3), Crosslinking agent 1 (0.05) |
| Bio-electrode composition solution 4 | Ionic polymer solution 4 (10) | — | Carbon black (0.3), Crosslinking agent 1 (0.05) |
| Bio-electrode composition solution 5 | Ionic polymer solution 5 (10) | — | Carbon black (0.3) |
| Bio-electrode composition solution 6 | Ionic polymer solution 6 (10) | — | Carbon black (0.3) |
| Bio-electrode composition solution 7 | Ionic polymer solution 7 (10) | — | Carbon black (0.3), Crosslinking agent 1 (0.05) |
| Bio-electrode composition solution 8 | Ionic polymer solution 8 (10) | — | Carbon black (0.3) |
| Bio-electrode composition solution 9 | Ionic polymer solution 9 (10) | — | Carbon black (0.3), Crosslinking agent 1 (0.05) |
| Bio-electrode composition solution 10 | Ionic polymer solution 10 (10) | — | Carbon black (0.3) |
| Bio-electrode composition solution 11 | Ionic polymer solution 11 (10) | — | Carbon black (0.3) |
| Bio-electrode composition solution 12 | Ionic polymer solution 12 (10) | — | Carbon black (0.3) |
| Bio-electrode composition solution 13 | Ionic polymer solution 13 (10) | — | Carbon black (0.3), Crosslinking agent 1 (0.05) |
| Bio-electrode composition solution 14 | Ionic polymer solution 14 (10) | — | Carbon black (0.3), Crosslinking agent 1 (0.05) |
| Bio-electrode composition solution 15 | Ionic polymer solution 15 (10) | — | Carbon black (0.3), Crosslinking agent 1 (0.05) |
| Bio-electrode composition solution 16 | Ionic polymer solution 1 (5) Ionic polymer solution 3 (5) | — | Carbon black (0.3) |
| Bio-electrode composition solution 17 | Ionic polymer solution 10 (10) | — | Carbon nanotube (0.1) |
| Bio-electrode composition solution 18 | Ionic polymer solution 10 (10) | — | Au-coat particle (0.3) |
| Bio-electrode composition solution 19 | Ionic polymer solution 10 (10) | — | Ag-coat particle (0.3) |
| Bio-electrode composition solution 20 | Ionic polymer solution 10 (10) | — | ITO particle (0.3) |
| Comparative bio-electrode composition solution 1 | Comparative polymer solution 1 (10) | Comparative salt 1 (0.3) | Carbon black (0.3) |

TABLE 1-continued

| Bio-electrode composition solution | Polymer compound solutions (parts by mass) | Comparative salts (parts by mass) | Additives (parts by mass) |
|---|---|---|---|
| Comparative bio-electrode composition solution 2 | Comparative polymer solution 1 (10) | Comparative salt 2 (0.3) | Carbon black (0.3) |
| Comparative bio-electrode composition solution 3 | Comparative polymer solution 1 (10) | Comparative salt 3 (0.3) | Carbon black (0.3) |
| Comparative bio-electrode composition solution 4 | Comparative polymer solution 1 (10) | Comparative salt 4 (0.3) | Carbon black (0.3) |
| Comparative bio-electrode composition solution 5 | Comparative ionic polymer solution 1 (10) | — | Carbon black (0.3) |
| Comparative bio-electrode composition solution 6 | Comparative ionic polymer solution 2 (10) | — | Carbon black (0.3) |

(Evaluation of Electric Conductivity)

Figure 3A:
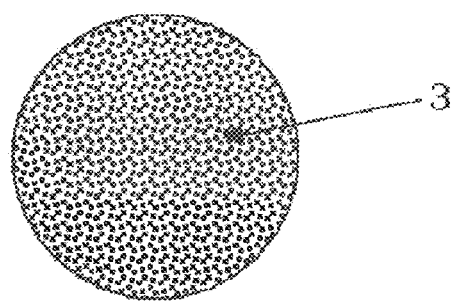
FIG. 3(a) is a schematic view of the bio-electrode produced in Examples of the present invention viewed from the living body contact layer side.
Figure 3B:
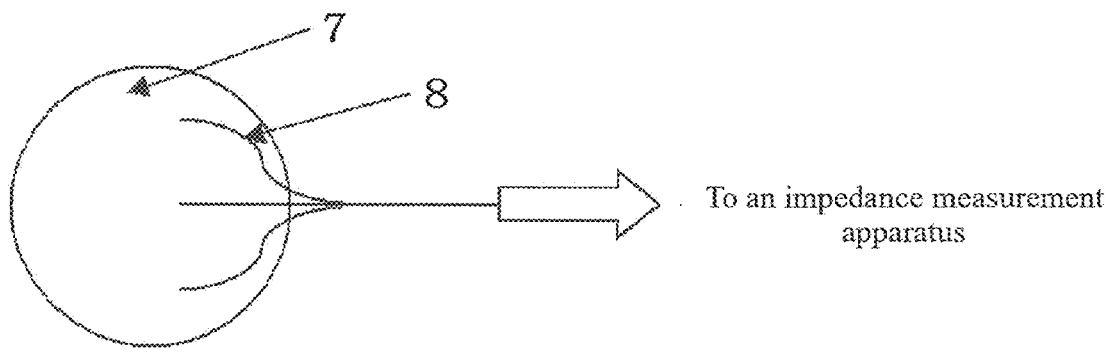
FIG. 3(b) is a schematic view of the bio-electrode produced in Examples of the present invention viewed from the electro-conductive base material side.
Figure 4:
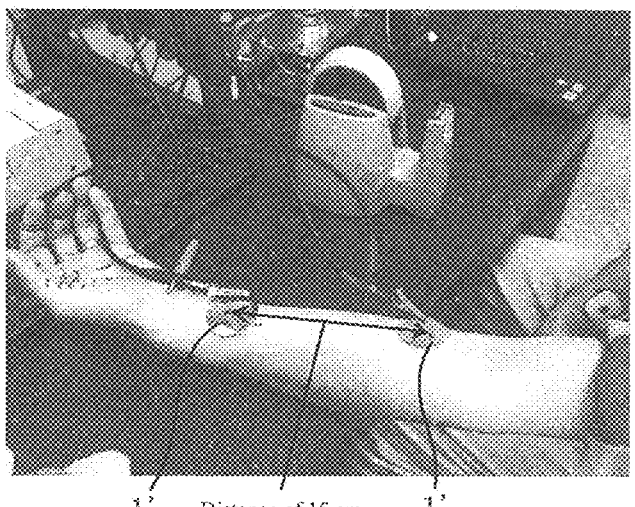
FIG. 4 is a photograph of a scene of measuring impedance on the surface of skin by using the bio-electrode produced in Examples of the present invention.

Each bio-electrode composition solution was applied onto an aluminum disk with a diameter of 3 cm and a thickness or 0.2 mm by using an applicator. This was air dried at room temperature for 6 hours, followed by curing through baking at 130° C. for 30 minutes under a nitrogen atmosphere by using an oven to produce four pieces of bio-electrodes for each bio-electrode composition solution. Thus obtained bio-electrode was provided with the living body contact layer 3 at one side and provided with the aluminum disk 7 at the other side as an electro-conductive base material as shown in FIGS. 3(*a*) and (*b*). Then, the copper wiring 8 was pasted on the surface of the aluminum disk 7 with adhesive tape at the side that had not been coated with the living body contact layer to form a lead-out electrode, which was connected to an impedance measurement apparatus as shown in FIG. 3(*b*). Two pieces of the bio-electrodes 1' were pasted on a human arm at a distance of 15 cm from each other such that the side of each living body contact layer was in contact with the skin as shown in FIG. 4. The initial impedance was measured while altering the frequency by using an AC impedance measurement apparatus SI1260 manufactured by Solartron. Then, the remained two pieces of the bio-electrodes were immersed in pure water for 1 hour, followed by drying the water, and used for measuring the impedance on skin by the same method described above. Each impedance at the frequency of 1,000 Hz are shown in Table 2.

(Evaluation of Tackiness)

Each bio-electrode composition solution was applied onto a polyethylene naphthalate (PEN) substrate with a thickness of 100 μm by using an applicator. This was air dried at room temperature for 6 hours, followed by curing through baking at 130° C. for 30 minutes under a nitrogen atmosphere by using an oven to produce an adhesive film. From this adhesive film, a tape with a width of 25 mm was cut out. This was pressed to a stainless (SUS304) board and allowed to stand at room temperature for 20 hours. Then, the tape having adhesive mass (tackiness agent) attached thereon was pulled away from the stainless board to an angle of 180° at a speed of 300 mm/min by using tensile tester to measure the force (N/25 mm) for peeling the tape. The results are shown in Table 2.

(Measurement of Thickness of Living Body Contact Layer)

On each bio-electrode produced in the evaluation test of electric conductivity described above, the thickness of the living body contact layer was measured by using a micrometer. The results are shown in Table 2.

TABLE 2

| Examples | Bio-electrode composition solutions | Thickness of resin (μm) | Initial impedance (Ω) | Impedance after water immersion (Ω) |
|---|---|---|---|---|
| Example 1 | Bio-electrode composition solution 1 | 230 | $2.1E^4$ | $2.3E^4$ |
| Example 2 | Bio-electrode composition solution 2 | 250 | $1.1E^4$ | $1.3E^4$ |
| Example 3 | Bio-electrode composition solution 3 | 190 | $1.7E^4$ | $1.8E^4$ |
| Example 4 | Bio-electrode composition solution 4 | 210 | $8.1E^3$ | $8.3E^3$ |
| Example 5 | Bio-electrode composition solution 5 | 290 | $2.5E^4$ | $2.3E^4$ |
| Example 6 | Bio-electrode composition solution 6 | 190 | $2.7E^4$ | $3.3E^4$ |
| Example 7 | Bio-electrode composition solution 7 | 200 | $5.1E^4$ | $5.3E^4$ |
| Example 8 | Bio-electrode composition solution 8 | 220 | $4.1E^4$ | $4.3E^4$ |
| Example 9 | Bio-electrode composition solution 9 | 230 | $3.4E^4$ | $3.3E^4$ |
| Example 10 | Bio-electrode composition solution 10 | 290 | $3.1E^4$ | $4.1E^4$ |
| Example 11 | Bio-electrode composition solution 11 | 310 | $1.9E^4$ | $1.3E^4$ |
| Example 12 | Bio-electrode composition solution 12 | 220 | $5.1E^4$ | $5.3E^4$ |
| Example 13 | Bio-electrode composition solution 13 | 220 | $4.1E^4$ | $5.3E^4$ |
| Example 14 | Bio-electrode composition solution 14 | 250 | $5.1E^4$ | $5.3E^4$ |
| Example 15 | Bio-electrode composition solution 15 | 220 | $1.1E^4$ | $1.3E^4$ |
| Example 16 | Bio-electrode composition solution 16 | 260 | $4.1E^4$ | $4.3E^4$ |
| Example 17 | Bio-electrode composition solution 17 | 270 | $7.1E^4$ | $7.3E^4$ |
| Example 18 | Bio-electrode composition solution 18 | 240 | $9.1E^4$ | $9.3E^4$ |
| Example 19 | Bio-electrode composition solution 19 | 240 | $8.1E^4$ | $8.3E^4$ |
| Example 20 | Bio-electrode composition solution 20 | 250 | $8.8E^4$ | $9.3E^4$ |
| Comparative Example 1 | Comparative bio-electrode composition solution 1 | 220 | $8.6E^4$ | $1.3E^6$ |

TABLE 2-continued

| Examples | Bio-electrode composition solutions | Thickness of resin (μm) | Initial impedance (Ω) | Impedance after water immersion (Ω) |
|---|---|---|---|---|
| Comparative Example 2 | Comparative bio-electrode composition solution 2 | 230 | $7.6E^4$ | $2.3E^6$ |
| Comparative Example 3 | Comparative bio-electrode composition solution 3 | 220 | $6.6E^4$ | $4.3E^6$ |
| Comparative Example 4 | Comparative bio-electrode composition solution 4 | 250 | $4.6E^4$ | $5.7E^5$ |
| Comparative Example 5 | Comparative bio-electrode composition solution 5 | 280 | $3.6E^6$ | $1.3E^7$ |
| Comparative Example 6 | Comparative bio-electrode composition solution 6 | 280 | $4.1E^7$ | $8.3E^7$ |

As shown in Table 2, in each of Examples 1 to 20, the living body contact layer of which was formed by using the inventive bio-electrode composition or containing the polymer compound having a repeating unit A that contained silver salt of fluorosulfonic acid, silver salt of fluorosulfonimide, or silver salt of fluorosulfonamide, the initial impedance was low, and the impedance was not changed after the bio-electrodes were immersed to water and dried. That is, Examples 1 to 20 each gave a bio-electrode that had high initial electric conductivity and did not cause large change of the electric conductivity even when it is wetted with water or dried. These bio-electrodes of Examples 1 to 20 were light weight and excellent in biocompatibility, and could be manufactured at low cost.

On the other hand, in each Comparative Examples 1 to 4, the living body contact layer of which was formed by using a bio-electrode composition containing each Comparative salt and a polymer compound that did not contain the repeating unit A, the initial impedance was low, but large increase of the impedance occurred such that the order of magnitude was changed after water immersion and drying. That is, each of Comparative Examples 1 to 4 only gave a bio-electrode, the electric conductivity of which was largely decreased when it was wetted by water and dried, although the initial electric conductivity was high.

In each Comparative Examples 5 and 6 using a polymer compound that was not a copolymer having the repeating unit containing silver salt of fluorosulfonic acid, silver salt of fluorosulfonimide, or silver salt of fluorosulfonamide (i.e., did not contain the repeating unit A), the initial impedance was high. That is, each of Comparative Examples 5 and 6 only gave a bio-electrode with low initial electric conductivity.

As described above, it was revealed that bio-electrode, with the living body contact layer being formed by using the inventive bio-electrode composition, had excellent electric conductivity, biocompatibility, and adhesion properties to an electro-conductive base material; without causing large lowering of electric conductivity even when it was wetted with water and dried because the electro-conductive improver was held more securely; was light weight, and could be manufactured at low cost.

It is to be noted that the present invention is not restricted to the foregoing embodiment. The embodiment is just an exemplification, and any examples that have substantially the same feature and demonstrate the same functions and effects as those in the technical concept described in claims of the present invention are included in the technical scope of the present invention.

The invention claimed is:

1. A bio-electrode composition comprising:
    a polymer compound having a repeating unit A that contains silver salt of fluorosulfonic acid, silver salt of fluorosulfonimide, or silver salt of fluorosulfonamide; and
    a carbon material.

2. The bio-electrode composition according to claim 1, wherein the repeating unit A has a structure shown by the following general formula (1)-1, (1)-2, (1)-3, or (1)-4 as the silver salt of fluorosulfonic acid, the silver salt of fluorosulfonimide, or the silver salt of fluorosulfonamide,

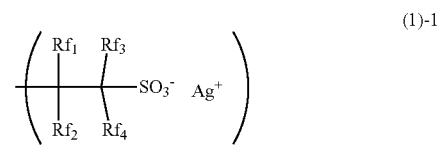

(1)-1

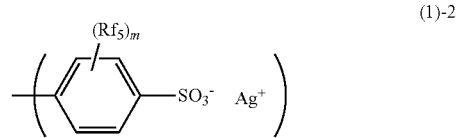

(1)-2

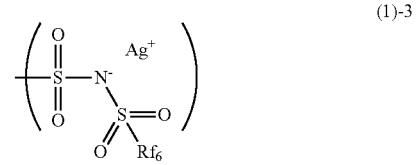

(1)-3

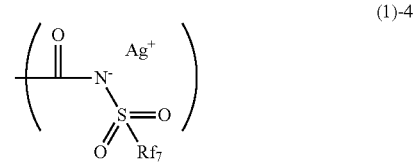

(1)-4 wherein when the repeating unit A has a structure of formula (1)-1, $Rf_1$ and $Rf_2$ each represent a hydrogen atom, a fluorine atom, a trifluoromethyl group, or an oxygen atom, provided that when $Rf_1$ represents an oxygen atom, $Rf_2$ also represents the same oxygen atom as $Rf_1$ to form a carbonyl group together with a carbon atom bonded therewith; $Rf_3$ and $Rf_4$ each represent a hydrogen atom, a fluorine atom, or a trifluoromethyl group, provided that one or more fluorine atoms are contained in $Rf_1$ to $Rf_4$; and when the repeating unit A has a structure of formula (1)-2, (1)-3, or (1)-4, $Rf_5$, $Rf_6$, or $Rf_7$ represents a fluorine atom, or a linear or branched alkyl group having 1 to 4 carbon atoms, provided that one or more fluorine atoms are contained in the linear, branched alkyl group; and "m" is an integer of 1 to 4.

3. The bio-electrode composition according to claim 2, wherein the repeating unit A is one or more repeating units selected from repeating units A1 to A7 shown by the following general formulae (2), (2)

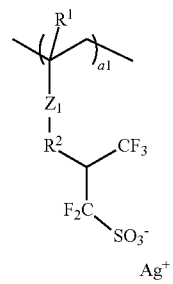
(A1)

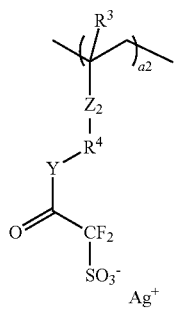
(A2)

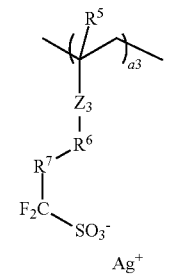
(A3)

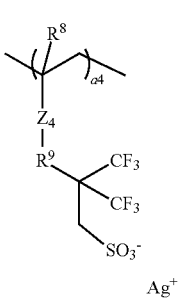
(A4)

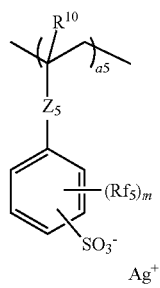
(A5)

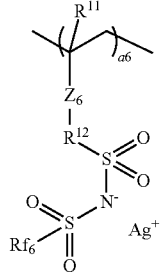
(A6)

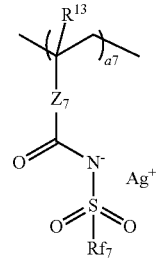
(A7)

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 12 carbon atoms optionally having either or both of an ether group and an ester group; $R^7$ represents a linear or branched alkylene group having 1 to 4 carbon atoms, and one or two of the hydrogen atoms in $R^7$ are optionally substituted with a fluorine atom; $Z_1$, $Z_2$, $Z_3$, $Z_4$, and $Z_6$ each independently represent any of a single bond, a phenylene group, a naphthylene group, an ether group, an ester group, or an amide group; $Z_5$ represents any of a single bond, an ether group, or an ester group; $Z_7$ represents a single bond, an arylene group having 6 to 12 carbon atoms, or —C(=O)—O—$Z_8$—; and $Z_8$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $Z_8$; Y represents an oxygen atom or an —$NR^{14}$— group; $R^{14}$ represents a hydrogen atom, or a linear or branched alkyl group having 1 to 4 carbon atoms, optionally bonded to $R^4$ to form a ring; a1, a2, a3, a4, a5, a6, and a7 satisfy 0<a1+a2+a3+a4+a5+a6+a7≤ 1.0, wherein 0≤a1≤1.0, 0≤ a2≤ 1.0, 0≤ a3≤ 1.0, 0≤ a4≤ 1.0, 0≤ a5≤ 1.0; and when a repeating unit of (A5), (A6), or (A7) is present, $Rf_5$, $Rf_6$, and $Rf_7$ each represent a fluorine atom, or a linear or branched alkyl group having 1 to 4 carbon atoms, provided that one or more fluorine atoms are contained in the linear or branched alkyl group; and "m" is an integer of 1 to 4.

4. The bio-electrode composition according to claim 3, wherein the polymer compound is a copolymer that also has a repeating unit B having (meth)acrylate shown by the following general formula (3),

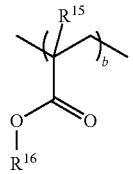
(3)

wherein $R^{15}$ represents a hydrogen atom or a methyl group; $R^{16}$ represents a linear, branched, or cyclic alkyl group having 1 to 30 carbon atoms, a linear, branched, or cyclic alkenyl group having 2 to 30 carbon atoms, or a linear, branched, or cyclic alkynyl group having 2 to 30 carbon atoms; and "b" satisfies $0<b<1.0$.

5. The bio-electrode composition according to claim 2, wherein the polymer compound is a copolymer that also has a repeating unit B having (meth)acrylate shown by the following general formula (3),

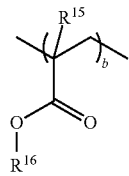
(3)

wherein $R^{15}$ represents a hydrogen atom or a methyl group; $R^{16}$ represents a linear, branched, or cyclic alkyl group having 1 to 30 carbon atoms, a linear, branched, or cyclic alkenyl group having 2 to 30 carbon atoms, or a linear, branched, or cyclic alkynyl group having 2 to 30 carbon atoms; and "b" satisfies $0<b<1.0$.

6. The bio-electrode composition according to claim 1, wherein the repeating unit A is one or more repeating units selected from repeating units A1 to A7 shown by the following general formulae (2), (2)

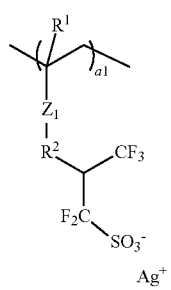
(A1)

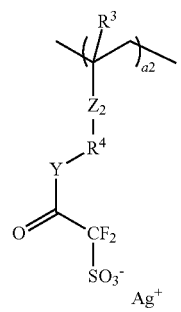
(A2)

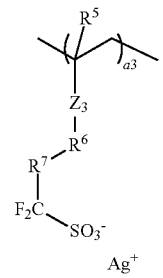
(A3)

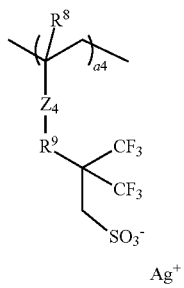
(A4)

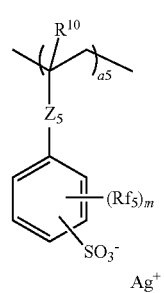
(A5)

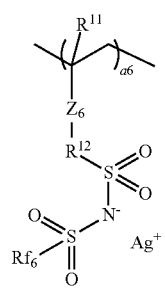
(A6)

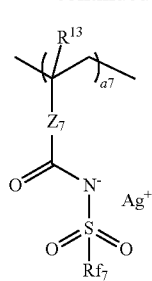

(A7)

wherein $R^1$, $R^3$, $R^5$, $R^8$, $R^{10}$, $R^{11}$, and $R^{13}$ each independently represent a hydrogen atom or a methyl group; $R^2$, $R^4$, $R^6$, $R^9$, and $R^{12}$ each independently represent any of a single bond, an ester group, or a linear, branched, or cyclic hydrocarbon group having 1 to 12 carbon atoms optionally having either or both of an ether group and an ester group; $R^7$ represents a linear or branched alkylene group having 1 to 4 carbon atoms, and one or two of the hydrogen atoms in R' are optionally substituted with a fluorine atom; $Z_1$, $Z_2$, $Z_3$, $Z_4$, and $Z_6$ each independently represent any of a single bond, a phenylene group, a naphthylene group, an ether group, an ester group, or an amide group; $Z_5$ represents any of a single bond, an ether group, or an ester group; $Z_7$ represents a single bond, an arylene group having 6 to 12 carbon atoms, or —C(=O)—O—$Z_8$—; and $Z^8$ represents a linear, branched, or cyclic alkylene group having 1 to 12 carbon atoms, or a divalent aromatic hydrocarbon group having 6 to 10 carbon atoms, optionally having an ether group, a carbonyl group, or an ester group in $Z_8$; Y represents an oxygen atom or an —$NR^{14}$— group; $R^{14}$ represents a hydrogen atom, or a linear or branched alkyl group having 1 to 4 carbon atoms, optionally bonded to $R^4$ to form a ring; a1, a2, a3, a4, a5, a6, and a7 satisfy 0≤a1+a2+a3+a4+a5+a6+a7≤ 1.0, wherein 0≤ a1≤1.0, 0≤ a2≤1.0, 0≤ a3≤ 1.0, 0≤ a4≤ 1.0, 0≤ a5≤ 1.0, 0≤ a6≤ 1.0, 0≤ a7≤ 1.0; and when a repeating unit of (A5), (A6), and/or (A7) is present, $Rf_5$, $Rf_6$, and $Rf_7$ each represent a fluorine atom, or a linear or branched alkyl group having 1 to 4 carbon atoms, provided that one or more fluorine atoms are contained in the linear or branched alkyl group; and "m" is an integer of 1 to 4.

7. The bio-electrode composition according to claim 6, wherein the polymer compound is a copolymer that also has a repeating unit B having (meth)acrylate shown by the following general formula (3),

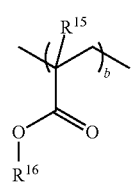

(3)

wherein $R^{15}$ represents a hydrogen atom or a methyl group; $R^{16}$ represents a linear, branched, or cyclic alkyl group having 1 to 30 carbon atoms, a linear, branched, or cyclic alkenyl group having 2 to 30 carbon atoms, or a linear, branched, or cyclic alkynyl group having 2 to 30 carbon atoms; and "b" satisfies 0<b<1.0.

8. The bio-electrode composition according to claim 1, wherein the polymer compound is a copolymer that also has a repeating unit B having (meth)acrylate shown by the following general formula (3),

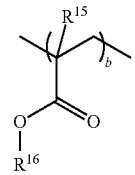

(3)

wherein $R^{15}$ represents a hydrogen atom or a methyl group; $R^{16}$ represents a linear, branched, or cyclic alkyl group having 1 to 30 carbon atoms, a linear, branched, or cyclic alkenyl group having 2 to 30 carbon atoms, or a linear, branched, or cyclic alkynyl group having 2 to 30 carbon atoms; and "b" satisfies 0<b<1.0.

9. The bio-electrode composition according to claim 1, wherein the polymer compound is a copolymer that also has at least one of a repeating unit C having a fluorine atom or a silicon atom and being different than the repeating unit A and a repeating unit D having one or more groups selected from the group consisting of a hydroxy group, a carboxy group, an oxirane group, and an oxetane group.

10. The bio-electrode composition according to claim 1, further comprising an indium tin oxide particle; powder of a metal selected from silver, gold, platinum, copper, and nickel; or a particle coated with a metal selected from silver, gold, platinum, copper, and nickel.

11. The bio-electrode composition according to claim 1, wherein the carbon material is either or both of carbon black and carbon nanotube.

12. A bio-electrode comprising an electro-conductive base material and a living body contact layer formed on the electro-conductive base material;
wherein the living body contact layer is a cured material of the bio-electrode composition according to claim 1.

13. The bio-electrode according to claim 12, wherein the electro-conductive base material comprises one or more species selected from gold, silver, silver chloride, platinum, aluminum, magnesium, tin, tungsten, iron, copper, nickel, stainless, chromium, titanium, and carbon.

14. A method for manufacturing a bio-electrode having an electro-conductive base material and a living body contact layer formed on the electro-conductive base material, comprising:
applying the bio-electrode composition according to claim 1 onto the electro-conductive base material; and curing the bio-electrode composition; thereby forming the living body contact layer.

15. The method for manufacturing a bio-electrode according to claim 14, wherein the electro-conductive base material comprises one or more species selected from gold, silver, silver chloride, platinum, aluminum, magnesium, tin, tungsten, iron, copper, nickel, stainless, chromium, titanium, and carbon.

* * * * *